(12) United States Patent
Mahour et al.

(10) Patent No.: US 11,795,486 B2
(45) Date of Patent: Oct. 24, 2023

(54) ENZYMATIC METHOD FOR PREPARATION OF GDP-FUCOSE

(71) Applicant: Max-Planck-Gesellschaft zur Förderung der Wissenschaften e.V., Munich (DE)

(72) Inventors: Reza Mahour, Magdeburg (DE); Thomas F. T. Rexer, Magdeburg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 18 days.

(21) Appl. No.: 17/593,929

(22) PCT Filed: Mar. 31, 2020

(86) PCT No.: PCT/EP2020/059182
§ 371 (c)(1),
(2) Date: Sep. 28, 2021

(87) PCT Pub. No.: WO2020/021315
PCT Pub. Date: Oct. 8, 2020

(65) Prior Publication Data
US 2022/0177940 A1   Jun. 9, 2022

(30) Foreign Application Priority Data
Apr. 1, 2019 (EP) .................................. 19166549

(51) Int. Cl.
*C12P 19/44* (2006.01)
(52) U.S. Cl.
CPC .................................. *C12P 19/44* (2013.01)
(58) Field of Classification Search
CPC ........... C12P 19/32; C12P 19/44; C12P 19/00; C12P 19/18; C12Y 101/01271; C12Y 207/01052; C12Y 207/07013; C12Y 207/07022; C12Y 402/01047
USPC ...................................................... 435/89
See application file for complete search history.

(56) References Cited

U.S. PATENT DOCUMENTS

2002/0132320 A1   9/2002   Wang et al.

OTHER PUBLICATIONS

Kisselev L., (Structure, 2002, vol. 10: 8-9.*
Kwiatkowski et al., (Biochemistry 38:11643-11650, 1999.*
Wristlock et al., (Quarterly Reviews of Biophysics 2003, vol. 36 (3): 307-340.*
Davos et al., (Proteins: Structure, Function and Genetics, 2000, vol. 41: 98-107.*
Nittymäki et al., "Differential gene expression of GDP-L-fucose-synthesizing enzymes, GDP-fucose transporter and fucosyltransferase VII" APMIS (2006) 114:539-548.
Wittmamn et al., "1H-Tetrazole as Catalyst in Phosphomorpholidate Coupling Reactions: Efficient Synthesis of GDP-Fucose. GDP-Mannose, and UDP-Galactose" J. Org. Chem. (1997) 62:2144-2147.
Tonetti et al., "Synthesis of GDP-L-fucose by the Human FX Protein" J. Biol. Chem. (1996) 271(4):27274-27279
Sullivan et al., "Molecular Cloning of Human GDP-mannose 4,6-Dehydratase and Reconstitution of GDP-fucose Biosynthesis in Vitro" J. Biol. Chem. (1998) 273(14):8193-8202.
Lau et al., "Mechanism and Active Site Residues of GDP-Fucose Synthase" J. Am. Chem. Soc. (2008) 130:17593-17602.
Zdarta et al., "A General Overview of Support Materials for Enzyme Immobilization: Characteristics, Properties, Practical Utility" (2018) 8:92.
Datta et al., "Enzyme immobilization: an overview on techniques and support materials" Biotech (2013) 3:1-9.
Yi et al., "Covalent immobilization of ω-transaminase from *Vibrio fluvialis* JS17 on chitosan beads" Process Biochemistry (2007) 42:895-898.
Martin et al., "Characterization of free and immobilized (S)-aminotransferase for acetophenone production" Appl. Microbiol. Biotechnol. (2007) 76:843-851.
Koszelewski et al., "Immobilization of ω-transaminases by encapsulation in a sol-gel/celite matrix" J. Mol. Catalysis B: Enzymatic (2010) 63:39-44.
Truppo et al., "Development of an Improved Immobilized CAL-B for the Enzymatic Resolution of a Key Intermediate to Odanacatib" Org. Process Res. Dev. (2011) 15:1033-1035.
Mateo et al., "Epoxy Sepabeads: A Novel Epoxy Support for Stabilization of Industrial Enzymes via Very Intense Multipoint Covalent Attachment" Biotechnol. Prog. (2002) 18:629-634.
U.K. Laemmli "Cleavage of Structural Proteins during the Assembly of the Head of Bacteriophage T4"Nature (1970) 227:68-685.
Bradford et al., "A Rapid and Sensitive Method for the Quantitation of Microgram Quantities of Protein Utilizing the Principle of Protein-Dyne Binding" Analytical Biochemistry (1976) 72:284-254.
Li, et al., "One-pot synthesis of GDP-L-fucose by a four-enzyme cascade expressed in *Lactococcus lactis*," Journal of Biotechnology (2017) 264:1-7.
Rexer, et al., "One pot synthesis of GDP-mannose by a multi-enzyme cascade for enzymatic assembly of lipid-linked oligosaccharides," Biotechnology and Bioengineering (2018) 115:192-205.
Wang, et al., "Cell-free enzymatic synthesis of GDP-L-fucose from mannose," Amb Express (2019) 9(74):1-8.

(Continued)

*Primary Examiner* — Robert B Mondesi
*Assistant Examiner* — Mohammad Y Meah
(74) *Attorney, Agent, or Firm* — Knobbe Martens Olson & Bear LLP

(57) ABSTRACT

The present invention relates to an enzyme-catalyzed process for producing GDP-fucose from low-cost substrates guanosine and L-fucose or guanosine and D-Mannose in a single reaction mixture. Said process can be operated (semi) continuously or in batch mode. Further, said process can be adapted to produce fucosylated molecules and biomolecules including glycans, such as human milk oligosaccharides, proteins, peptides, glycoproteins or glycopeptides.

15 Claims, 17 Drawing Sheets

Specification includes a Sequence Listing.

(56) References Cited

OTHER PUBLICATIONS

Zhai, et al., "Enhancing GDP-fucose production in recombinant *Escherichia coli* by metabolic pathway engineering," Enzyme and Microbial Technology (2015) 69:38-45.

Zhao, et al., "Enzymatic route to preparative-scale synthesis of UDP-GlcNAc/GalNAc, their analogues and GDP-fucose," Nature Protocols (2010) 5(4):636-646.

International Search Report and Written Opinion dated Jun. 23, 2021 for PCT Application No. PCT/EP2020/059182, filed Mar. 31, 2020.

International Preliminary Report on Patentability dated Sep. 28, 2021 for PCT Application No. PCT/EP2020/059182, filed Mar. 31, 2020.

* cited by examiner

A

B

2'-Fucosyllactose
(2'-FL)

3-Fucosyllactose
(3-FL)

Lacto-*N*-fucopentaose I
(LNFP I)

Lacto-*N*-fucopentaose III
(LNFP III)

Lacto-*N*-difucohexaose I
(LNDFH I)

Lacto-*N*-difucohexaose II
(LNDFH II)

○ Glucose   ● Galactose   □ *N*-Acetylglucosamine   ▲ L-Fucose

ENZYMATIC METHOD FOR PREPARATION OF GDP-FUCOSE

The present application is the national phase entry of PCT Application No. PCT/EP2020/059182, filed Mar. 31, 2020, which claims priority to EP Application No. 19166549.6, filed Apr. 1, 2019, which are incorporated by reference in its entirety.

FIELD OF THE INVENTION

The present invention relates to an enzyme-catalyzed process for producing GDP-fucose from low-cost substrates guanosine and L-fucose or guanosine and D-mannose in a single reaction mixture. Said process can be operated semi-continuously, even continuously or in a fed batch mode. Further, said process can be adapted to produce fucosylated molecules and biomolecules including glycans, such as human milk oligosaccharides, proteins, peptides, glycoproteins or glycopeptides.

BACKGROUND OF THE INVENTION

Guanosine 5'-diphospho-β-L-fucose (GDP-fucose or GDP-Fuc) is a key substrate for a large number of biotechnological applications and food technology. It is the substrate for the core fucosylation of anti-inflammatory antibodies which are used to treat autoimmune diseases. Moreover, GDP-fucose is needed for the production of carbohydrate vaccines and in the growing field of personalized medicine, i.e. preparation of glyconanomaterials for drug delivery. In infant food (human milk), fucosylated oligosaccharides comprise the majority of sugars and, thus, there is a high demand to include fucosylated sugars in synthetically produced dairy products for infants.

However, in spite of the high demand for GDP-fucose (in the order of tons per year), the availability of GDP-fucose is very limited, even for researchers. Up to now, the price of low endotoxin GDP-fucose is above 3,000 Euros per gram. Due to the high price of GDP-fucose not only basic and applied research activities are hampered but also industrial applications are hindered.

Bioprocess engineering strategies to synthesize GDP-fucose can be classified into in vivo and in vitro processes: Microorganisms are metabolically engineered in order to produce GDP-fucose, either intracellularly or extracellularly, as part of their metabolism. However, low yields, high levels of unwanted by-products, the required time for cell line design and the complicated scale up are drawbacks. Taking into account regulatory aspects, specifically for infant food, application of genetically modified organisms (GMOs) can severely delay the approval process.

GDP-fucose can also be produced in vitro by using biocatalytic (enzymatic) processes (see *APMIS* 2006, 114, 539-548). For example, the enzymatic synthesis of GDP-fucose from L-fucose and guanosine triphosphate using bifunctional enzyme L-fucose pyrophosphorylase (FKP) is reported by Zhao et al. (Nat Protoc. 2010 5(4): 636-646). Wittmann et al. (*J. Org. Chem.* 1997, 62, 2144-2147) describe the synthesis of GDP-fucose from fucose-1-phosphate and guanosine 5'-monophospho-morpholidate using phosphoamidite chemistry. Tonetti et al. (*J. Biol. Chem.* 1996, 271(44), 27274-27279) report on the homodimeric NADP(H)-binding protein FX, which apparently catalyzes a combined epimerase and NADPH-dependent reductase activity, thus converting GDP-4-keto-6-D-deoxymannose to GDP-L-fucose. Sullivan et al. (*J. Biol. Chem.* 1998, 273(14), 8193-8202) describe the in vitro preparation of GDP-fucose from GDP-mannose using recombinant human GDP-mannose4,6-dehydratase and the FX protein. Lau et al. report on the biosynthesis of GDP-L-fucose from GDP-D-mannose and investigated the enzyme GDP-fucose synthase which is involved in the synthesis. The enzyme converts GDP-4-keto-6-deoxy-D-mannose into GDP-L-fucose (J. Am. Chem. Soc. 2008, 130, 17593-17602). Rexer et al. report one-pot synthesis of GDP-mannose from mannose by a multi-enzyme cascade of glucokinase (Glk), phosphomannomutase (ManB), mannose-1-phosphate-guanylyltransferase (ManC), inorganic pyrophosphatase (PmPpA), and 1-domain polyphosphate kinase 2 (1D-Ppk2) expressed in *E. coli*. (*Biotechnology and Bioengineering* 2018, 115, 192-205). There is a long-felt need for a method of producing GDP-fucose in a cost-effective manner starting from low cost and readily available substrates.

Thus, it is the objective of the present invention to provide a cost-effective and efficient method for the preparation of GDP-fucose.

The objective of the present invention is solved by the teaching of the independent claims. Further advantageous features, aspects and details of the invention are evident from the dependent claims, the description, the figures, and the examples of the present application.

DESCRIPTION OF THE INVENTION

In biochemistry nucleotide sugars are well known as active forms of monosaccharides and in glycosylation reactions nucleotide sugars are known to act as glycosyl donors. Glycosyltransferases (GTFs) are enzymes that catalyze the transfer of saccharide moieties from activated nucleotide sugars to nucleophilic glycosyl acceptor molecules. Thus, in biochemistry the glycosylation reactions are catalyzed by glycosyltransferases.

In order to act as glycosyl donors it is essential that the respective monosaccharides are present in a highly energetic form, like for example in form of nucleotide sugars, particularly nucleotide diphospho sugars derived from uridine diphosphate, guanosine diphosphate or cytosine diphosphate and so on. Examples of well known nucleotide sugars are UDP-glucose, UDP-galactose, UDP-GlcNAc, UDP-GalNac, UDP-xylose, UDP-glucuronic acid, GDP-mannose and GDP-fucose. It is well known that the conversion of simple monosaccharides into activated nucleotide sugars can be achieved by enzyme catalyzed reaction of a nucleoside triphosphate (NTP) and a glycosyl monophosphate, wherein the glycosyl monophosphate contains a phosphate group at the anomeric carbon.

In order to obtain a nucleoside diphosphate (NDP)-monosaccharide the used monosaccharide needs to be converted into a glycosyl monophosphate derivative. In general, said reaction can be accomplished by applying specific enzymes like phosphotransferases and additionally phosphomutases, if required, to obtain the desired monosaccharide-1-phosphate. Phosphotransferases are enzymes classified under EC number 2.7 that catalyze phosphorylation reactions. Phosphotransferases are further classified according to their acceptor molecule. For example, phosphotransferases under EC 2.7.1 are phosphotransferases with an alcohol group as acceptor. Phosphomutases are isomerases, i.e. enzymes that can catalyze an internal transfer of a phosphate group. Phosphomutases are required in case the phosphorylation of the substrate via phosphotransferase results in a monosaccharide-6-phosphate, like in case of D-mannose or D-glucose for example mannose-6-phosphat or glucose-6-phosphat respectively. The respective phospho-mutase then catalyzes the internal transfer of the phosphate group which results in the conversion of mannose-6-phosphate into mannose-1-phosphate or glucose-6-phosphate into glucose-1-phosphate, respectively.

Kinases are enzymes which form a part of the family of the phosphotransferases. Kinases are enzymes that catalyze the transfer of phosphate groups from high-energy, phosphate-donating molecules to specific substrates. This process is known as phosphorylation, where the substrate gains a phosphate group and the high-energy adenosine triphosphate (ATP) molecule donates a phosphate group. This transesterification produces a phosphorylated substrate and ADP. Thus, in order to obtain a monosaccharide-1-phosphate, suitable kinases like a fucokinase or N-acetyl-hexosamine-1-kinase may be applied to obtain fucose-1-phosphate from L-fucose or mannose-1-phosphate from D-mannose respectively.

With the use of nucleotidyltransferases a nucleoside triphosphate (NTP) and a monosaccharide-1-phosphate can be converted to the respective nucleoside diphosphate (NDP)-monosaccharide. Nucleotidyltransferases are transferase enzymes of phosphorus-containing groups and are classified under EC number 2.7.7. For the different naturally occurring nucleotides nucleotide-specific nucleotidyltransferases are known in the art, e.g. uridyltransferases transfer uridylyl-groups, adenyltransferases transfer adenylyl-groups, guanylyltransferases transfer guanylyl-groups, cytidylyltransferases transfer cytidylyl-groups and thymidilyl-transferases transfer thymidilyl-groups. Thus, nucleotidyltransferases are suitable to catalyze the reaction of monosaccharide-1-phosphates with nucleoside triphosphates, e.g. fucose-1-phosphate with guanosine triphosphate (GTP) to obtain GDP-fucose or mannose-1-phosphate with guanosine triphosphate (GTP) to obtain GDP-mannose. In case of GDP-fucose and GDP-mannose a guanylyltransferase is suitable for catalyzing the reaction with guanosine triphosphate (GTP).

Guanosine diphosphate (GDP)-monosaccharides which relate to naturally occurring GDP-monosaccharides are GDP-mannose and GDP-fucose. The above described general reaction scheme to obtain the GDP-monosaccharides can be conducted with guanosine triphosphate and mannose-1-phosphat (Man-1-P) in case of GDP-mannose and fucose-1-phosphate (Fuc-1-P) in case of GDP-fucose with specific guanylyltransferases which catalyze the reaction to obtain the desired GDP-mannose or GDP-fucose respectively.

However one disadvantage of the enzyme-catalyzed reaction scheme to obtain nucleoside diphosphate (NDP)-monosaccharides is based on the fact that the starting materials, in particular the respective nucleoside triphosphates are very expensive and thus the synthesis pathway results in a cost-intensive synthesis of NDP-monosaccharides and in particular of GDP-fucose or GDP-mannose. As already described above for GDP-fucose there is a need in the art to provide a cost effective and efficient method for preparation of nucleoside diphosphate monosaccharides, like GDP-fucose or GDP-mannose, and in particular there is a need to provide a cost effective and efficient method for preparation of GDP-fucose from low cost and readily available starting materials.

With regard to GDP-monosaccharides, GDP-fucose and GDP-mannose relate to naturally occurring activated GDP-sugars in mammals. Therefore guanosine has been identified as suitable nucleotide and L-fucose and D-mannose have been identified as suitable monosaccharides for the preparation of GDP-fucose. It should be clear that with regard to an enzyme-catalyzed reaction at least suitable enzymes must be provided. Therefore the inventors have identified guanosine and readily available monosaccharides, such as L-fucose or D-mannose as suitable starting materials for the production of GDP-fucose in an enzymatic one-pot cascade reaction.

A process for biocatalytic production of GDP-fucose starting from guanosine and L-fucose or guanosine and D-mannose was not established so far.

In order to provide a cost-effective and efficient method for the preparation of GDP-fucose guanosine and L-fucose were identified as suitable starting materials for the production of GDP-fucose in an enzymatic cascade reaction as depicted in FIG. 1 which consists of (a) the formation of fucose-1-phosphate (Fuc-1-P) from L-fucose and adenosine triphosphate (ATP; catalytic amount), (b) the formation of guanosine triphosphate (GTP) from guanosine and polyphosphate, and (c) the reaction of fucose-1-phosphate with guanosine triphosphate (GTP) to GDP-fucose. It was envisioned that GDP-fucose may be produced from L-fucose and guanosine in the presence of a guanosine kinase, a polyphosphate kinase, and a L-fucokinase/L-fucose-1-phosphate guanylyltransferase in a suitable buffer (FIG. 2).

Furthermore guanosine and D-mannose were identified as suitable starting materials for the production of GDP-fucose in an enzymatic cascade reaction as depicted in FIG. 3 which consist of (a) the formation of mannose-1-phosphat (Man-1-P) from D-mannose and adenosine triphosphate (ATP), (b) the formation of guanosine triphosphate (GTP) from guanosine and polyphosphate, and (c) the reaction of mannose-1-phosphate with guanosine triphosphate (GTP) to GDP-mannose and (d) the conversion of GDP-mannose to GDP-fucose. It was envisioned that GDP-fucose may be produced from D-mannose and guanosine in the presence of a guanosine kinase, a polyphosphate kinase and either a glucokinase, a phosphomannomutase, a mannose-1-phosphate guanylyltransferase, a GDP-mannose 4,6-dehydratase and a GDP-L-fucose synthase or a N-acetylhexosamine-1-kinase, a mannose-1-phosphate guanylyltransferase, a GDP-mannose-4,6-dehydratase and a GDP-L-fucose-synthase in a suitable buffer.

However, any attempts to produce GDP-fucose from L-fucose and guanosine or D-mannose and guanosine in this enzymatic cascade reaction were unsuccessful and no formation of GDP-fucose was observed (Example 3).

Surprisingly, the inventors have found that by solubilizing guanosine in a co-solvent, such as dimethyl sulfoxide, a nearly complete conversion of guanosine and L-fucose to GDP-fucose was achieved after already three hours (Example 2). Also, the co-solvent did not affect the activity of the enzymes used in the preparation of GDP-fucose. The titer is above the solubility of the substrate, which is achieved through using a co-solvent. Furthermore, the inventors have found that by solubilizing guanosine in a co-solvent, such as dimethyl sulfoxide, a nearly complete conversion of guanosine and D-mannose to GDP-fucose was achieved. Also, the co-solvent did not affect the activity of the enzymes used in the preparation of GDP-fucose from guanosine and D-mannose.

For example, the method of the present invention is beneficial over the above described methods known in the art for the enzymatic synthesis of GDP-fucose from L-fucose and guanosine triphosphate, since the expensive guanosine triphosphate starting material can be avoided and replaced with simpler nucleoside guanosine, which results in a cost-effective and efficient method for the preparation of GDP-fucose, as described herein.

Thus, the present invention is directed to a method for producing guanosine 5'-diphospho-β-L-fucose from guanosine and L-fucose or from guanosine and D-mannose comprising the following steps:

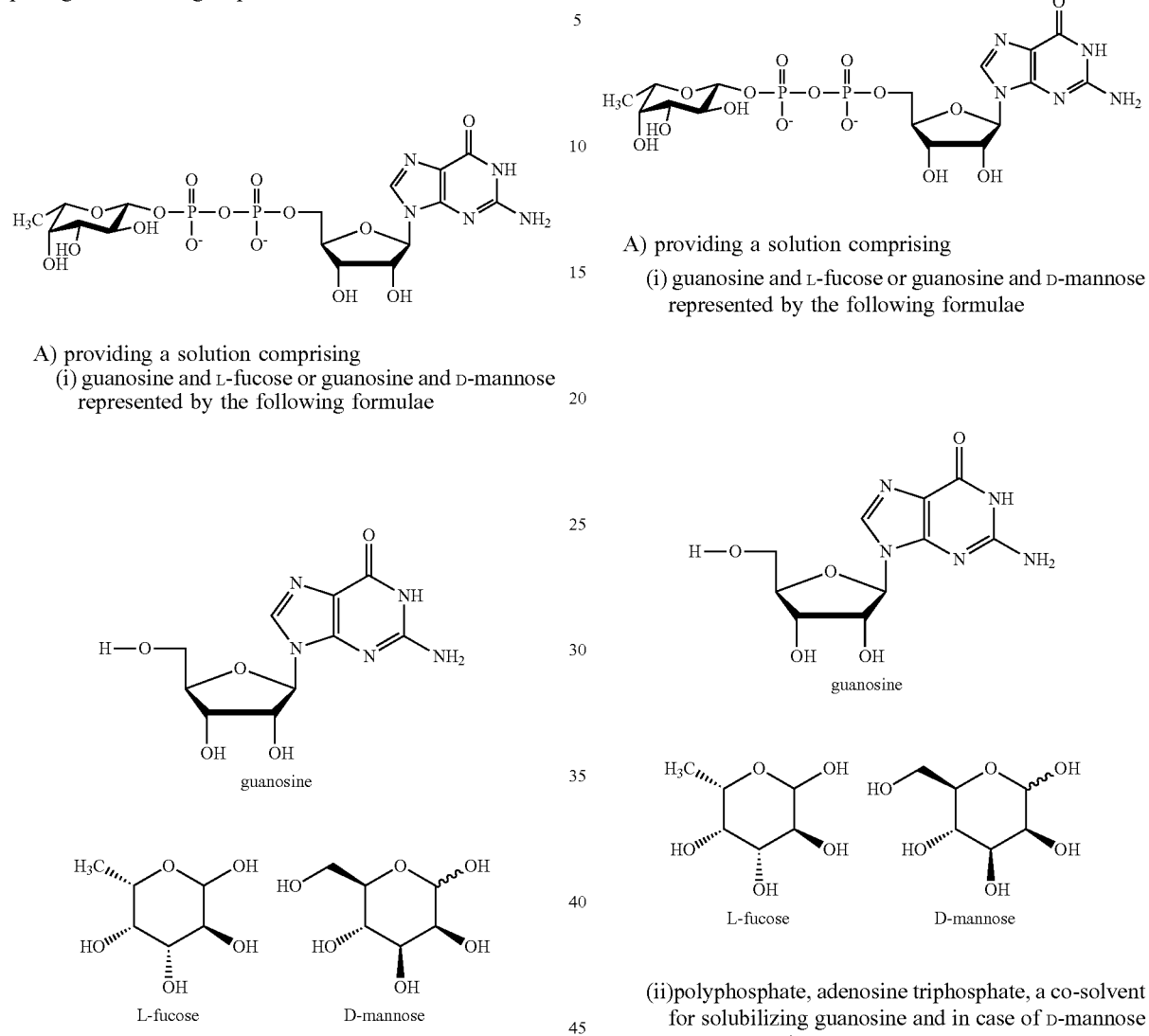

A) providing a solution comprising
(i) guanosine and L-fucose or guanosine and D-mannose represented by the following formulae guanosine L-fucose   D-mannose (ii) polyphosphate, adenosine triphosphate and a co-solvent for solubilizing guanosine; and
providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose 4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent.

The present invention is directed to a method for producing guanosine 5'-diphospho-β-L-fucose from guanosine and L-fucose or from guanosine and D-mannose comprising the following steps:

A) providing a solution comprising
(i) guanosine and L-fucose or guanosine and D-mannose represented by the following formulae guanosine L-fucose   D-mannose (ii) polyphosphate, adenosine triphosphate, a co-solvent for solubilizing guanosine and in case of D-mannose NADPH; and
providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate, NADPH and the co-solvent.

In a preferred embodiment the present invention is directed to a method for producing guanosine 5'-diphospho-β-L-fucose from guanosine and D-mannose comprising the following steps:

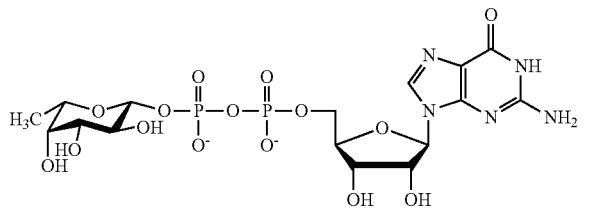

A) providing a solution comprising
  (i) guanosine and D-mannose represented by the following formulae

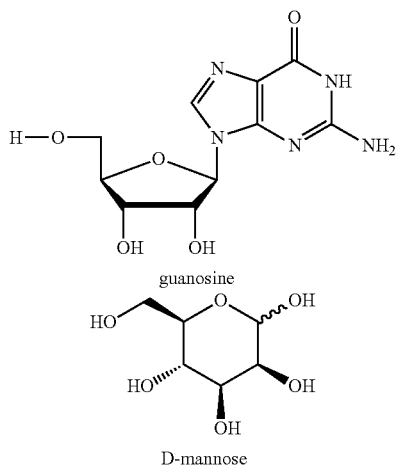

(ii) polyphosphate, adenosine triphosphate and a co-solvent for solubilizing guanosine; and
  providing a set of enzymes comprising either (a) a guanosine kinase, a polyphosphate kinase and a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent.

In a preferred embodiment the present invention is directed to a method for producing guanosine 5'-diphospho-β-L-fucose from guanosine and L-fucose comprising the following steps:

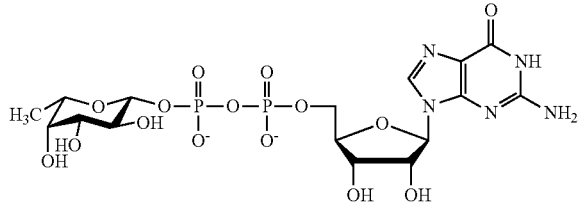

A) providing a solution comprising
  (i) guanosine and L-fucose represented by the following formulae

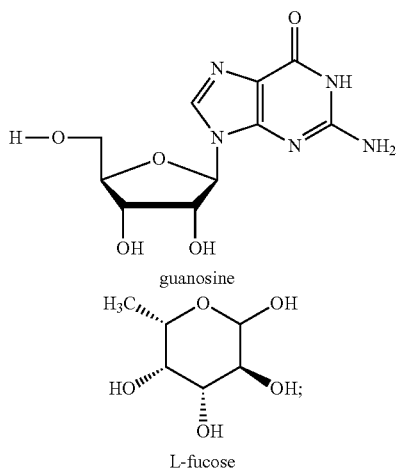

(ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent.

Alternatively worded, the present invention is directed to a method for producing guanosine 5'-diphospho-β-L-fucose from guanosine and L-fucose or D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent.

Alternatively worded, the present invention is directed to a method for producing guanosine 5'-diphospho-β-L-fucose from guanosine and L-fucose comprising the following steps:
A) providing a solution comprising
  (i) guanosine and L-fucose;
  (ii) polyphosphate, adenosine triphosphate and a co-solvent for solubilizing guanosine; and
  providing the following enzymes comprising a guanosine kinase, a polyphosphate kinase, and a L-fucokinase/L-fucose-1-phosphate guanylyl-transferase;

B) producing guanosine 5'-diphospho-β-L-fucose from guanosine and fucose in the presence of the enzymes, polyphosphate, adenosine triphosphate and the co-solvent.

Also, the present invention is directed to a method for producing guanosine 5'-diphospho-β-L-fucose from guanosine and L-fucose comprising the following steps:

A) providing a solution comprising
  (i) guanosine and L-fucose;
  (ii) polyphosphate, adenosine triphosphate and a co-solvent for solubilizing guanosine; and
  providing the following enzymes comprising a guanosine kinase, a polyphosphate kinase, and a L-fucokinase/L-fucose-1-phosphate guanylyl-transferase;
B) producing guanosine 5'-diphospho-β-L-fucose from guanosine and fucose in the presence of the enzymes, polyphosphate, adenosine triphosphate and the co-solvent, wherein the conversion of guanosine to guanosine 5'-diphospho-β-L-fucose is at least 78% after 3 hours.

The production step B) of guanosine 5'-diphospho-β-L-fucose from guanosine and L-fucose according to the invention comprises
  (a) forming fucose-1-phosphate (Fuc-1-P) from L-fucose and adenosine triphosphate being catalyzed by a L-fucokinase/L-fucose-1-phosphate guanylyltransferase,
  (b) forming guanosine triphosphate (GTP) from guanosine, adenosine triphosphate and polyphosphate being catalyzed by a guanosine kinase and a polyphosphate kinase; and
  (c) reacting fucose-1-phosphate with guanosine triphosphate to GDP-fucose in the presence of a L-fucokinase/L-fucose-1-phosphate guanylyltransferase.

Apparently, the steps (a) and (b) may be carried out simultaneously or successively. Also, their order may be reverted to (b)→(a)→(c).

Thus, the present invention is directed to a method for producing guanosine 5'-diphospho-β-L-fucose from guanosine and L-fucose comprising the following steps:

A) providing a solution comprising
  (i) guanosine and L-fucose;
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent by
  (a) forming fucose-1-phosphate from L-fucose and adenosine triphosphate being catalyzed by a L-fucokinase/L-fucose-1-phosphate guanylyltransferase,
  (b) forming guanosine triphosphate from guanosine, adenosine triphosphate and polyphosphate being catalyzed by a guanosine kinase and a polyphosphate kinase; and
  (c) reacting fucose-1-phosphate with guanosine triphosphate to GDP-fucose in the presence of a L-fucokinase/L-fucose-1-phosphate guanylyltransferase.

More specifically, the production step B) of guanosine 5'-diphospho-β-L-fucose from guanosine and fucose according to the invention comprises
  (a) forming fucose-1-phosphate (Fuc-1-P) from L-fucose and adenosine triphosphate being catalyzed by a L-fucokinase/L-fucose-1-phosphate guanylyltransferase,
  (b1) forming guanosine monophosphate (GMP) from guanosine and adenosine triphosphate being catalyzed by a guanosine kinase;
  (b2) forming guanosine triphosphate (GTP) from guanosine monophosphate and polyphosphate being catalyzed by a polyphosphate kinase; and
  (c) reacting fucose-1-phosphate with guanosine triphosphate to GDP-fucose in the presence of a L-fucokinase/L-fucose-1-phosphate guanylyltransferase.

Apparently, the step (a) may be carried out before, simultaneously to or after step (b1) or (b2). Thus, the step order may also be reverted to (b1)→(b2)→(a)→(c).

Thus, the present invention is directed to a method for producing guanosine 5'-diphospho-β-L-fucose from guanosine and L-fucose comprising the following steps:

A) providing a solution comprising
  (i) guanosine and L-fucose;
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and L-fucose in the presence of the set of enzymes, polyphosphate, adenosine triphosphate and the co-solvent by
  (a) forming fucose-1-phosphate from L-fucose and adenosine triphosphate being catalyzed by a L-fucokinase/L-fucose-1-phosphate guanylyl-transferase,
  (b1) forming guanosine monophosphate from guanosine and adenosine triphosphate being catalyzed by a guanosine kinase;
  (b2) forming guanosine triphosphate from guanosine monophosphate and polyphosphate being catalyzed by a polyphosphate kinase; and
  (c) reacting fucose-1-phosphate with guanosine triphosphate to GDP-fucose in the presence of a L-fucokinase/L-fucose-1-phosphate guanylyl-transferase.

Even more specifically, the production step B) of guanosine 5'-diphospho-β-L-fucose from guanosine and L-fucose according to the invention comprises
  (a) forming fucose-1-phosphate (Fuc-1-P) from L-fucose and adenosine triphosphate being catalyzed by a L-fucokinase/L-fucose-1-phosphate guanylyl-transferase,
  (b1) forming guanosine monophosphate (GMP) from guanosine and adenosine triphosphate being catalyzed by a guanosine kinase;
  (b2') forming guanosine diphosphate (GDP) from guanosine monophosphate and polyphosphate being catalyzed by a polyphosphate kinase
  (b2") forming guanosine triphosphate (GTP) from guanosine diphosphate and polyphosphate being catalyzed by a polyphosphate kinase; and
  (c) reacting fucose-1-phosphate with guanosine triphosphate to GDP-fucose in the presence of a L-fucokinase/L-fucose-1-phosphate guanylyltransferase.

Apparently, the step (a) am be carried out before, simultaneously to or after steps (b1), (b2') and (b2"). Thus, the step order may also be reverted to (b1)→(b2')→(b2")→(a)→(c).

Thus, the present invention is directed to a method for producing guanosine 5'-diphospho-β-L-fucose from guanosine and L-fucose comprising the following steps:

A) providing a solution comprising
  (i) guanosine and L-fucose;
  (ii) polyphosphate, adenosine triphosphate and a co-solvent for solubilizing guanosine; and providing a set of enzymes comprising a guanosine kinase, a polyphosphate kinase, and a L-fucokinase/L-fucose-1-phosphate guanylyltransferase;

B) producing guanosine 5'-diphospho-β-L-fucose from guanosine and L-fucose in the presence of the set of enzymes, polyphosphate, adenosine triphosphate and the co-solvent by
  (a) forming fucose-1-phosphate from L-fucose and adenosine triphosphate being catalyzed by a L-fucokinase/L-fucose-1-phosphate guanylyl-transferase,
  (b1) forming guanosine monophosphate from guanosine and adenosine triphosphate being catalyzed by a guanosine kinase;
  (b2') forming guanosine diphosphate from guanosine monophosphate and polyphosphate being catalyzed by a polyphosphate kinase
  (b2") forming guanosine triphosphate from guanosine diphosphate and polyphosphate being catalyzed by a polyphosphate kinase; and
  (c) reacting fucose-1-phosphate with guanosine triphosphate to GDP-fucose in the presence of a L-fucokinase/L-fucose-1-phosphate guanylyl-transferase.

The production step B) of guanosine 5'-diphospho-α-D-mannose from guanosine and D-mannose according to the invention comprises
  (a) forming mannose-1-phosphate (Man-1-P) from D-mannose and adenosine triphosphate being catalyzed by a N-acetylhexosamine-1-kinase
  or
    forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase
  (b) forming guanosine triphosphate (GTP) from guanosine, adenosine triphosphate and polyphosphate being catalyzed by a guanosine kinase and a polyphosphate kinase; and
  (c) reacting mannose-1-phosphate with guanosine triphosphate to GDP-mannose in the presence of a D-mannose-1-phosphate guanylyltransferase.

The production step B) of guanosine 5'-diphospho-β-L-fucose from guanosine and D-mannose according to the invention comprises
  (a) forming mannose-1-phosphate (Man-1-P) from D-mannose and adenosine triphosphate being catalyzed by a N-acetylhexosamine-1-kinase
  or
    forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase
  (b) forming guanosine triphosphate (GTP) from guanosine, adenosine triphosphate and polyphosphate being catalyzed by a guanosine kinase and a polyphosphate kinase; and
  (c) reacting mannose-1-phosphate with guanosine triphosphate to GDP-mannose in the presence of a D-mannose-1-phosphate guanylyltransferase
  (d) forming GDP-4-dehydro-6-deoxy-alpha-D-mannose from GDP-mannose being catalyzed by GDP-mannose-4,6-dehydratase; and
  (e) forming GDP-fucose from GDP-4-dehydro-6-deoxy-alpha-D-mannose and NADPH being catalyzed by GDP-L-fucose synthase.

Apparently, the steps (a) and (b) may be carried out simultaneously or successively. Also, their order may be reverted to (b)→(a)→(c).

Thus, the present invention is directed to a method for producing guanosine 5'-diphospho-β-L-fucose from guanosine and D-mannose comprising the following steps:
  A) providing a solution comprising
    (i) guanosine and D-mannose;
    (ii) polyphosphate, adenosine triphosphate and a co-solvent for solubilizing guanosine; and
    providing a set of enzymes comprising a guanosine kinase, a polyphosphate kinase and either (a) a glucokinase, phosphomannomutase, a mannose-1-phosphate guanylyltransferase, a GDP-mannose-4,6-dehydratase and a GDP-L-fucose-synthase or (b) a N-acetylhexosamine-1-kinase, a mannose-1-phosphate guanylyltransferase, a GDP-mannose 4,6-dehydratase and a GDP-L-fucose-synthase;
  B) producing guanosine 5'-diphospho-β-L-fucose from guanosine and D-mannose in the presence of the set of enzymes, polyphosphate, adenosine triphosphate and the co-solvent by
    (a) forming mannose-1-phosphate (Man-1-P) from D-mannose and adenosine triphosphate being catalyzed by a N-acetylhexosamine-1-kinase
    or
      forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase
    (b) forming guanosine triphosphate (GTP) from guanosine, adenosine triphosphate and polyphosphate being catalyzed by a guanosine kinase and a polyphosphate kinase; and
    (c) reacting mannose-1-phosphate with guanosine triphosphate to GDP-mannose in the presence of a D-mannose-1-phosphate guanylyltransferase
    (d) forming GDP-4-dehydro-6-deoxy-alpha-D-mannose from GDP-mannose being catalyzed by GDP-mannose-4,6-dehydratase; and
    (e) forming GDP-fucose from GDP-4-dehydro-6-deoxy-alpha-D-mannose and NADPH being catalyzed by GDP-L-fucose synthase.

More specifically, the production step B) of guanosine 5'-diphospho-β-L-fucose from guanosine and D-mannose according to the invention comprises
  (a) forming mannose-1-phosphate (Man-1-P) from D-mannose and adenosine triphosphate being catalyzed by a N-acetylhexosamine-1-kinase
  or
    forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase
  (b1) forming guanosine monophosphate (GMP) from guanosine and adenosine triphosphate being catalyzed by a guanosine kinase;
  (b2) forming guanosine triphosphate (GTP) from guanosine monophosphate and polyphosphate being catalyzed by a polyphosphate kinase; and
  (c) reacting mannose-1-phosphate with guanosine triphosphate to GDP-mannose in the presence of a D-mannose-1-phosphate guanylyltransferase (d) forming GDP-4-dehydro-6-deoxy-alpha-D-mannose from GDP-mannose being catalyzed by GDP-mannose-4,6-dehydratase; and (e) forming GDP-fucose from GDP-4-dehydro-6-deoxy-alpha-D-mannose and NADPH being catalyzed by GDP-L-fucose synthase.

Apparently, the step (a) may be carried out before, simultaneously to or after step (b1) or (b2). Thus, the step order may also be reverted to (b1)→(b2)→(a)→(c).

Thus, the present invention is directed to a method for producing guanosine 5'-diphospho-β-L-fucose from guanosine and D-mannose comprising the following steps:

A) providing a solution comprising
  (i) guanosine and D-mannose;
  (ii) polyphosphate, adenosine triphosphate and a co-solvent for solubilizing guanosine; and
  providing a set of enzymes comprising a guanosine kinase, a polyphosphate kinase and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent by (a) forming mannose-1-phosphate (Man-1-P) from D-mannose and adenosine triphosphate being catalyzed by a N-acetylhexosamine-1-kinase
or
forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase (b1) forming guanosine monophosphate (GMP) from guanosine and adenosine triphosphate being catalyzed by a guanosine kinase;

(b2) forming guanosine triphosphate (GTP) from guanosine monophosphate and polyphosphate being catalyzed by a polyphosphate kinase; and (c) reacting mannose-1-phosphate with guanosine triphosphate to GDP-mannose in the presence of a D-mannose-1-phosphate guanylyltransferase (d) forming GDP-4-dehydro-6-deoxy-alpha-D-mannose from GDP-mannose being catalyzed by GDP-mannose-4,6-dehydratase; and (e) forming GDP-fucose from GDP-4-dehydro-6-deoxy-alpha-D-mannose and NADPH being catalyzed by GDP-L-fucose synthase.

Even more specifically, the production step B) of guanosine 5'-diphospho-β-L-fucose from guanosine and D-mannose according to the invention comprises (a) forming mannose-1-phosphate (Man-1-P) from D-mannose and adenosine triphosphate being catalyzed by a N-acetylhexosamine-1-kinase
or
forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase (b1) forming guanosine monophosphate (GMP) from guanosine and adenosine triphosphate being catalyzed by a guanosine kinase;

(b2') forming guanosine diphosphate (GDP) from guanosine monophosphate and polyphosphate being catalyzed by a polyphosphate kinase (b2") forming guanosine triphosphate (GTP) from guanosine diphosphate and polyphosphate being catalyzed by a polyphosphate kinase; and (c) reacting mannose-1-phosphate with guanosine triphosphate to GDP-mannose in the presence of a D-mannose-1-phosphate guanylyltransferase (d) forming GDP-4-dehydro-6-deoxy-alpha-D-mannose from GDP-mannose being catalyzed by GDP-mannose-4,6-dehydratase; and (e) forming GDP-fucose from GDP-4-dehydro-6-deoxy-alpha-D-mannose and NADPH being catalyzed by GDP-L-fucose synthase.

Apparently, the step (a) am be carried out before, simultaneously to or after steps (b1), (b2') and (b2"). Thus, the step order may also be reverted to (b1)→(b2')→(b2")→(a)→(c).

Thus, the present invention is directed to a method for producing guanosine 5'-diphospho-β-L-fucose from guanosine and D-mannose comprising the following steps:

A) providing a solution comprising
  (i) guanosine and D-mannose;
  (ii) polyphosphate, adenosine triphosphate and a co-solvent for solubilizing guanosine; and
  providing a set of enzymes comprising a guanosine kinase, a polyphosphate kinase and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent by (a) forming mannose-1-phosphate (Man-1-P) from D-mannose and adenosine triphosphate being catalyzed by a N-acetylhexosamine-1-kinase
or
forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase (b1) forming guanosine monophosphate (GMP) from guanosine and adenosine triphosphate being catalyzed by a guanosine kinase;

(b2') forming guanosine diphosphate (GDP) from guanosine monophosphate and polyphosphate being catalyzed by a polyphosphate kinase (b2") forming guanosine triphosphate (GTP) from guanosine diphosphate and polyphosphate being catalyzed by a polyphosphate kinase; and (c) reacting mannose-1-phosphate with guanosine triphosphate to GDP-mannose in the presence of a D-mannose-1-phosphate guanylyltransferase (d) forming GDP-4-dehydro-6-deoxy-alpha-D-mannose from GDP-mannose being catalyzed by GDP-mannose-4,6-dehydratase; and (e) forming GDP-fucose from GDP-4-dehydro-6-deoxy-alpha-D-mannose and NADPH being catalyzed by GDP-L-fucose synthase.

The inventive method for producing GDP-fucose has the following significant advantages over the methods described in the prior art:

- significant cost reduction with respect to starting materials, i.e. no expensive GDP or GTP is required,
- the method can be performed in a continuous manner, thereby potentially allowing providing GDP-fucose on a ton scale per year,
- cell-free process, thereby avoiding adverse GMO aspects (regulation, labelling),
- direct use of cell-free extracts, no costs for biocatalyst purification,
- enzymes can be immobilized on low-cost, commercially available and ready to use solid supports,
- nearly quantitative yield with respect to guanosine,
- high scalability renders the inventive method useful for industrial applications.

Due to the addition of small amounts of a co-solvent for solubilizing guanosine, the inventors were able to establish a multi enzyme cascade reaction from guanosine to guanosine 5'-diphospho-β-L-fucose with a high conversion rate. Preferably, the co-solvent is an organic solvent selected from the group comprising: methanol, ethanol, isopropanol, n-propanol, isobutanol, n-butanol, tert-butanol, acetonitrile, acetone and dimethyl sulfoxide. Preferably the co-solvent is a polar aprotic solvent, such as dimethyl sulfoxide or dimethylformamide. Preferably the co-solvent does not inhibit enzyme activity. More preferably, the co-solvent is dimethyl sulfoxide.

Thus, the present invention is directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent, wherein the co-solvent for solubilizing guanosine is dimethyl sulfoxide.

Thus, the present invention is directed to a method for producing guanosine 5'-diphospho-β-L-fucose from guanosine and D-mannose comprising A) providing a solution comprising
  (i) guanosine and D-mannose;
  (ii) polyphosphate, adenosine triphosphate and a co-solvent for solubilizing guanosine; and
  providing a set of enzymes comprising a guanosine kinase, a polyphosphate kinase and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent by wherein the co-solvent for solubilizing guanosine is dimethyl sulfoxide.

DETAILED DESCRIPTION OF THE INVENTION

Definitions

As used herein, the term "polyphosphate" refers to any salts containing several P—O—P bonds generated by corner sharing of six or more phosphate ($PO_4$) tetrahedral, leading to the formation of long chains. The term "$PolyP_n$" is synonymously used, wherein n represents average chain length of the number of phosphate residues, e.g. $PolyP_{25}$ refers to a polyphosphate having about 25 phosphate residues and $PolyP_{14}$ refers to a polyphosphate having about 14 phosphate residues.

As used herein, the term "guanosine kinase" or "inosine kinase" refers to a polypeptide having guanosine kinase activity, i.e. a guanosine kinase catalyzes the reaction of guanosine to guanosine 5'-monophosphate in the presence of adenosine triphosphate. The guanosine kinase belongs to the EC class 2.7.1.73.

As used herein, the term "polyphosphate kinase" refers to a polypeptide having polyphosphate kinase activity, i.e. a polyphosphate kinase catalyzes the following reactions:

ADP+polyphosphate (n+1) ⇌ ATP+polyphosphate(n)

NMP+polyphosphate (n+1) ⇌ NDP+polyphosphate(n)

NDP+polyphosphate (n+1) ⇌ NTP+polyphosphate(n)

with N being a nucleotide such as guanosine, adenosine, uridine etc. and NMP being nucleoside monophosphate, NDP being nucleoside diphosphate and NTP being nucleoside triphosphate.

In case of guanosine the polyphosphate kinase catalyzes the following reactions:

ADP+polyphosphate (n+1) ⇌ ATP+polyphosphate(n)

GMP+polyphosphate (n+1) ⇌ GDP+polyphosphate (n)

GDP+polyphosphate (n+1) ⇌ GTP+polyphosphate(n)

The polyphosphate kinase belongs to the EC class 2.7.4.1. Representatives of the polyphosphate kinase enzyme used in the inventive methods described herein include but are not limited to polyphosphate kinase 1 (PPK1), polyphosphate kinase 2 (PPK2), 2-domain polyphosphate kinase 2 (2D-PPK2) 1-domain polyphosphate kinase 2 (1D-PPK2), polyphosphate kinase 3 (PPK3) and guanylate kinase (EC class 2.7.4.8).

As used herein, the term "L-fucokinase/L-fucose-1-phosphate guanylyl-transferase" refers to a bifunctional polypeptide having L-fucokinase activity and L-fucose-1-phosphate guanylyltransferase activity, i.e. a polypeptide that catalyzes the following reactions:

Fuc+ATP ⇌ Fuc-1-P+ADP

Fuc-1-P+GTP ⇌ GDP-Fuc+PPi

The L-fucokinase/L-fucose-1-phosphate guanylyltransferase belongs to EC classes 2.7.1.52 and 2.7.7.30.

It should be clear that also two separate functional polypeptides, one having L-fucokinase activity and the other having L-fucose-1-phosphate guanylyltransferase activity may be suitable for the method of the present invention.

As used herein, the term "pyrophosphatase" refers to a polypeptide having pyrophosphatase activity, i.e. a polypeptide that catalyzes the following reaction:

$$PPi + H_2O \rightleftharpoons 2\ Pi$$

wherein PPi refers to pyrophosphate and Pi to phosphate.

The pyrophosphatase belongs to EC class 3.6.1.1.

As used herein, the term "glucokinase" refers to a polypeptide having kinase activity, i.e. a kinase that catalyzes the following reactions:

$$Man + ATP \rightleftharpoons Man\text{-}6\text{-}P + ADP$$

The glucokinase belongs to the EC class 2.7.1.1.

As used herein, the term "phosphomannomutase" refers to a polypeptide having phosphomannomutase activity, i.e. a phosphomannomutase that catalyzes the following reactions:

$$Man\text{-}6\text{-}P \rightleftharpoons Man\text{-}1\text{-}P$$

The phosphomannomutase belongs to the EC class 5.4.2.8.

As used herein, the term "N-acetylhexosamine-1-kinase" refers to polypeptide having kinase activity, i.e. a polypeptide that catalyzes the following reactions:

$$Man + ATP \rightleftharpoons Man\text{-}1\text{-}P + ADP$$

The N-acetylhexosamine-1-kinase belongs to the EC class 2.7.1.162.

As used herein, the term "mannose-1-phosphate guanylyltransferase" refers to a polypeptide having a D-mannose-1-phosphate guanylyltransferase activity, i.e. a polypeptide that catalyzes the following reactions:

$$Man\text{-}1\text{-}P + GTP \rightleftharpoons GDP\text{-}Man + PPi$$

The mannose-1-phosphate guanylyltransferase belongs to the EC class 2.7.7.13.

As used herein, the term "GDP-mannose 4,6-dehydratase" refers to a polypeptide having GDP-mannose 4,6-dehydratase activity, i.e. a polypeptide that catalyzes the following reactions:

$$GDP\text{-}Man \rightleftharpoons GDP\text{-}4\text{-}dehydro\text{-}6\text{-}deoxy\text{-}alpha\text{-}D\text{-}mannose$$

The GDP-mannose 4,6-dehydratase belongs to the EC class 4.2.1.47.

As used herein, the term "GDP-L-fucose synthase" refers to a polypeptide having GDP-L-fucose synthase activity, i.e. a polypeptide that catalyzes the following reactions:

$$GDP\text{-}4\text{-}dehydro\text{-}6\text{-}deoxy\text{-}alpha\text{-}D\text{-}mannose + NADPH \rightleftharpoons GDP\text{-}Fuc + NADP^+$$

The GDP-L-fucose synthase belongs to the EC class 1.1.1.271 and has the following synonyms and abbreviations GDP-4-keto-6-deoxymannose-3,5-epimerase-4-reductase (WCAG), GDP-4-keto-6-deoxy-D-mannose epimerase-reductase, GDP-4-keto-6-deoxy-D-mannose epimerase/reductase, GDPFuc synthase, GER, GFS, GMER, guanosine diphosphofucose synthetase.

As used herein, the term "co-solvent" refers to an organic compound or a mixture of organic compounds, particularly an organic solvent or a mixture of different solvents, that increases or enhances the solubility of guanosine in water. The person skilled in the art may readily envision that a suitable co-solvent is a solvent in which guanosine has a high solubility, including methanol, ethanol, isopropanol, n-propanol, isobutanol, n-butanol, tert-butanol, acetonitrile, acetone or dimethyl sulfoxide. Preferably the co-solvent is a polar aprotic solvent, such as dimethyl sulfoxide or dimethylformamide. Particularly preferred the co-solvent is dimethyl sulfoxide.

As used herein, "saccharide" refers to but not restricted to monosaccharide, disaccharide, trisaccharide, tetrasaccharide, pentasaccharide, hexasaccharide, heptasaccharide, octasaccharide . . . , oligosaccharide, glycan and polysaccharide. The saccharide comprises preferably monosaccharide units selected from: D-Arabinose, D-Lyxose, D-Ribose, D-Xylose, L-Arabinose, L-Lyxose, L-Ribose, L-Xylose, D-Ribulose, D-Xylulose, L-Ribulose, L-Xylulose, D-Deoxyribose, L-Deoxyribose, D-Erythrose, D-Threose, L-glycero-D-manno-Heptose, D-glycero-D-manno-Heptose, D-Allose, D-Altrose, D-Glucose, D-Mannose, D-Gulose, D-Idose, D-Galactose, D-Talose, D-psicose, D-fructose, D-sorbose, D-tagatose, 6-Deoxy-L-altrose, 6-Deoxy-D-talose, D-Fucose, L-Fucose, D-Rhamnose, L-Rhamnose, D-Quinovose, Olivose, Tyvelose, Ascarylose, Abequose, Paratose, Digitoxose, Colitose, D-Glucosamine, D-Galactosamine, D-Mannosamine, D-Allosamine, I-Altrosamine, D-Gulosamine, L-Idosamine, D-Talosamine, N-Acetyl-d-glucosamine, N-Acetyl-D-galactosamine, N-Acetyl-D-mannosamine, N-Acetyl-D-allosamine, N-Acetyl-L-altrosamine, N-Acetyl-D-gulosamine, N-Acetyl-L-idosamine, N-Acetyl-D-talosamine, N-Acetyl-D-fucosamine, N-Acetyl-L-fucosamine, N-Acetyl-L-rhamnosamine, N-Acetyl-D-quinovosamine, D-Glucuronic acid, D-Galacturonic acid, D-Mannuronic acid, D-Alluronic acid, L-Altruronic acid, D-Guluronic acid, L-Guluronic acid, L-Iduronic acid, D-Taluronic acid, Neuraminic acid, N-Acetylneuraminic acid, N-Glycolylneuraminic acid, Apiose, Bacillosamine, Thevetose, Acofriose, Cymarose, Muramic acid, N-Acetylmuramic acid, N-Glycolylmuramic acid, 3-Deoxy-lyxo-heptulosaric acid, Ketodeoxyoctonic acid, and Ketodeoxynononic acid. Preferably the monosaccharide units belong to the following group of α- and β-D/L-carbohydrates comprising or consisting of:

α-D-ribopyranose, α-D-arabinopyranose, α-D-xylopyranose, α-D-lyxopyranose, α-D-allopyranose, α-D-altropyranose, α-D-glucopyranose, α-D-mannpyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-glucopyranuronic acid, β-D-ribopyranose, β-D-arabinopyranose, β-D-xylopyranose, β-D-lyxopyranose, β-D-allopyranose, β-D-altropyranose, β-D-glucopyranose, β-D-mannpyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, and β-L-rhamnopyranose.

The saccharides are further optionally modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

As used herein, the term "glycopeptide" refers to a peptide that contains carbohydrate moieties covalently attached to the side chains of the amino acid residues that constitute the peptide. The carbohydrate moieties form side chains and are either O-glycosidic connected to the hydroxy group of a serine or threonine residue or N-glycosidic connected to the amido nitrogen of an asparagine residue.

As used herein, the term "glycoprotein" refers to a polypeptide that contains carbohydrate moieties covalently attached to the side chains of the amino acid residues that constitute the polypeptide. The carbohydrate moieties form side chains and are either O-glycosidic connected to the hydroxy group of a serine or threonine residue or N-glycosidic connected to the amido nitrogen of an asparagine residue.

As used herein, the term "protein" refers to a polypeptide that contains or lacks of carbohydrate moieties covalently attached to the side chains of the amino acid residues that constitute the polypeptide including aglycosylated proteins and glycosylated proteins.

As used herein, the term "peptide" refers to a peptide that contains or lacks of carbohydrate moieties covalently attached to the side chains of the amino acid residues that constitute the peptide, including aglycosylated peptides and glycosylated peptides.

Co-Factor Regeneration

The GDP-L-fucose synthase consumes the cofactor NADPH in the formation of GDP-fucose from GDP-4-dehydro-6-deoxy-a-D-mannose. Thus, in the inventive methods described herein, although not explicitly stated, GDP-fucose is produced from guanosine and D-mannose in the presence of the cofactor NADPH.

Since the co-factors NADPH and NADP⁺ are very expensive, it is advantageous if they are regenerated in the system in order to keep them at catalytic amount and develop a cost effective process.

The enzymes that can be used for regeneration of NADPH are:

Phosphite dehydrogenase EC number 1.20.1.1:

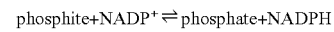

Glucose dehydrogenase EC number 1.1.1.47 or 1.1.1.118:

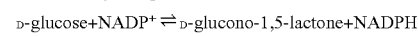

Glycerol dehydrogenase EC number 1.1.1.72:

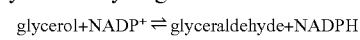

Glucose-6-phosphate-dehydrogenase (G6PDH) EC number 1.1.1.49:

Glutamate dehydrogenase (GLDH) EC number 1.4.1.4:

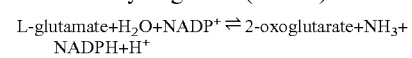

Thus in a preferred embodiment the set of enzymes further includes one of the above listed enzymes that can be used for NADPH regeneration, i.e. a phosphite dehydrogenase, a glycerol dehydrogenase, a glucose dehydrogenase, a glucose-6-phosphate dehydrogenase or a glutamate dehydrogenase. More preferably, the set of enzymes further includes an enzyme selected from a glucose dehydrogenase, a glucose-6-phosphate dehydrogenase and a glutamate dehydrogenase.

Thus the present invention is directed to a method for producing guanosine 5'-diphospho-β-L-fucose from guanosine and L-fucose or D-mannose comprising the following steps:

A) providing a solution comprising
  (i) guanosine and L-fucose or guanosine and D-mannose
  (ii) polyphosphate, adenosine triphosphate a co-solvent for solubilizing guanosine and in case of D-mannose NAPDH; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase; and any of a phosphite dehydrogenase, a glucose dehydrogenase, a glucose-6-phosphate-dehydrogenase and glutamate dehydrogenase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate, NAPDH and the co-solvent.

In a preferred embodiment, the method for producing guanosine 5'-diphospho-β-L-fucose from guanosine and D-mannose comprising the following steps:

A) providing a solution comprising
  (i) guanosine and D-mannose
  (ii) polyphosphate, adenosine triphosphate, NADPH and a co-solvent for solubilizing guanosine; and
  providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase; and an enzyme selected from a phosphite dehydrogenase, a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate, NADPH and the co-solvent.

In a particularly preferred embodiment, the method for producing guanosine 5'-diphospho-β-L-fucose from guanosine and D-mannose comprising the following steps:
A) providing a solution comprising
(i) guanosine and D-mannose
(ii) polyphosphate, adenosine triphosphate, NADPH, L-glutamate and a co-solvent for solubilizing guanosine; and
providing a set of enzymes comprising a guanosine kinase, a polyphosphate kinase, a glutamate dehydrogenase and either (a) a glucokinase, phosphomanno-mutase, a mannose-1-phosphate guanylyltransferase, a GDP-mannose-4,6-dehydratase and a GDP-L-fucose-synthase or (b) an N-acetyl-hexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate, NADPH, L-glutamate and the co-solvent.

In a particularly preferred embodiment, the method for producing guanosine 5'-diphospho-β-L-fucose from guanosine and D-mannose comprising the following steps:
A) providing a solution comprising
(i) guanosine and D-mannose
(ii) polyphosphate, adenosine triphosphate, NADPH, D-glucose and a co-solvent for solubilizing guanosine; and
providing a set of enzymes comprising a guanosine kinase, a polyphosphate kinase, a glucose-6-phosphate dehydrogenase and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate, NADPH, D-glucose and the co-solvent.

The term "solid support" as used herein refers to an insoluble, functionalized, material to which enzymes or other reagents may be attached or immobilized, directly or via a linker bearing an anchoring group, allowing enzymes to be readily separated (by washing, filtration, centrifugation, etc.) from excess reagents, soluble reaction products, by-products, or solvents. A solid support can be composed of organic polymers such as polystyrene, polyethylene, polypropylene, polyfluoro-ethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. A solid support can also consist of magnetic particles. For an overview of suitable support materials for enzyme immobilization see Zdarta et al. *Catalysts* 2018, 8, 92, and Datta et al. *Biotech* 2013 3:1-9.

The configuration of a solid support can be in the form of beads, monoliths, spheres, particles, a particle bed, a fiber mat, granules, a gel, a membrane, a hollow-fiber membrane, a mixed-matrix membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

Surprisingly, the inventors have found that by solubilizing guanosine in a co-solvent, such as dimethyl sulfoxide, a nearly complete conversion of guanosine to GDP-fucose was achieved after already three hours (Example 2). Also, the co-solvent did not affect the activity of the enzymes used in the preparation of GDP-fucose. As a co-solvent any compound is suitable that increases or enhances the solubility of guanosine in water or buffer.

Preferably, the co-solvent is an organic solvent selected from the group comprising: methanol, ethanol, isopropanol, n-propanol, isobutanol, n-butanol, tert-butanol, acetonitrile, acetone and dimethyl sulfoxide. Preferably the co-solvent is a polar aprotic solvent such as dimethyl sulfoxide or dimethylformamide. More preferably, the co-solvent is dimethyl sulfoxide. Thus, the present invention is directed to a method for producing guanosine 5'-diphospho-β-L-fucose from guanosine and L-fucose or guanosine and D-mannose comprising the following steps:
A) providing a solution comprising
(i) guanosine and L-fucose or guanosine and D-mannose
(ii) polyphosphate, adenosine triphosphate and a co-solvent for solubilizing guanosine; and
providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the co-solvent for solubilizing guanosine is selected from the group comprising methanol, ethanol, isopropanol, n-propanol, isobutanol, n-butanol, tert-butanol, acetonitrile, acetone and dimethyl sulfoxide.

Preferably, the co-solvent is an organic solvent selected from the group comprising: methanol, ethanol, isopropanol, n-propanol, isobutanol, n-butanol, tert-butanol, acetonitrile, acetone and dimethyl sulfoxide. More preferably, the co-solvent is dimethyl sulfoxide. Thus, the present invention is directed to a method for producing guanosine 5'-diphospho-β-L-fucose from guanosine and L-fucose comprising the following steps:
A) providing a solution comprising
(i) guanosine and L-fucose,
(ii) polyphosphate, adenosine triphosphate and a co-solvent for solubilizing guanosine; and providing a set of enzymes comprising a guanosine kinase, a polyphosphate kinase, a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent, wherein the co-solvent for solubilizing guanosine is selected from the group comprising: methanol, ethanol, isopropanol, n-propanol, isobutanol, n-butanol, tert-butanol, acetonitrile, acetone and dimethyl sulfoxide.

Preferably, the amount of co-solvent for solubilizing guanosine is kept as a low as possible to enable the solubilization of guanosine. Thus, preferably the amount of co-solvent is sufficient to solubilize guanosine completely in the solution provided in step A) of the inventive methods described herein. Alternatively, the amount of co-solvent is sufficient to solubilize at least half of the amount of guanosine in the solution provided in step A) of the inventive methods described herein.

Further, the amount of co-solvent is between 0.01 vol % to 30 vol % based on total volume of the solution provided in step A). More preferably, the amount of co-solvent is between 0.05 vol % to 25 vol % based on total volume of the solution provided in step A). Even more preferably, the amount of co-solvent is between 0.1 vol % to 15 vol % based on total volume of the solution provided in step A). More preferably, the amount of co-solvent is between 0.1 vol % to 10 vol % based on total volume of the solution provided in step A). Most preferably, the amount of co-solvent is between 1 vol % to 5 vol % based on total volume of the solution provided in step A).

Thus, the present invention is directed to a method for producing guanosine 5'-diphospho-β-L-fucose from guanosine and L-fucose or guanosine and D-mannose comprising the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the amount of co-solvent for solubilizing guanosine is between 1 vol % to 5 vol % based on total volume of the solution provided in step A).

Thus, the present invention is directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent, wherein the amount of co-solvent for solubilizing guanosine is between 1 vol % to 5 vol % based on total volume of the solution provided in step A).

In one embodiment the method for producing guanosine 5'-diphospho-β-L-fucose from guanosine and L-fucose or guanosine and D-mannose comprising the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the co-solvent is dimethyl sulfoxide and the amount of co-solvent is between 1 vol % to 5 vol % based on total volume of the solution provided in step A).

In one embodiment, the method for producing guanosine 5'-diphospho-β-L-fucose from guanosine and L-fucose comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent, wherein the co-solvent is dimethyl sulfoxide and the amount of co-solvent is between 1 vol % to 5 vol % based on total volume of the solution provided in step A).

With the increased solubility, higher concentrated reaction mixtures can be realized, thereby reducing process costs. Thus, the concentration of guanosine and L-fucose in the solution provided in step A) is preferably in the range of 0.01 mM to 100,000 mM. More preferably, the concentration of guanosine and L-fucose is preferably in the range of 0.05 mM to 50,000 mM. More preferably, the concentration of guanosine and L-fucose is preferably in the range of 0.1 mM to 10,000 mM. More preferably, the concentration of guanosine and L-fucose is preferably in the range of 0.2 mM to 5,000 mM.

Thus, the present invention is directed to a method for producing guanosine 5'-diphospho-β-L-fucose from guanosine and L-fucose comprising the following steps:

A) providing a solution comprising
   (i) guanosine and L-fucose,
   (ii) polyphosphate, adenosine triphosphate and a co-solvent for solubilizing guanosine; and
   providing a set of enzymes comprising a guanosine kinase, a polyphosphate kinase, a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent,
wherein the concentration of guanosine and L-fucose in the solution provided in step A) is in the range of 0.2 mM to 5,000 mM.

With the increased solubility, higher concentrated reaction mixtures can be realized, thereby reducing process costs. Thus, the concentration of guanosine and D-mannose in the solution provided in step A) is preferably in the range of 0.01 mM to 100,000 mM. More preferably, the concentration of guanosine and D-mannose is preferably in the range of 0.05 mM to 50,000 mM. More preferably, the concentration of guanosine and D-mannose is preferably in the range of 0.1 mM to 10,000 mM. More preferably, the concentration of guanosine and D-mannose is preferably in the range of 0.2 mM to 5,000 mM.

Thus, the present invention is directed to a method for producing guanosine 5'-diphospho-β-L-fucose from guanosine and D-mannose comprising the following steps:
A) providing a solution comprising
   (i) guanosine and D-mannose
   (ii) polyphosphate, adenosine triphosphate and a co-solvent for solubilizing guanosine; and
   providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
wherein the concentration of guanosine and D-mannose in the solution provided in step A) is in the range of 0.2 mM to 5,000 mM.

Preferably, the concentration of the enzymes in the set of enzymes is between 0.0001 mg/mL and 100 mg/mL based on the total volume of the solution provided in step A).

As a side product in the reaction of fucose-1-phosphate with guanosine triphosphate to GDP-fucose as well as in the in the reaction of mannose-1-phosphate with guanosine triphosphate to GDP-mannose, pyrophosphate (PPi) is formed. Although pyrophosphate is unstable in aqueous solution, it only slowly hydrolyzes into inorganic phosphate (Pi). A high concentration of pyrophosphate may also lower the activity of the L-fucokinase/L-fucose-1-phosphate guanylyltransferase and mannose-1-phosphate guanylyltransferase enzyme involved in the GDP-fucose formation. The enzyme pyrophosphatase is able to catalyze the hydrolysis of pyrophosphate to phosphate, thereby effectively rendering the GDP-fucose/GDP-mannose formation irreversible. Thus, in a preferred embodiment of the present invention the set of enzymes further comprises a pyrophosphatase.

The method for producing guanosine 5'-diphospho-β-L-fucose from guanosine and L-fucose or guanosine and D-mannose comprising the following steps:
A) providing a solution comprising
   (i) guanosine and L-fucose or guanosine and D-mannose
   (ii) polyphosphate, adenosine triphosphate and a co-solvent for solubilizing guanosine; and
   providing a set of enzymes comprising a guanosine kinase, a polyphosphate kinase and a pyrophosphatase, and in case of L-fucose a L-fucokinase/L-fucose-1-phosphate guanylyltransferase or in case of D-mannose either (a) a glucokinase, phosphomannomutase, a mannose-1-phosphate guanylyl-transferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent.

The present invention is directed to a method for producing guanosine 5'-diphospho-β-L-fucose from guanosine and L-fucose comprising the following steps:
A) providing a solution comprising
   (i) guanosine and L-fucose,
   (ii) polyphosphate, adenosine triphosphate and a co-solvent for solubilizing guanosine; and
   providing a set of enzymes comprising a guanosine kinase, a polyphosphate kinase, a L-fucokinase/L-fucose-1-phosphate guanylyltransferase, and a pyrophosphatase;
B) producing guanosine 5'-diphospho-β-L-fucose from guanosine and fucose in the presence of the set of enzymes, polyphosphate, adenosine triphosphate and the co-solvent.

Reworded, the inventive method for producing guanosine 5'-diphospho-β-L-fucose from guanosine and L-fucose comprises the following steps:
A) providing a solution comprising
   (i) guanosine and L-fucose;
   (ii) polyphosphate, adenosine triphosphate and a co-solvent for solubilizing guanosine; and
   providing a set of enzymes comprising a guanosine kinase, a polyphosphate kinase, a L-fucokinase/L-fucose-1-phosphate guanylyltransferase, and a pyrophosphatase;
B) producing guanosine 5'-diphospho-β-L-fucose from guanosine and fucose in the presence of the set of enzymes, polyphosphate, adenosine triphosphate and the co-solvent by
   (a) forming fucose-1-phosphate from L-fucose and adenosine triphosphate being catalyzed by a L-fucokinase/L-fucose-1-phosphate guanylyl-transferase,
   (b1) forming guanosine monophosphate from guanosine and adenosine triphosphate being catalyzed by a guanosine kinase;
   (b2') forming guanosine diphosphate from guanosine monophosphate and polyphosphate being catalyzed by a polyphosphate kinase
   (b2") forming guanosine triphosphate from guanosine diphosphate and polyphosphate being catalyzed by a polyphosphate kinase, (c') reacting fucose-1-phosphate with guanosine triphosphate to GDP-fucose and pyrophosphate in the presence of a L-fucokinase/L-fucose-1-phosphate guanylyltransferase; and
(c") converting pyrophosphate to phosphate in the presence of a pyrophosphatase.

Thus, the present invention is directed to a method for producing guanosine 5'-diphospho-β-L-fucose from guanosine and D-mannose comprising the following steps:
A) providing a solution comprising
(i) guanosine and D-mannose;
(ii) polyphosphate, adenosine triphosphate and a co-solvent for solubilizing guanosine; and
providing a set of enzymes comprising a guanosine kinase, a polyphosphate kinase and either (a) a glucokinase, phosphomannomutase, a mannose-1-phosphate guanylyltransferase, a GDP-mannose-4,6-dehydratase and a GDP-L-fucose-synthase and a pyrophosphatase or (b) an N-acetylhexosamine-1-kinase, a mannose-1-phosphate guanylyltransferase, a GDP-mannose 4,6-dehydratase and a GDP-L-fucose-synthase and a pyrophosphatase;
B) producing guanosine 5'-diphospho-β-L-fucose from guanosine and D-mannose in the presence of the set of enzymes, polyphosphate, adenosine triphosphate and the co-solvent by
(a) forming mannose-1-phosphate (Man-1-P) from D-mannose and adenosine triphosphate being catalyzed by a N-acetylhexosamine-1-kinase
or
forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase
(b1) forming guanosine monophosphate (GMP) from guanosine and adenosine triphosphate being catalyzed by a guanosine kinase;
(b2') forming guanosine diphosphate (GDP) from guanosine monophosphate and polyphosphate being catalyzed by a polyphosphate kinase
(b2") forming guanosine triphosphate (GTP) from guanosine diphosphate and polyphosphate being catalyzed by a polyphosphate kinase; and
(c') reacting mannose-1-phosphate with guanosine triphosphate to GDP-mannose and pyrophosphate in the presence of a D-mannose-1-phosphate guanylyl-transferase
(c") converting pyrophosphate to phosphate in the presence of a pyrophosphatase.
(d) forming GDP-4-dehydro-6-deoxy-alpha-D-mannose from GDP-mannose being catalyzed by GDP-mannose-4,6-dehydratase; and
(e) forming GDP-fucose from GDP-4-dehydro-6-deoxy-alpha-D-mannose and
NADPH being catalyzed by GDP-L-fucose synthase.

Preferably, the inventive method for producing guanosine 5'-diphospho-β-L-fucose from guanosine and L-fucose or guanosine and D-mannose comprising the following steps:
A) providing a solution comprising
(i) guanosine and L-fucose or guanosine and D-mannose
(ii) polyphosphate, adenosine triphosphate and a co-solvent for solubilizing guanosine; and
providing a set of enzymes comprising a guanosine kinase, a polyphosphate kinase and a pyrophosphatase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the co-solvent is dimethyl sulfoxide.

Preferably, the inventive method for producing guanosine 5'-diphospho-β-L-fucose from guanosine and L-fucose comprises the following steps:
A) providing a solution comprising
(i) guanosine and L-fucose;
(ii) polyphosphate, adenosine triphosphate and a co-solvent for solubilizing guanosine; and
providing a set of enzymes comprising a guanosine kinase, a polyphosphate kinase, a L-fucokinase/L-fucose-1-phosphate guanylyltransferase, and a pyrophosphatase;
B) producing guanosine 5'-diphospho-β-L-fucose from guanosine and fucose in the presence of the set of enzymes, polyphosphate, adenosine triphosphate and the co-solvent,
wherein the co-solvent is dimethyl sulfoxide.

Preferably, the pyrophosphatase used in the inventive methods described herein is an inorganic pyrophosphatase. Preferably, the pyrophosphatase is an inorganic pyrophosphatase from *Pasteurella multocida* (PmPpA).

Polyphosphate is able to form stable, water-soluble complexes with metal ions (e.g. $Ca^{2+}$, $Mg^{2+}$, $Fe2^{+/3+}$) which were initially dissolved in aqueous media. This effect is called sequestration and prevents the bound metal ions from participating in reactions, particularly enzymatic reactions. Therefore, the sequestered metal ions, particularly $Mg^{2+}$ and $Mn^{2+}$, cannot act as co-factor for the enzymes involved in the inventive methods described herein. As the ability of a particular polyphosphate to sequester a particular metal ion decreases with increasing chain length of the polyphosphate, long-chain polyphosphates are preferred in the present invention. More preferred are polyphosphates having at least 14 phosphate residues. Most preferred are polyphosphates having at least 25 phosphate residues.

Thus, the present invention is directed to a method for producing guanosine 5'-diphospho-β-L-fucose from guanosine and L-fucose or guanosine and D-mannose comprising the following steps:
A) providing a solution comprising
(i) guanosine and L-fucose or guanosine and D-mannose
(ii) polyphosphate, adenosine triphosphate and a co-solvent for solubilizing guanosine; and
providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the polyphosphate is a long-chain polyphosphate having at least 25 phosphate residues.

Thus, the present invention is directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent;

wherein the polyphosphate is a long-chain polyphosphate having at least 25 phosphate residues Preferably, the method for producing guanosine 5'-diphospho-β-L-fucose from guanosine and L-fucose or guanosine and D-mannose comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the polyphosphate is a long-chain polyphosphate having at least 25 phosphate residues and the co-solvent is dimethyl sulfoxide.

Preferably, the method for producing guanosine 5'-diphospho-β-L-fucose from guanosine and L-fucose comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a L-fucokinase/L-fucose-1-phosphate guanylyltransferase, and optionally a pyrophosphatase;
B) producing guanosine 5'-diphospho-β-L-fucose from guanosine and fucose in the presence of the set of enzymes, polyphosphate, adenosine triphosphate and the co-solvent, wherein the polyphosphate is a long-chain polyphosphate having at least 25 phosphate residues and the co-solvent is dimethyl sulfoxide.

Preferably, the enzymes are present in a single reaction mixture with the other substrates. The mixture may be homogenous (solution) or heterogeneous. The enzymes may be immobilized on a solid support or not. Thus, the guanosine 5'-diphospho-β-L-fucose is produced in a single reaction mixture according to a further aspect of the inventive method.

Thus, the method for producing guanosine 5'-diphospho-β-L-fucose from guanosine and L-fucose or guanosine and D-mannose comprises the following steps:

A) providing a mixture comprising
  (i) guanosine and L-fucose or guanosine and D-mannose
  (ii) polyphosphate, adenosine triphosphate and a co-solvent for solubilizing guanosine; and
  (iii) a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent.

Thus, the method for producing guanosine 5'-diphospho-β-L-fucose from guanosine and L-fucose or guanosine and D-mannose comprises the following steps:

A) providing a mixture comprising
  (i) guanosine and L-fucose or guanosine and D-mannose
  (ii) polyphosphate, adenosine triphosphate, a co-solvent for solubilizing guanosine and in case of D-mannose NADPH; and
  (iii) a set of enzymes comprising a guanosine kinase, a polyphosphate kinase, and in case of L-fucose a L-fucokinase/L-fucose-1-phosphate guanylyl-transferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate, NADPH and the co-solvent.

Thus, the method for producing guanosine 5'-diphospho-β-L-fucose from guanosine and L-fucose comprises the following steps:

A) providing a mixture comprising
  (i) guanosine and L-fucose;
  (ii) polyphosphate, adenosine triphosphate and a co-solvent for solubilizing guanosine; and
  (iii) a set of enzymes comprising a guanosine kinase, a polyphosphate kinase, and a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent.

Also, the method for producing guanosine 5'-diphospho-β-L-fucose from guanosine and L-fucose comprises the following steps:
A) providing a solution comprising
  (i) guanosine and L-fucose;
  (ii) polyphosphate, adenosine triphosphate and a co-solvent for solubilizing guanosine; and
  (iii) a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent.

Reworded, the method for producing guanosine 5'-diphospho-β-L-fucose from guanosine and L-fucose comprises the following steps:
A) providing a mixture comprising
  (i) guanosine and L-fucose;
  (ii) polyphosphate, adenosine triphosphate and a co-solvent for solubilizing guanosine; and
  (iii) at least three enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the at least three enzymes, polyphosphate, adenosine triphosphate and the co-solvent.

Preferably, the method for producing guanosine 5'-diphospho-β-L-fucose from guanosine and L-fucose or guanosine and D-mannose comprises the following steps:
A) providing a solution comprising
  (i) guanosine and L-fucose or guanosine and D-mannose
  (ii) polyphosphate, adenosine triphosphate and a co-solvent for solubilizing guanosine; and
  (iii) a set of enzymes comprising a guanosine kinase, a polyphosphate kinase, optionally a pyrophosphatase, and either (a) a glucokinase, a phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
wherein the co-solvent is dimethyl sulfoxide.

Preferably, the method for producing guanosine 5'-diphospho-β-L-fucose from guanosine and L-fucose comprises the following steps:
A) providing a solution comprising
  (i) guanosine and L-fucose;
  (ii) polyphosphate, adenosine triphosphate and a co-solvent for solubilizing guanosine; and
  (iii) a set of enzymes comprising a guanosine kinase, a polyphosphate kinase, a L-fucokinase/L-fucose-1-phosphate guanylyltransferase, and optionally a pyrophosphatase;
B) producing guanosine 5'-diphospho-β-L-fucose from guanosine and fucose in the presence of the set of enzymes, polyphosphate, adenosine triphosphate and the co-solvent;
wherein the co-solvent is dimethyl sulfoxide.

The synthesis of GDP-fucose from guanosine and D-mannose requires NADPH. The cascade is particularly economical if expensive NADPH is recycled in the cascade. Additionally, the reaction equilibrium can be driven towards GDP-fucose by continuous recycling of NADPH from NADP+.

Any of the following enzymes can be applied for recycling of NADPH from NADP+: a phosphite dehydrogenase, a glycerol dehydrogenase, a glucose dehydrogenase (GlcDH), a glucose-6-phosphate dehydrogenase (G6PDH) and a glutamate dehydrogenase (GLDH).

Thus, in a preferred embodiment the set of enzymes further includes any of a glucose dehydrogenase, a glucose-6-phosphate dehydrogenase and a glutamate dehydrogenase.

The present invention is directed to a method for producing guanosine 5'-diphospho-β-L-fucose from guanosine and D-mannose comprising the following steps:
A) providing a solution comprising
  (i) guanosine and D-mannose (ii) polyphosphate, adenosine triphosphate and a co-solvent for solubilizing guanosine; and
  providing a set of enzymes comprising a guanosine kinase, a polyphosphate kinase and either
    (a) a glucokinase, a phosphomannomutase, a mannose-1-phosphate guanylyltransferase, a GDP-mannose-4,6-dehydratase and a GDP-L-fucose-synthase and an enzyme selected from a glucose dehydrogenase, a glucose-6-phosphate-dehydrogenase and glutamate dehydrogenase; or
    (b) an N-acetylhexosamine-1-kinase, a mannose-1-phosphate guanylyltransferase, a GDP-mannose 4,6-dehydratase and a GDP-L-fucose-synthase, and an enzyme selected from a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate and the co-solvent, preferably the co-solvent is dimethyl sulfoxide.

Thus, the present invention is directed to a method for producing guanosine 5'-diphospho-β-L-fucose from guanosine and D-mannose comprising the following steps:
A) providing a solution comprising
  (i) guanosine and D-mannose
  (ii) polyphosphate, adenosine triphosphate, NADPH and a co-solvent for solubilizing guanosine; and
  providing a set of enzymes comprising a guanosine kinase, a polyphosphate kinase and either
    (a) a glucokinase, a phosphomannomutase, a mannose-1-phosphate guanylyltransferase, a GDP-mannose-4,6-dehydratase and a GDP-L-fucose-synthase and any of a glucose dehydrogenase, a glucose-6-phosphate-dehydrogenase and glutamate dehydrogenase; or
    (b) an N-acetylhexosamine-1-kinase, a mannose-1-phosphate guanylyltransferase, a GDP-mannose 4,6-dehydratase and a GDP-L-fucose-synthase, and any of a glucose dehydrogenase, a glucose-6-phosphate-dehydrogenase and glutamate dehydrogenase;

B) producing guanosine 5'-diphospho-β-L-fucose from guanosine and D-mannose in the presence of the set of enzymes, polyphosphate, adenosine triphosphate and the co-solvent, preferably dimethyl sulfoxide by
  (a) forming mannose-1-phosphate (Man-1-P) from D-mannose and adenosine triphosphate being catalyzed by a N-acetylhexosamine-1-kinase
    or
    forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase;
  (b1) forming guanosine monophosphate (GMP) from guanosine and adenosine triphosphate being catalyzed by a guanosine kinase;
  (b2') forming guanosine diphosphate (GDP) from guanosine monophosphate and polyphosphate being catalyzed by a polyphosphate kinase;
  (b2") forming guanosine triphosphate (GTP) from guanosine diphosphate and polyphosphate being catalyzed by a polyphosphate kinase;
  (c') reacting mannose-1-phosphate with guanosine triphosphate to GDP-mannose and pyrophosphate in the presence of a D-mannose-1-phosphate guanylyl-transferase
  (d) forming GDP-4-dehydro-6-deoxy-alpha-D-mannose from GDP-mannose being catalyzed by GDP-mannose-4,6-dehydratase;
  (e) forming GDP-fucose from GDP-4-dehydro-6-deoxy-alpha-D-mannose and NADPH being catalyzed by GDP-L-fucose synthase; and
  (f) regenerating NADPH from NADP+ being catalyzed by any of a glucose dehydrogenase, a glucose-6-phosphate-dehydrogenase and glutamate dehydrogenase.

Preferred, the present invention is directed to a method for producing guanosine 5'-diphospho-β-L-fucose from guanosine and D-mannose comprising the following steps:
A) providing a solution comprising
  (i) guanosine and D-mannose
  (ii) polyphosphate, adenosine triphosphate and a co-solvent for solubilizing guanosine; and
  providing a set of enzymes comprising a guanosine kinase, a polyphosphate kinase and either
    (a) a glucokinase, a phosphomannomutase, a mannose-1-phosphate guanylyltransferase, a GDP-mannose-4,6-dehydratase and a GDP-L-fucose-synthase, a pyrophosphatase and any of a glucose dehydrogenase, a glucose-6-phosphate-dehydrogenase and glutamate dehydrogenase; or
    (b) an N-acetylhexosamine-1-kinase, a mannose-1-phosphate guanylyltransferase, a GDP-mannose 4,6-dehydratase and a GDP-L-fucose-synthase, a pyrophosphatase, and any of a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate and the co-solvent, preferably the co-solvent is dimethyl sulfoxide.

Thus, the present invention is directed to a method for producing guanosine 5'-diphospho-β-L-fucose from guanosine and D-mannose comprising the following steps:
A) providing a solution comprising
  (i) guanosine and D-mannose;
  (ii) polyphosphate, adenosine triphosphate, NADPH and a co-solvent for solubilizing guanosine; and
  providing a set of enzymes comprising a guanosine kinase, a polyphosphate kinase and either
    (a) a glucokinase, a phosphomannomutase, a mannose-1-phosphate guanylyltransferase, a GDP-mannose-4,6-dehydratase and a GDP-L-fucose-synthase, a pyrophosphatase and any of a glucose dehydrogenase, a glucose-6-phosphate-dehydrogenase and glutamate dehydrogenase; or
    (b) an N-acetylhexosamine-1-kinase, a mannose-1-phosphate guanylyltransferase, a GDP-mannose 4,6-dehydratase and a GDP-L-fucose-synthase, a pyrophosphatase, and any of a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate and the co-solvent, preferably dimethyl sulfoxide by
  (a) forming mannose-1-phosphate (Man-1-P) from D-mannose and adenosine triphosphate being catalyzed by a N-acetylhexosamine-1-kinase
    or
    forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomannomutase;
  (b1) forming guanosine monophosphate (GMP) from guanosine and adenosine triphosphate being catalyzed by a guanosine kinase;
  (b2') forming guanosine diphosphate (GDP) from guanosine monophosphate and polyphosphate being catalyzed by a polyphosphate kinase,
  (b2") forming guanosine triphosphate (GTP) from guanosine diphosphate and polyphosphate being catalyzed by a polyphosphate kinase; and
  (c') reacting mannose-1-phosphate with guanosine triphosphate to GDP-mannose and pyrophosphate in the presence of a D-mannose-1-phosphate guanylyl-transferase
  (c") converting pyrophosphate to phosphate in the presence of a pyrophosphatase.
  (d) forming GDP-4-dehydro-6-deoxy-alpha-D-mannose from GDP-mannose being catalyzed by GDP-mannose-4,6-dehydratase; and
  (e) forming GDP-fucose from GDP-4-dehydro-6-deoxy-alpha-D-mannose and NADPH being catalyzed by GDP-L-fucose synthase; and
  (f) regenerating NADPH from NADP+ being catalyzed by any of a glucose dehydrogenase, a glucose-6-phosphate-dehydrogenase and glutamate dehydrogenase.

In the synthesis of GDP-fucose from guanosine and D-mannose, GDP may be in situ produced from GMP by a guanylate kinase (GMK).

Thus, the present invention is directed to a method for producing guanosine 5'-diphospho-β-L-fucose from guanosine and D-mannose comprising the following steps:
A) providing a solution comprising
  (i) guanosine and D-mannose
  (ii) polyphosphate, adenosine triphosphate and a co-solvent for solubilizing guanosine; and providing a set of enzymes comprising a guanosine kinase, a polyphosphate kinase, a guanylate kinase (GMK) and either
- (a) a glucokinase, a phosphomannomutase, a mannose-1-phosphate guanylyltransferase, a GDP-mannose-4,6-dehydratase and a GDP-L-fucose-synthase; or
- (b) an N-acetylhexosamine-1-kinase, a mannose-1-phosphate guanylyl-transferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent, preferably the co-solvent is dimethyl sulfoxide.

Thus, the present invention is directed to a method for producing guanosine 5'-diphospho-β-L-fucose from guanosine and D-mannose comprising the following steps:

A) providing a solution comprising
  (i) guanosine and D-mannose;
  (ii) polyphosphate, adenosine triphosphate, NADPH and a co-solvent for solubilizing guanosine; and
  providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase; or
    (b) an N-acetylhexosamine-1-kinase, a mannose-1-phosphate guanylyl-transferase, a GDP-mannose 4,6-dehydratase and a GDP-L-fucose-synthase, a pyrophosphatase;

B) producing guanosine 5'-diphospho-β-L-fucose from guanosine and D-mannose in the presence of the set of enzymes, polyphosphate, adenosine triphosphate, NADPH and the co-solvent, preferably dimethyl sulfoxide by
(a) forming mannose-1-phosphate (Man-1-P) from D-mannose and adenosine triphosphate being catalyzed by a N-acetylhexosamine-1-kinase
  or
  forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomanno-mutase;
(b1) forming guanosine monophosphate (GMP) from guanosine and adenosine triphosphate being catalyzed by a guanosine kinase;
(b2') forming guanosine diphosphate (GDP) from guanosine monophosphate and polyphosphate being catalyzed by a guanylate kinase (GMK),
(b2") forming guanosine triphosphate (GTP) from guanosine diphosphate and polyphosphate being catalyzed by a polyphosphate kinase; and
(c') reacting mannose-1-phosphate with guanosine triphosphate to GDP-mannose and pyrophosphate in the presence of a D-mannose-1-phosphate guanylyl-transferase
(d) forming GDP-4-dehydro-6-deoxy-alpha-D-mannose from GDP-mannose being catalyzed by GDP-mannose-4,6-dehydratase; and
(e) forming GDP-fucose from GDP-4-dehydro-6-deoxy-alpha-D-mannose and NADPH being catalyzed by GDP-L-fucose synthase.

Preferred, the present invention is directed to a method for producing guanosine 5'-diphospho-β-L-fucose from guanosine and D-mannose comprising the following steps:

A) providing a solution comprising
  (i) guanosine and D-mannose
  (ii) polyphosphate, adenosine triphosphate, NADPH and a co-solvent for solubilizing guanosine; and
  providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase, a pyrophosphatase; or
    (b) an N-acetylhexosamine-1-kinase, a mannose-1-phosphate guanylyl-transferase, a GDP-mannose 4,6-dehydratase and a GDP-L-fucose-synthase, a pyrophosphatase;

B) producing guanosine 5'-diphospho-β-L-fucose from guanosine and D-mannose in the presence of the set of enzymes, polyphosphate, adenosine triphosphate and the co-solvent, preferably the co-solvent is dimethyl sulfoxide.

Thus, the present invention is directed to a method for producing guanosine 5'-diphospho-β-L-fucose from guanosine and D-mannose comprising the following steps:

A) providing a solution comprising
  (i) guanosine and D-mannose
  (ii) polyphosphate, adenosine triphosphate, NADPH and a co-solvent for solubilizing guanosine; and
  providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase, a pyrophosphatase; or
    (b) an N-acetylhexosamine-1-kinase, a mannose-1-phosphate guanylyl-transferase, a GDP-mannose 4,6-dehydratase and a GDP-L-fucose-synthase, a pyrophosphatase;

B) producing guanosine 5'-diphospho-β-L-fucose from guanosine and D-mannose in the presence of the set of enzymes, polyphosphate, adenosine triphosphate, NADPH and the co-solvent, preferably dimethyl sulfoxide by
(a) forming mannose-1-phosphate (Man-1-P) from D-mannose and adenosine triphosphate being catalyzed by a N-acetylhexosamine-1-kinase
  or
  forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomannomutase;
(b1) forming guanosine monophosphate (GMP) from guanosine and adenosine triphosphate being catalyzed by a guanosine kinase;
(b2') forming guanosine diphosphate (GDP) from guanosine monophosphate and polyphosphate being catalyzed by a guanylate kinase (GMK),
(b2") forming guanosine triphosphate (GTP) from guanosine diphosphate and polyphosphate being catalyzed by a polyphosphate kinase; and (c') reacting mannose-1-phosphate with guanosine triphosphate to GDP-mannose and pyrophosphate in the presence of a D-mannose-1-phosphate guanylyltransferase
(c") converting pyrophosphate to phosphate in the presence of a pyrophosphatase.
(d) forming GDP-4-dehydro-6-deoxy-alpha-D-mannose from GDP-mannose being catalyzed by GDP-mannose-4,6-dehydratase; and
(e) forming GDP-fucose from GDP-4-dehydro-6-deoxy-alpha-D-mannose and NADPH being catalyzed by GDP-L-fucose synthase.

Preferred, the present invention is directed to a method for producing guanosine 5'-diphospho-β-L-fucose from guanosine and D-mannose comprising the following steps:
A) providing a solution comprising
  (i) guanosine and D-mannose
  (ii) polyphosphate, adenosine triphosphate and a co-solvent for solubilizing guanosine; and
  providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase, and any of a glucose dehydrogenase, a glucose-6-phosphate-dehydrogenase and glutamate dehydrogenase; or
    (b) an N-acetylhexosamine-1-kinase, a mannose-1-phosphate guanylyl-transferase, a GDP-mannose 4,6-dehydratase and a GDP-L-fucose-synthase, and any of a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate and the co-solvent, preferably the co-solvent is dimethyl sulfoxide.

Thus, the present invention is directed to a method for producing guanosine 5'-diphospho-β-L-fucose from guanosine and D-mannose comprising the following steps:
A) providing a solution comprising
  (i) guanosine and D-mannose
  (ii) polyphosphate, adenosine triphosphate, NADPH and a co-solvent for solubilizing guanosine; and
  providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase, and any of a glucose dehydrogenase, a glucose-6-phosphate-dehydrogenase and glutamate dehydrogenase; or
    (b) an N-acetylhexosamine-1-kinase, a mannose-1-phosphate guanylyl-transferase, a GDP-mannose 4,6-dehydratase and a GDP-L-fucose-synthase, and any of a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate and the co-solvent, preferably dimethyl sulfoxide, by (a) forming mannose-1-phosphate (Man-1-P) from D-mannose and adenosine triphosphate being catalyzed by a N-acetylhexosamine-1-kinase
or
forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomannomutase;
(b1) forming guanosine monophosphate (GMP) from guanosine and adenosine triphosphate being catalyzed by a guanosine kinase;
(b2') forming guanosine diphosphate (GDP) from guanosine monophosphate and polyphosphate being catalyzed by a guanylate kinase (GMK),
(b2") forming guanosine triphosphate (GTP) from guanosine diphosphate and polyphosphate being catalyzed by a polyphosphate kinase; and
(c') reacting mannose-1-phosphate with guanosine triphosphate to GDP-mannose and pyrophosphate in the presence of a D-mannose-1-phosphate guanylyltransferase;
(d) forming GDP-4-dehydro-6-deoxy-alpha-D-mannose from GDP-mannose being catalyzed by GDP-mannose-4,6-dehydratase;
(e) forming GDP-fucose from GDP-4-dehydro-6-deoxy-alpha-D-mannose and NADPH being catalyzed by GDP-L-fucose synthase; and
(f) regenerating NADPH from NADP+ being catalyzed by any of a glucose dehydrogenase, a glucose-6-phosphate-dehydrogenase and glutamate dehydrogenase.

Also preferred, the present invention is directed to a method for producing guanosine 5'-diphospho-β-L-fucose from guanosine and D-mannose comprising the following steps:
A) providing a solution comprising
  (i) guanosine and D-mannose
  (ii) polyphosphate, adenosine triphosphate and a co-solvent for solubilizing guanosine; and
  providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase, a pyrophosphatase, and any of a glucose dehydrogenase, a glucose-6-phosphate-dehydrogenase and glutamate dehydrogenase; or
    (b) an N-acetylhexosamine-1-kinase, a mannose-1-phosphate guanylyl-transferase, a GDP-mannose 4,6-dehydratase and a GDP-L-fucose-synthase, a pyrophosphatase, and any of a glucose dehydrogenase, a glucose-6-phosphate-dehydrogenase and glutamate dehydrogenase;
B) producing guanosine 5'-diphospho-β-L-fucose from guanosine and D-mannose in the presence of the set of enzymes, polyphosphate, adenosine triphosphate and the co-solvent, preferably the co-solvent is dimethyl sulfoxide.

Thus, the present invention is directed to a method for producing guanosine 5'-diphospho-β-L-fucose from guanosine and D-mannose comprising the following steps:
A) providing a solution comprising
  (i) guanosine and D-mannose;
  (ii) polyphosphate, adenosine triphosphate, NADPH and a co-solvent for solubilizing guanosine; and providing a set of enzymes comprising a guanosine kinase, a polyphosphate kinase, a guanylate kinase (GMK) and either
    (a) a glucokinase, a phosphomannomutase, a mannose-1-phosphate guanylyltransferase, a GDP-mannose-4,6-dehydratase and a GDP-L-fucose-synthase, a pyrophosphatase, and any of a glucose dehydrogenase, a glucose-6-phosphate-dehydrogenase and glutamate dehydrogenase; or
    (b) an N-acetylhexosamine-1-kinase, a mannose-1-phosphate guanylyl-transferase, a GDP-mannose 4,6-dehydratase and a GDP-L-fucose-synthase, a pyrophosphatase, and any of a glucose dehydrogenase, a glucose-6-phosphate-dehydrogenase and glutamate dehydrogenase;

B) producing guanosine 5'-diphospho-β-L-fucose from guanosine and D-mannose in the presence of the set of enzymes, polyphosphate, adenosine triphosphate and the co-solvent, preferably dimethyl sulfoxide by
    (a) forming mannose-1-phosphate (Man-1-P) from D-mannose and adenosine triphosphate being catalyzed by a N-acetylhexosamine-1-kinase
    or
    forming mannose-6-phosphate (Man-6-P) from D-mannose and adenosine triphosphate being catalyzed by glucokinase and forming mannose-1-phosphate (Man-1-P) from mannose-6-phosphate being catalyzed by phosphomannomutase;
    (b1) forming guanosine monophosphate (GMP) from guanosine and adenosine triphosphate being catalyzed by a guanosine kinase;
    (b2') forming guanosine diphosphate (GDP) from guanosine monophosphate and polyphosphate being catalyzed by a guanylate kinase (GMK),
    (b2") forming guanosine triphosphate (GTP) from guanosine diphosphate and polyphosphate being catalyzed by a polyphosphate kinase; and
    (c') reacting mannose-1-phosphate with guanosine triphosphate to GDP-mannose and pyrophosphate in the presence of a D-mannose-1-phosphate guanylyl-transferase
    (c") converting pyrophosphate to phosphate in the presence of a pyrophosphatase.
    (d) forming GDP-4-dehydro-6-deoxy-alpha-D-mannose from GDP-mannose being catalyzed by GDP-mannose-4,6-dehydratase; and
    (e) forming GDP-fucose from GDP-4-dehydro-6-deoxy-alpha-D-mannose and NADPH being catalyzed by GDP-L-fucose synthase; and
    (f) regenerating NADPH from NADP+ being catalyzed by any of a glucose dehydrogenase, a glucose-6-phosphate-dehydrogenase and glutamate dehydrogenase.

Due to the recycling of the by-product NADP$^+$ in the inventive methods for producing GDP-fucose from guanosine and D-mannose described herein, lower amounts of NADPH are required in the solution provided in step A). Thus, in one embodiment, the molar ratio of NADPH to D-mannose is between 0.01 and 0.5, more preferably between 0.02 and 0.5, more preferably between 0.03 and 0.4, more preferably between 0.03 and 0.3 and most preferably, between 0.05 and 0.2. In one embodiment, the molar ratio of NADPH to D-mannose is 0.05. In one embodiment, the molar ratio of NADPH to D-mannose is 0.1. In one embodiment, the molar ratio of NADPH to D-mannose is 0.2. In one embodiment, the molar ratio of NADPH to D-mannose is 0.5.

The inventive method for producing GDP-fucose can also be carried out with a set of immobilized enzymes. The enzymes are then immobilized on a solid support such that they retain their activity, substrate specificity, stereoselectivity and/or other properties. Suitable solid supports are for instance beads, monoliths, spheres, particles, a particle bed, a fiber mat, granules, a gel, a membrane, a hollow-fiber membrane, a mixed-matrix membrane, a surface or other solid phase material. In one embodiment, each enzyme, i.e. the guanosine kinase, the polyphosphate kinase, the L-fucokinase/L-fucose-1-phosphate guanylyltransferase and optionally the pyrophosphatase, is immobilized on a solid support. In a further embodiment, each enzyme, i.e. the guanosine kinase, the polyphosphate kinase, the glucokinase, the phosphomannomutase, the mannose-1-phosphate guanylyltransferase, the GDP-mannose-4,6-dehydratase the GDP-L-fucose-synthase, optionally the pyrophosphatase, optionally the guanylate kinase, and optionally an enzyme selected from a glucose dehydrogenase, a glucose-6-phosphate dehydrogenase and a glutamate dehydrogenase, is immobilized on a solid support. In a further embodiment, each enzyme, i.e. the guanosine kinase, the polyphosphate kinase, the N-acetylhexosamine-1-kinase, the mannose-1-phosphate guanylyltransferase, the GDP-mannose 4,6-dehydratase the GDP-L-fucose-synthase, optionally the pyrophosphatase, optionally the guanylate kinase, and an enzyme selected from a glucose dehydrogenase, a glucose-6-phosphate dehydrogenase and a glutamate dehydrogenase, is immobilized on a solid support.

In one embodiment, only some of the enzymes of the set of enzymes are immobilized on a solid support. In a further embodiment only one enzyme selected from the set of enzymes comprising a guanosine kinase, a polyphosphate kinase or a combination of polyphosphate kinases e.g. combination 1D and 2D-ppk2 and ppk3, a L-fucokinase/L-fucose-1-phosphate guanylyltransferase and optionally a pyro-phosphatase is immobilized on a solid support. In yet another embodiment, at least one enzyme selected from the set of enzymes comprising a guanosine kinase, a polyphosphate kinase, a L-fucokinase/L-fucose-1-phosphate guanylyltransferase and optionally a pyrophosphatase is immobilized on a solid support. Preferably, the polyphosphate kinase is immobilized on a solid support. Preferably, the guanosine kinase is immobilized on a solid support. Preferably, the L-fucokinase/L-fucose-1-phosphate guanylyltransferase is immobilized on a solid support. Preferably, the pyrophosphatase is immobilized on a solid support.

Thus, the present invention is also directed to a method for producing guanosine 5'-diphospho-β-L-fucose from guanosine and L-fucose or from guanosine and D-mannose comprising the following steps:
    A) providing a solution comprising
        (i) guanosine and L-fucose or guanosine and D-mannose,
        (ii) polyphosphate, adenosine triphosphate and a co-solvent for solubilizing guanosine; and
    providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the set of enzymes is bound or immobilized on a solid support.

Thus, the present invention is also directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent, wherein the set of enzymes is bound or immobilized on a solid support.

Thus, the present invention is also directed to a method for producing guanosine 5'-diphospho-β-L-fucose from guanosine and D-mannose comprising the following steps:

A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate, NADPH and the co-solvent, wherein the set of enzymes is bound or immobilized on a solid support.

Also, the present invention is directed to a method for producing guanosine 5'-diphospho-β-L-fucose from guanosine and L-fucose or from guanosine and D-mannose comprising the following steps:

A) providing a solution comprising
  (i) guanosine and L-fucose or guanosine and D-mannose,
  (ii) polyphosphate, adenosine triphosphate, and a co-solvent for solubilizing guanosine; and
  providing a set of enzymes comprising a guanosine kinase, a polyphosphate kinase, a pyrophosphatase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the set of enzymes is bound or immobilized on a solid support.

Also, the present invention is directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a L-fucokinase/L-fucose-1-phosphate guanylyltransferase and a pyrophosphatase;

B) producing guanosine 5'-diphospho-β-L-fucose from guanosine and fucose in the presence of the set of enzymes, polyphosphate, adenosine triphosphate and the co-solvent, wherein the set of enzymes is immobilized on a solid support.

Also, the present invention is directed to a method for producing guanosine 5'-diphospho-β-L-fucose from guanosine and D-mannose comprising the following steps:

A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase, a pyrophosphatase and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent, wherein the set of enzymes is immobilized on a solid support.

The present invention is further directed to a method for producing guanosine 5'-diphospho-β-L-fucose from guanosine and L-fucose or from guanosine and D-mannose comprising the following steps:

A) providing a solution comprising
  (i) guanosine and L-fucose or guanosine and D-mannose,
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein at least one enzyme of the set of enzymes is immobilized on a solid support.

Thus, the present invention is also directed to a method for producing guanosine 5'-diphospho-β-L-fucose from guanosine and L-fucose comprising the following steps:
A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent,
wherein at least one enzyme of the set of enzymes is immobilized on a solid support.

Thus, the present invention is also directed to a method for producing guanosine 5'-diphospho-β-L-fucose from guanosine and D-mannose comprising the following steps:
A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase and a glucokinase, phosphomannomutase, a mannose-1-phosphate guanylyltransferase, a GDP-mannose-4,6-dehydratase and a GDP-L-fucose-synthase or a N-acetylhexosamine-1-kinase, a mannose-1-phosphate guanylyl-transferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
wherein at least one enzyme of the set of enzymes is immobilized on a solid support.

Preferably the enzymes used in the inventive methods described herein are co-immobilized on a solid support. Immobilization of sequentially acting enzymes within a confined space increases catalytic efficiency of conversion due to dramatic reduction in the diffusion time of the substrate. In addition, the in-situ formation of substrates generates high local concentrations that lead to kinetic enhancements and can equate to substantial cost savings. Co-immobilization is usually achieved by mixing the enzymes prior immobilization on a solid support.

Thus, the present invention is also directed to a method for producing guanosine 5'-diphospho-β-L-fucose from guanosine and L-fucose or from guanosine and D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyl-transferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the set of enzymes is co-immobilized on a solid support.

Thus, the present invention is also directed to a method for producing guanosine 5'-diphospho-β-L-fucose from guanosine and L-fucose comprising the following steps:
A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent,
wherein the set of enzymes is co-immobilized on a solid support.

Thus, the present invention is also directed to a method for producing guanosine 5'-diphospho-β-L-fucose from guanosine and D-mannose comprising the following steps:
A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase and a glucokinase, phosphomannomutase, a mannose-1-phosphate guanylyltransferase, a GDP-mannose-4,6-dehydratase and a GDP-L-fucose-synthase or a N-acetylhexosamine-1-kinase, a mannose-1-phosphate guanylyl-transferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
wherein the set of enzymes is co-immobilized on a solid support.

The present invention is also directed to a method for producing guanosine 5'-diphospho-β-L-fucose from guanosine and L-fucose or from guanosine and D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1- kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent.

Thus, the present invention is also directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes co-immobilized on a solid support comprising a guanosine kinase, a polyphosphate kinase, and a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent.

Thus, the present invention is also directed to a method for producing guanosine 5'-diphospho-β-L-fucose from guanosine and D-mannose comprising the following steps:

A) providing a solution comprising
  (i) guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase and a glucokinase, phosphomannomutase, a mannose-1-phosphate guanylyltransferase, a GDP-mannose-4,6-dehydratase and a GDP-L-fucose-synthase or a N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent.

The present invention is also directed to a method for producing guanosine 5'-diphospho-β-L-fucose from guanosine and L-fucose or from guanosine and D-mannose comprising the following steps:

A) providing a solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the co-solvent is dimethyl sulfoxide.

Thus, the present invention is also directed to a method for producing guanosine 5'-diphospho-β-L-fucose from guanosine and L-fucose comprising the following steps:

A) providing a solution comprising
  (i) guanosine and L-fucose,
  (ii) polyphosphate, adenosine triphosphate and a co-solvent for solubilizing guanosine; and
  providing a set of enzymes co-immobilized on a solid support comprising a guanosine kinase, a polyphosphate kinase, and a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent, wherein the co-solvent is dimethyl sulfoxide.

Thus, the present invention is also directed to a method for producing guanosine 5'-diphospho-β-L-fucose from guanosine and D-mannose comprising the following steps:

A) providing a solution comprising
  (i) guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase and a glucokinase, phosphomannomutase, a mannose-1-phosphate guanylyltransferase, a GDP-mannose-4,6-dehydratase and a GDP-L-fucose-synthase or a N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent, wherein the co-solvent is dimethyl sulfoxide.

The present invention is further directed to a method for producing guanosine 5'-diphospho-β-L-fucose from guanosine and L-fucose or from guanosine and D-mannose comprising the following steps:

A) providing a solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the solid support has the form of beads, monoliths, spheres, particles, a particle bed, a fiber mat, granules, a gel, a membrane, a hollow-fiber membrane, a mixed-matrix membrane or a surface.

In such embodiments, the immobilized enzymes can facilitate the production of guanosine 5'-diphospho-β-L-fucose from guanosine and L-fucose, and after the reaction is complete the immobilized enzymes are easily retained (e.g., by retaining beads on which the enzymes are immobilized) and then reused or recycled in subsequent runs. Such immobilized biocatalytic processes allow for further efficiency and cost reduction. In addition, the inventive method can be conducted in a continuous manner by passing the feed solution of step A) through a reactor containing the set of enzymes immobilized on a solid support.

Thus in one embodiment the method for producing guanosine 5'-diphospho-β-L-fucose from guanosine and L-fucose or from guanosine and D-mannose comprises the following steps:
A) providing a feed solution comprising
  (i) guanosine and L-fucose or guanosine and D-mannose,
  (ii) polyphosphate, adenosine triphosphate and a co-solvent for solubilizing guanosine; and
  providing a set of enzymes immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase, wherein the solid support comprising the set of immobilized enzymes is located in a chemical reactor,
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent by continuously passing the feed solution from step A) through the chemical reactor loaded with the solid support comprising the set of immobilized enzymes.

Also the method for producing guanosine 5'-diphospho-β-L-fucose from guanosine and L-fucose or from guanosine and D-mannose comprises the following steps:
A) providing a feed solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase, wherein the solid support comprising the set of co-immobilized enzymes is located in a chemical reactor,
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent by continuously passing the feed solution from step A) through the chemical reactor loaded with the solid support comprising the set of co-immobilized enzymes,
wherein the co-solvent is dimethyl sulfoxide.

Thus, the method for producing guanosine 5'-diphospho-β-L-fucose from guanosine and L-fucose comprises the following steps:
A) providing a feed solution comprising
  (i) guanosine and L-fucose,
  (ii) polyphosphate, adenosine triphosphate and a co-solvent for solubilizing guanosine; and
  providing a set of enzymes co-immobilized on a solid support comprising a guanosine kinase, a polyphosphate kinase, and a L-fucokinase/L-fucose-1-phosphate guanylyltransferase, wherein the solid support comprising the set of co-immobilized enzymes is located in a chemical reactor,
B) producing guanosine 5'-diphospho-β-L-fucose from guanosine and fucose in the presence of the set of enzymes, polyphosphate, adenosine triphosphate and the co-solvent by continuously passing the feed solution from step A) through the chemical reactor loaded with the solid support comprising the set of co-immobilized enzymes,
wherein the co-solvent is dimethyl sulfoxide.

Thus, the method for producing guanosine 5'-diphospho-β-L-fucose from guanosine and D-mannose comprises the following steps:
A) providing a feed solution comprising
  (i) guanosine and L D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase, wherein the solid support comprising the set of co-immobilized enzymes is located in a chemical reactor,
B) producing guanosine 5'-diphospho-β-L-fucose from guanosine and D-mannose in the presence of the set of enzymes, polyphosphate, adenosine triphosphate and the co-solvent by continuously passing the feed solution from step A) through the chemical reactor loaded with the solid support comprising the set of co-immobilized enzymes,
wherein the co-solvent is dimethyl sulfoxide.

Methods of enzyme immobilization are well-known in the art. The enzymes can be bound non-covalently or covalently, such as adsorption, covalent binding, ionic binding, metal binding, crosslinking or crystallization. Various methods for conjugation and immobilization of enzymes to solid supports (e.g., resins, membranes, beads, glass, etc.) are well known in the art and described in e.g.: Yi et al., Process Biochemistry 2007, 42, 895; Martin et al., Applied Microbiology and Biotechnology 2007, 76, 843; Koszelewski et al., Journal of Molecular Catalysis B: Enzymatic, 2010, 63, 39; Truppo et al., Org. Process Res. Dev., 2011, 15, 1033; Hermanson, G. T., Bioconjugate Techniques, Second Edition, Academic Press (2008); Mateo et al., Biotechnology Progress, 2002, 18, 629; and Bioconjugation Protocols: Strategies and Methods, In Methods in Molecular Biology, C. M. Niemeyer ed., Humana Press (2004).

The enzymes used in the inventive methods described herein can be prepared by recombinant methods from bacteria, such as E. coli. The enzyme-containing solutions obtained from cell lysis, which are usually centrifuged and filtered to remove cell debris, can be directly used for immobilizing the enzymes on a solid support. Thus, no further purification step or isolation step is required and the crude cell lysate can be used for immobilizing the enzymes on a solid support such that they retain their activity, substrate specificity, stereoselectivity and/or other properties.

Thus, the present invention is further directed to a method for producing guanosine 5'-diphospho-β-L-fucose from guanosine and L-fucose or from guanosine and D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the set of enzymes is immobilized on a solid support from cell lysate.

Also, the present invention is directed to a method for producing guanosine 5'-diphospho-β-L-fucose from guanosine and L-fucose or from guanosine and D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the set of enzymes is immobilized on a solid support from crude cell lysate.

Also, the present invention is directed to a method for producing guanosine 5'-diphospho-β-L-fucose from guanosine and L-fucose or from guanosine and D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, optionally a pyrophosphatase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the set of enzymes is co-immobilized on a solid support from cell lysate.

Further, the present invention is directed to a method for producing guanosine 5'-diphospho-β-L-fucose from guanosine and L-fucose or from guanosine and D-mannose comprising the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized on a solid support comprising a guanosine kinase, a polyphosphate kinase, optionally a pyrophosphatase and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the set of enzymes is co-immobilized on a solid support from cell lysate, and the co-solvent is dimethyl sulfoxide.

Further, the present invention is directed to a method for producing guanosine 5'-diphospho-β-L-fucose from guanosine and L-fucose or from guanosine and D-mannose comprising the following steps:

A) providing a solution comprising
   (i) guanosine and L-fucose or guanosine and D-mannose,
   (ii) polyphosphate, adenosine triphosphate and a co-solvent for solubilizing guanosine; and
   providing a set of enzymes comprising a guanosine kinase, a polyphosphate kinase, optionally a pyrophosphatase and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein at least one enzyme of the set of enzymes is co-immobilized on a solid support from cell lysate.

Solid supports useful for immobilizing the enzymes used in the method of the present invention include but are not limited to beads or resins comprising polymethacrylate with epoxide functional groups, polymethacrylate with epoxide functional groups, polymethacrylate with amino epoxide functional groups, polymethacrylate with ethylenediamine functional groups, polyacrylic acid with epoxy functional groups, polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, magnetic silica particles with Ni-NTA functional group, or magnetic nanoparticles with a core of magnetite and a dextran shell with Ni-NTA functional group. Exemplary solid supports useful for immobilizing the enzymes used in the inventive method include, but are not limited to, sepabeads (Resindion): EC-EP, EP403/M, EC-HFA, EC-EA/M and EC-HA; immobeads (ChiralVision) IB-COV1, IB-COV2, IB-COV3, IB-ANI1, IB-ANI2, IB-ANI3, IB-ANI4, IB-CAT1, IB-ADS1, IB-ADS2, IB-ADS3 and IB-ADS4; Eupergit (Röhm GmbH & Co. KG) and magnetic particles (micromod GmbH): Nano-mag, Sicastar-6 and Sicastar-1.5. Preferably, the solid support is composed of a resin or beads selected from: sepabeads (Resindion): EC-EP, EP403/M, EC-EA/M and EC-HA; immobeads (ChiralVision) IB-COV1, IB-COV2, IB-COV3, IB-ANI1, IB-CAT1, IB-ADS1, IB-ADS2, IB-ADS3 and IB-ADS4; Eupergit (ROhm GmbH & Co. KG) and magnetic particles (micromod GmbH): Nano-mag, Sicastar-6 and Sicastar-1.5.

Thus, the present invention is further directed to a method for producing guanosine 5'-diphospho-β-L-fucose from guanosine and L-fucose or from guanosine and D-mannose comprising the following steps:

A) providing a solution comprising
   (i) guanosine and L-fucose or guanosine and D-mannose,
   (ii) polyphosphate, adenosine triphosphate and a co-solvent for solubilizing guanosine; and
   providing a set of enzymes immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the solid support is composed of a resin or beads selected from: sepabeads: EC-EP, EP403/M, EC-EA/M and EC-HA; immobeads: IB-COV1, IB-COV2, IB-COV3, IB-ANI1, IB-CAT1, IB-ADS1, IB-ADS2, IB-ADS3 and IB-ADS4; Eupergit and magnetic particles: Nano-mag, Sicastar-6 and Sicastar-1.5.

Also, the present invention is further directed to a method for producing guanosine 5'-diphospho-β-L-fucose from guanosine and L-fucose or from guanosine and D-mannose comprising the following steps:

A) providing a solution comprising
   (i) guanosine and L-fucose or guanosine and D-mannose,
   (ii) polyphosphate, adenosine triphosphate and a co-solvent for solubilizing guanosine; and
   providing a set of enzymes immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent, wherein the solid support is composed of a resin or beads selected from: sepabeads: EC-EP, EP403/M, EC-EA/M and EC-HA; immobeads: IB-COV1, IB-COV2, IB-COV3, IB-ANI1, IB-CAT1, IB-ADS1, IB-ADS2, IB-ADS3 and IB-ADS4; Eupergit and magnetic particles: Nano-mag, Sicastar-6 and Sicastar-1.5; and wherein the co-solvent is dimethyl sulfoxide.

Also, the present invention is further directed to a method for producing guanosine 5'-diphospho-β-L-fucose from guanosine and L-fucose or from guanosine and D-mannose comprising the following steps:

A) providing a solution comprising
   (i) guanosine and L-fucose or guanosine and D-mannose,
   (ii) polyphosphate, adenosine triphosphate and a co-solvent for solubilizing guanosine; and
   providing a set of enzymes immobilized on a solid support comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent,
wherein the solid support is composed of beads or resins comprising polymethacrylate with epoxide functional groups, polymethacrylate with epoxide functional groups, polymethacrylate with amino epoxide functional groups, polymethacrylate with ethylenediamine functional groups, polyacrylic acid with epoxy functional groups, polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, magnetic silica particles with Ni-NTA functional group, or magnetic nanoparticles with a core of magnetite and a dextran shell with Ni-NTA functional group.

In a further embodiment of the present invention, the method for producing guanosine 5'-diphospho-β-L-fucose comprises the additional step C):
C) isolating the guanosine 5'-diphospho-β-L-fucose.

In a further embodiment of the present invention, the method for producing guanosine 5'-diphospho-β-L-fucose comprises the additional step C):
C) isolating the guanosine 5'-diphospho-β-L-fucose by ion exchange chromatography.

Thus, the present invention is further directed to a method for producing guanosine 5'-diphospho-β-L-fucose from guanosine and L-fucose or guanosine and D-mannose comprising the following steps:
A) providing a solution comprising
   (i) guanosine and L-fucose or guanosine and D-mannose
   (ii) polyphosphate, adenosine triphosphate and a co-solvent for solubilizing guanosine; and
   providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
C) isolating the guanosine 5'-diphospho-β-L-fucose.

Thus, the present invention is further directed to a method for producing guanosine 5'-diphospho-β-L-fucose from guanosine and L-fucose comprising the following steps:
A) providing a solution comprising
   (i) guanosine and L-fucose,
   (ii) polyphosphate, adenosine triphosphate and a co-solvent for solubilizing guanosine; and
   providing a set of enzymes comprising a guanosine kinase, a polyphosphate kinase, and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent; and
C) isolating the guanosine 5'-diphospho-β-L-fucose.

Preferably, the method for producing guanosine 5'-diphospho-β-L-fucose from guanosine and L-fucose or guanosine and D-mannose comprises the following steps:
A) providing a solution comprising
   (i) guanosine and L-fucose or guanosine and D-mannose
   (ii) polyphosphate, adenosine triphosphate and a co-solvent for solubilizing guanosine; and
   providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase; and a pyrophosphatase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
C) isolating the guanosine 5'-diphospho-β-L-fucose.

Preferably, the method for producing guanosine 5'-diphospho-β-L-fucose from guanosine and L-fucose comprises the following steps:
A) providing a solution comprising
   (i) guanosine and L-fucose,
   (ii) polyphosphate, adenosine triphosphate and a co-solvent for solubilizing guanosine; and
   providing a set of enzymes comprising a guanosine kinase, a polyphosphate kinase, a L-fucokinase/L-fucose-1-phosphate guanylyltransferase; and a pyrophosphatase;
B) producing guanosine 5'-diphospho-β-L-fucose from guanosine and fucose in the presence of the set of enzymes, polyphosphate, adenosine triphosphate and the co-solvent; and
C) isolating the guanosine 5'-diphospho-β-L-fucose.

Preferably, the method for producing guanosine 5'-diphospho-β-L-fucose from guanosine and L-fucose or from guanosine and D-mannose comprises the following steps:

A) providing a solution comprising
  (i) guanosine and L-fucose or guanosine and D-mannose,
  (ii) polyphosphate, adenosine triphosphate and a co-solvent for solubilizing guanosine; and
  providing a set of enzymes comprising a guanosine kinase, a polyphosphate kinase, optionally a pyrophosphatase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent; and
C) isolating the guanosine 5'-diphospho-β-L-fucose,
wherein at least one enzyme of the set of enzymes is immobilized on a solid support.

Preferably, the method for producing guanosine 5'-diphospho-β-L-fucose from guanosine and L-fucose or guanosine and D-mannose comprises the following steps:
A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase; and optionally a pyrophosphatase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
C) isolating the guanosine 5'-diphospho-β-L-fucose.

Preferably, the method for producing guanosine 5'-diphospho-β-L-fucose from guanosine and L-fucose comprises the following steps:
A) providing a solution comprising
  (i) guanosine and L-fucose,
  (ii) polyphosphate, adenosine triphosphate and a co-solvent for solubilizing guanosine; and
  providing a set of enzymes immobilized on a solid support comprising a guanosine kinase, a polyphosphate kinase, a L-fucokinase/L-fucose-1-phosphate guanylyltransferase; and optionally a pyrophosphatase;
B) producing guanosine 5'-diphospho-β-L-fucose from guanosine and fucose in the presence of the set of enzymes, polyphosphate, adenosine triphosphate and the co-solvent; and
C) isolating the guanosine 5'-diphospho-β-L-fucose.

Preferably, the method for producing guanosine 5'-diphospho-β-L-fucose from guanosine and L-fucose or from guanosine and D-mannose comprises the following steps:
A) providing a solution comprising
  (i) guanosine and L-fucose or guanosine and D-mannose,
  (ii) polyphosphate, adenosine triphosphate and a co-solvent for solubilizing guanosine; and
  providing a set of enzymes co-immobilized comprising a guanosine kinase, a polyphosphate kinase, optionally a pyrophosphatase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and fucose in the presence of the set of enzymes, polyphosphate, adenosine triphosphate and the co-solvent or from guanosine and D-mannose in the presence of the set of enzymes, polyphosphate, adenosine triphosphate and the co-solvent; and
C) isolating the guanosine 5'-diphospho-β-L-fucose,
wherein the set of enzymes is co-immobilized on a solid support from cell lysate.

Preferably, the method for producing guanosine 5'-diphospho-β-L-fucose from guanosine and L-fucose or guanosine and D-mannose comprises the following steps:
A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase; and a pyrophosphatase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
C) isolating the guanosine 5'-diphospho-β-L-fucose,
wherein the co-solvent is dimethyl sulfoxide.

Preferably, the amount of co-solvent is from 0.01 vol % to 30 vol % based on total volume of the solution provided in step A). Preferably, the co-solvent is dimethyl sulfoxide and the amount of dimethyl sulfoxide is from 0.01 vol % to 30 vol % based on total volume of the solution provided in step A).

Preferably, the polyphosphate is a long-chain polyphosphate having at least 25 phosphate residues.

Preferably, the concentration of guanosine and L-fucose or guanosine and D-mannose in the solution provided in step A) is in the range of 0.2 mM to 5,000 mM.

Preferably, the method for producing guanosine 5'-diphospho-β-L-fucose from guanosine and L-fucose comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a L-fucokinase/L-fucose-1-phosphate guanylyltransferase; and optionally a pyrophosphatase;
B) producing guanosine 5'-diphospho-β-L-fucose from guanosine and fucose in the presence of the set of enzymes, polyphosphate, adenosine triphosphate and the co-solvent; and
C) isolating the guanosine 5'-diphospho-β-L-fucose, wherein the co-solvent is dimethyl sulfoxide.

Preferably, the amount of co-solvent is from 0.01 vol % to 30 vol % based on total volume of the solution provided in step A). Preferably, the co-solvent is dimethyl sulfoxide and the amount of dimethyl sulfoxide is from 0.01 vol % to 30 vol % based on total volume of the solution provided in step A).

Preferably, the polyphosphate is a long-chain polyphosphate having at least 25 phosphate residues.

Preferably, the concentration of guanosine and L-fucose in the solution provided in step A) is in the range of 0.2 mM to 5,000 mM.

Fucosylated Saccharides, Fucosylated Glycopeptides, Fucosylated Glycoproteins, Fucosylated Proteins, Fucosylated Peptides and Fucosylated Small Molecules, Such as Stevia.

In a further aspect of the present invention the inventive methods described herein are useful for producing fucosylated saccharides, fucosylated glycopeptides, fucosylated glycoproteins, fucosylated proteins, fucosylated peptides or fucosylated small molecules, e.g. stevia.

Thus, in one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, and
D) producing a fucosylated saccharide, fucosylated glycopeptide, fucosylated glycoprotein, fucosylated protein, fucosylated peptide or fucosylated small molecule from guanosine 5'-diphospho-β-L-fucose and a saccharide, glyco-peptide, glycoprotein, protein, peptide or small molecule by forming an O-glycosidic bond between guanosine 5'-diphospho-β-L-fucose and an available hydroxyl group of the saccharide, glycopeptide, glycoprotein, protein, peptide or small molecule in the presence of a fucosyltransferase.

Thus, in one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a fucosyltransferase and a L-fucokinase/L-fucose-1-phosphate guanylyltransferase;
B) producing guanosine 5'-diphospho-β-L-fucose from guanosine and fucose in the presence of the set of enzymes, polyphosphate, adenosine triphosphate and the co-solvent; and
D) producing a fucosylated saccharide, fucosylated glycopeptide, fucosylated glycoprotein, fucosylated protein, fucosylated peptide or fucosylated small molecule from guanosine 5'-diphospho-β-L-fucose and a saccharide, glycopeptide, glycoprotein, protein, peptide or small molecule by forming an O-glycosidic bond between guanosine 5'-diphospho-β-L-fucose and an available hydroxyl group of the saccharide, glycopeptide, glycoprotein, protein, peptide or small molecule in the presence of a fucosyltransferase.

Thus, in one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and mannose in the presence of the set of enzymes, polyphosphate, adenosine triphosphate and the co-solvent; and
D) producing a fucosylated saccharide, fucosylated glycopeptide, fucosylated glycoprotein, fucosylated protein, fucosylated peptide or fucosylated small molecule from guanosine 5'-diphospho-β-L-fucose and a saccharide, glycopeptide, glycoprotein, protein, peptide or small molecule by forming an O-glycosidic bond between guanosine 5'-diphospho-β-L-fucose and an available hydroxyl group of the saccharide, glycopeptide, glycoprotein, protein, peptide or small molecule in the presence of a fucosyltransferase.

In one embodiment of the present invention the method for producing a fucosylated saccharide, a fucosylated glycopeptide a fucosylated glycoprotein, a fucosylated protein, a fucosylated peptide or a fucosylated small molecule comprises the following steps:

A) providing a solution comprising
  (i) guanosine and L-fucose or guanosine and D-mannose,
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyl-transferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
C) isolating the guanosine 5'-diphospho-β-L-fucose; and
D) producing a fucosylated saccharide, fucosylated glycopeptide, fucosylated glycoprotein, fucosylated protein, fucosylated peptide or fucosylated small molecule from guanosine 5'-diphospho-β-L-fucose and a saccharide, glycopeptide, glycoprotein, protein, peptide or small molecule by forming an O-glycosidic bond between guanosine 5'-diphospho-β-L-fucose and an available hydroxyl group of the saccharide, glycopeptide, glycoprotein, protein, peptide or small molecule in the presence of a fucosyltransferase.

In one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a fucosyltransferase and a L-fucokinase/L-fucose-1-phosphate guanylyl-transferase;
B) producing guanosine 5'-diphospho-β-L-fucose from guanosine and fucose in the presence of the set of enzymes, polyphosphate, adenosine triphosphate and the co-solvent;
C) isolating the guanosine 5'-diphospho-β-L-fucose; and
D) producing a fucosylated saccharide, fucosylated glycopeptide, fucosylated glycoprotein, fucosylated protein, fucosylated peptide or fucosylated small molecule from guanosine 5'-diphospho-β-L-fucose and a saccharide, glycopeptide, glycoprotein, protein, peptide or small molecule by forming an O-glycosidic bond between guanosine 5'-diphospho-β-L-fucose and an available hydroxyl group of the saccharide, glycopeptide, glycoprotein, protein, peptide or small molecule in the presence of a fucosyltransferase.

In one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and mannose in the presence of the set of enzymes, polyphosphate, adenosine triphosphate and the co-solvent;
C) isolating the guanosine 5'-diphospho-β-L-fucose; and
D) producing a fucosylated saccharide, fucosylated glycopeptide, fucosylated glycoprotein, fucosylated protein, fucosylated peptide or fucosylated small molecule from guanosine 5'-diphospho-β-L-fucose and a saccharide, glycopeptide, glycoprotein, protein, peptide or small molecule by forming an O-glycosidic bond between guanosine 5'-diphospho-β-L-fucose and an available hydroxyl group of the saccharide, glycopeptide, glycoprotein, protein, peptide or small molecule in the presence of a fucosyltransferase.

The fucosyltransferase catalyzes the reaction of GDP-fucose with an available hydroxyl group of a saccharide, glycopeptide, glycoprotein, protein, peptide or small molecule, thereby forming a fucosylated saccharide, fucosylated glycopeptide, fucosylated glycoprotein, a fucosylated protein, a fucosylated peptide or a fucosylated small molecule and guanosine diphosphate (GDP) as side product. GDP being an intermediate product formed in step B), specifically in step (b2') can then be reused or recycled.

Thus, in one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a fucosyltransferase and a L-fucokinase/L-fucose-1-phosphate guanylyl-transferase;
B) producing guanosine 5'-diphospho-β-L-fucose from guanosine and fucose in the presence of the set of enzymes, polyphosphate, adenosine triphosphate and the co-solvent by
  (a) forming fucose-1-phosphate from L-fucose and adenosine triphosphate being catalyzed by a L-fucokinase/L-fucose-1-phosphate guanylyl-transferase,
  (b1) forming guanosine monophosphate from guanosine and adenosine triphosphate being catalyzed by a guanosine kinase;
  (b2') forming guanosine diphosphate from guanosine monophosphate and polyphosphate being catalyzed by a polyphosphate kinase
  (b2") forming guanosine triphosphate from guanosine diphosphate and polyphosphate being catalyzed by a polyphosphate kinase; and (c) reacting fucose-1-phosphate with guanosine triphosphate to GDP-fucose in the presence of a L-fucokinase/L-fucose-1-phosphate guanylyl-transferase;

D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase; and E) recycling the in-situ formed guanosine diphosphate to form guanosine triphosphate.

Thus, in one embodiment of the present invention the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and D-mannose;
  (ii) polyphosphate, adenosine triphosphate and a co-solvent for solubilizing guanosine; and
  providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase and a pyrophosphatase or (b) an N-acetylhexosamine-1-kinase, a mannose-1-phosphate guanylyltransferase, a GDP-mannose 4,6-dehydratase and a GDP-L-fucose-synthase, B) producing guanosine 5'-diphospho-β-L-fucose from guanosine and D-mannose in the presence of the set of enzymes, polyphosphate, adenosine triphosphate and the co-solvent by
  (a) forming mannose-1-phosphate (Man-1-P) from D-mannose and adenosine triphosphate being catalyzed by a N-acetylhexosamine-1-kinase
  or
  forming mannose-6-phosphate (Man-6-P) from D-mannose and adenosine triphosphate being catalyzed by glucokinase and forming mannose-1-phosphat (Man-1-P) from mannose-6-phosphate being catalyzed by phosphomannomutase
  (b1) forming guanosine monophosphate (GMP) from guanosine and adenosine triphosphate being catalyzed by a guanosine kinase;
  (b2') forming guanosine diphosphate (GDP) from guanosine monophosphate and polyphosphate being catalyzed by a polyphosphate kinase
  (b2'') forming guanosine triphosphate (GTP) from guanosine diphosphate and polyphosphate being catalyzed by a polyphosphate kinase; and
  (c') reacting mannose-1-phosphate with guanosine triphosphate to GDP-mannose and pyrophosphate in the presence of a D-mannose-1-phosphate guanylyltransferase
  (c'') converting pyrophosphate to phosphate in the presence of a pyrophosphatase.
  (d) forming GDP-4-dehydro-6-deoxy-alpha-D-mannose from GDP-mannose being catalyzed by GDP-mannose-4,6-dehydratase; and
  (e) forming GDP-fucose from GDP-4-dehydro-6-deoxy-alpha-D-mannose and NADPH being catalyzed by GDP-L-fucose synthase.

D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase; and E) recycling the in-situ formed guanosine diphosphate to form guanosine triphosphate.

Due to the recycling of the by-product guanosine diphosphate in the inventive fucosylation methods described herein, lower amounts of guanosine are required in the solution provided in step A). Thus, in one embodiment, the molar ratio of guanosine to L-fucose or guanosine to D-mannose is between 0.01 and 0.5, more preferably between 0.02 and 0.5, more preferably between 0.03 and 0.4, more preferably between 0.03 and 0.3 and most preferably, between 0.05 and 0.2. In one embodiment, the molar ratio of guanosine to L-fucose or guanosine to D-mannose is 0.05. In one embodiment, the molar ratio of guanosine to L-fucose or guanosine to D-mannose is 0.1. In one embodiment, the molar ratio of guanosine to L-fucose or guanosine to D-mannose is 0.2. In one embodiment, the molar ratio of guanosine to L-fucose or guanosine to D-mannose is 0.5.

Preferably, the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phospho-mannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase, F) isolating the fucosylated saccharide, fucosylated glycopeptide, fucosylated glycoprotein, fucosylated protein, fucosylated peptide or fucosylated small molecule.

Preferably, the method for producing a fucosylated saccharide, a fucosylated glycopeptide, a fucosylated glycoprotein, a fucosylated protein, a fucosylated peptide or a fucosylated small molecule comprises the following steps:
- A) providing a solution comprising
  - (i) guanosine and L-fucose,
  - (ii) polyphosphate, adenosine triphosphate and a co-solvent for solubilizing guanosine; and
  - providing a set of enzymes comprising a guanosine kinase, a polyphosphate kinase, a fucosyltransferase and a L-fucokinase/L-fucose-1-phosphate guanylyltransferase;
- B) producing guanosine 5'-diphospho-β-L-fucose from guanosine and fucose in the presence of the set of enzymes, polyphosphate, adenosine triphosphate and the co-solvent;
- D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase; and
- F) isolating the fucosylated saccharide, fucosylated glycopeptide, fucosylated glycoprotein, fucosylated protein, fucosylated peptide or fucosylated small molecule.

Preferably, the method for producing a fucosylated saccharide, a fucosylated glycopeptide, a fucosylated glycoprotein, a fucosylated protein, a fucosylated peptide or a fucosylated small molecule comprises the following steps:
- A) providing a solution comprising
  - (i) guanosine and L-fucose or guanosine and D-mannose
  - (ii) polyphosphate, adenosine triphosphate and a co-solvent for solubilizing guanosine; and
  - providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetyl-hexosamine-1-kinase, a mannose-1-phosphate guanylyltransferase, a GDP-mannose 4,6-dehydratase and a GDP-L-fucose-synthase;
- B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
- C) isolating the guanosine 5'-diphospho-β-L-fucose; and
- D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase, wherein the co-solvent is dimethyl sulfoxide.

Preferably, the amount of co-solvent is from 0.01 vol % to 30 vol % based on total volume of the solution provided in step A). Preferably, the co-solvent is dimethyl sulfoxide and the amount of dimethyl sulfoxide is from 0.01 vol % to 30 vol % based on total volume of the solution provided in step A).

Preferably, the polyphosphate is a long-chain polyphosphate having at least 25 phosphate residues.

Preferably, the concentration of guanosine and L-fucose or guanosine and D-mannose in the solution provided in step A) is in the range of 0.2 mM to 5,000 mM.

Preferably, the concentration of the enzymes in the set of enzymes is between 0.0001 mg/mL and 100 mg/mL based on the total volume of the solution provided in step A).

Preferably, the method for producing a fucosylated saccharide, a fucosylated glycopeptide, a fucosylated glycoprotein, a fucosylated protein, a fucosylated peptide or a fucosylated small molecule comprises the following steps:
- A) providing a solution comprising
  - (i) guanosine and L-fucose,
  - (ii) polyphosphate, adenosine triphosphate and a co-solvent for solubilizing guanosine; and providing a set of enzymes comprising a guanosine kinase, a polyphosphate kinase, a fucosyltransferase and a L-fucokinase/L-fucose-1-phosphate guanylyl-transferase;
- B) producing guanosine 5'-diphospho-β-L-fucose from guanosine and fucose in the presence of the set of enzymes, polyphosphate, adenosine triphosphate and the co-solvent; and
- D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase, wherein the co-solvent is dimethyl sulfoxide.

Preferably, the method for producing a fucosylated saccharide, a fucosylated glycopeptide, a fucosylated glycoprotein, a fucosylated protein, a fucosylated peptide or a fucosylated small molecule comprises the following steps:
- A) providing a solution comprising
  - (i) guanosine and D-mannose,
  - (ii) polyphosphate, adenosine triphosphate and a co-solvent for solubilizing guanosine; and
  - providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
- B) producing guanosine 5'-diphospho-β-L-fucose from guanosine and mannose in the presence of the set of enzymes, polyphosphate, adenosine triphosphate and the co-solvent; and
- D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase,
wherein the co-solvent is dimethyl sulfoxide.

Preferably, the amount of co-solvent is from 0.01 vol % to 30 vol % based on total volume of the solution provided in step A). Preferably, the co-solvent is dimethyl sulfoxide and the amount of dimethyl sulfoxide is from 0.01 vol % to 30 vol % based on total volume of the solution provided in step A).

Preferably, the polyphosphate is a long-chain polyphosphate having at least 25 phosphate residues.

Preferably, the concentration of guanosine and L-fucose in the solution provided in step A) is in the range of 0.2 mM to 5,000 mM.

Preferably, the concentration of the enzymes in the set of enzymes is between 0.0001 mg/mL and 100 mg/mL based on the total volume of the solution provided in step A).

Preferably, the method for producing a fucosylated saccharide, a fucosylated glycopeptide, a fucosylated glycoprotein, a fucosylated protein, a fucosylated peptide or a fucosylated small molecule comprises the following steps:
A) providing a solution comprising
   (i) guanosine and L-fucose or guanosine and D-mannose
   (ii) polyphosphate, adenosine triphosphate and a co-solvent for solubilizing guanosine; and
   providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase; and a pyrophosphatase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
C) isolating the guanosine 5'-diphospho-β-L-fucose; and
D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase.

Preferably, the method for producing a fucosylated saccharide, a fucosylated glycopeptide, a fucosylated glycoprotein, a fucosylated protein, a fucosylated peptide or a fucosylated small molecule comprises the following steps:
A) providing a solution comprising
   (i) guanosine and L-fucose,
   (ii) polyphosphate, adenosine triphosphate and a co-solvent for solubilizing guanosine; and
   providing a set of enzymes comprising a guanosine kinase, a polyphosphate kinase, a L-fucokinase/L-fucose-1-phosphate guanylyltransferase, a fucosyltransferase and a pyrophosphatase;
B) producing guanosine 5'-diphospho-β-L-fucose from guanosine and fucose in the presence of the set of enzymes, polyphosphate, adenosine triphosphate and the co-solvent; and
D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glyco-peptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase.

Preferably, the method for producing a fucosylated saccharide, a fucosylated glycopeptide, a fucosylated glycoprotein, a fucosylated protein, a fucosylated peptide or a fucosylated small molecule comprises the following steps:
A) providing a solution comprising
   (i) guanosine and L-fucose or guanosine and D-mannose,
   (ii) polyphosphate, adenosine triphosphate and a co-solvent for solubilizing guanosine; and
   providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent; and
D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase,
wherein at least one enzyme of the set of enzymes is immobilized on a solid support.

In one embodiment, the method for producing a fucosylated saccharide, a fucosylated glycopeptide, a fucosylated glycoprotein, a fucosylated protein, a fucosylated peptide or a fucosylated small molecule comprises the following steps:
A) providing a solution comprising
   (i) guanosine and L-fucose,
   (ii) polyphosphate, adenosine triphosphate and a co-solvent for solubilizing guanosine; and
   providing a set of enzymes comprising a guanosine kinase, a polyphosphate kinase, a L-fucokinase/L-fucose-1-phosphate guanylyltransferase, and optionally a pyrophosphatase;
B) producing guanosine 5'-diphospho-β-L-fucose from guanosine and fucose in the presence of the set of enzymes, polyphosphate, adenosine triphosphate and the co-solvent; and D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase, wherein at least one enzyme of the set of enzymes is immobilized on a solid support.

In one embodiment, the method for producing a fucosylated saccharide, a fucosylated glycopeptide, a fucosylated glycoprotein, a fucosylated protein, a fucosylated peptide or a fucosylated small molecule comprises the following steps:

A) providing a solution comprising
  (i) guanosine and D-mannose,
  (ii) polyphosphate, adenosine triphosphate and a co-solvent for solubilizing guanosine; and
  providing a set of enzymes comprising a guanosine kinase, a polyphosphate kinase, and a glucokinase, phosphomannomutase, a mannose-1-phosphate guanylyltransferase, a GDP-mannose-4,6-dehydratase and a GDP-L-fucose-synthase or a N-acetylhexosamine-1-kinase, a mannose-1-phosphate guanylyl-transferase, a GDP-mannose 4,6-dehydratase and a GDP-L-fucose-synthase;

B) producing guanosine 5'-diphospho-β-L-fucose from guanosine and fucose in the presence of the set of enzymes, polyphosphate, adenosine triphosphate and the co-solvent; and D) producing a fucosylated saccharide, fucosylated glycopeptide, fucosylated glycoprotein, fucosylated protein, fucosylated peptide or fucosylated small molecule from guanosine 5'-diphospho-β-l-fucose and a saccharide, glycopeptide, glycoprotein, protein, peptide or small molecule by forming an O-glycosidic bond between guanosine 5'-diphospho-β-l-fucose and an available hydroxyl group of the saccharide, glycopeptide, glycoprotein, protein, peptide or small molecule in the presence of a fucosyltransferase, wherein at least one enzyme of the set of enzymes is immobilized on a solid support.

In one embodiment, fucosylated milk saccharides are produced by the inventive methods described herein. Thus, in one embodiment the inventive method comprises the following steps:

A) providing a solution comprising
  (i) guanosine and L-fucose,
  (ii) polyphosphate, adenosine triphosphate and a co-solvent for solubilizing guanosine; and
  providing a set of enzymes comprising a guanosine kinase, a polyphosphate kinase, a fucosyltransferase and a L-fucokinase/L-fucose-1-phosphate guanylyltransferase;

B) producing guanosine 5'-diphospho-β-L-fucose from guanosine and fucose in the presence of the set of enzymes, polyphosphate, adenosine triphosphate and the co-solvent; and D) producing a fucosylated milk saccharide from guanosine 5'-diphospho-β-L-fucose and a milk saccharide by forming an O-glycosidic bond between guanosine 5'-diphospho-β-L-fucose and an available hydroxyl group of the milk saccharide, in the presence of a fucosyltransferase.

In one embodiment, fucosylated milk saccharides are produced by the inventive methods described herein. Thus, in one embodiment the inventive method comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, D) producing a fucosylated milk saccharide from guanosine 5'-diphospho-β-L-fucose and a milk saccharide by forming an O-glycosidic bond between guanosine 5'-diphospho-β-L-fucose and an available hydroxyl group of the milk saccharide, in the presence of a fucosyltransferase.

Preferably the fucosylated milk saccharides are selected from the group comprising 2'-fucosyllactose, 3-fucosyllactose, lacto-N-fucopentaose I, lacto-N-fucopentaose III, lacto-N-difucohexaose I and lacto-N-difucohexaose II (see FIG. 6).

In a preferred embodiment, 2'-fucosyllactose is produced by the inventive methods described herein (FIG. 10). Thus, in one embodiment the inventive method comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, D) producing 2'-fucosyllactose from guanosine 5'-diphospho-β-L-fucose and lactose by forming an O-glycosidic bond between guanosine 5'-diphospho-β-L-fucose and an available hydroxyl group of the lactose, in the presence of a fucosyl-transferase.

In preferred embodiment, 2'-fucosyllactose is produced by the inventive methods described herein. Thus, in one embodiment the inventive method comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
D) producing 2'-fucosyllactose from guanosine 5'-diphospho-β-L-fucose and lactose by forming an O-glycosidic bond between guanosine 5'-diphospho-β-L-fucose and an available hydroxyl group of the lactose, in the presence of type 1 galactoside-alpha-(1,2)-fucosyl-transferase.

In preferred embodiment, the method for producing 2'-fucosyllactose comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
D) producing 2'-Fucosyllactose from guanosine 5'-diphospho-β-L-fucose and lactose by forming an O-glycosidic bond between guanosine 5'-diphospho-β-L-fucose and an available hydroxyl group of the lactose, in the presence of type 1 galactoside-alpha-(1,2)-fucosyl-transferase; and
E) recycling the in-situ formed guanosine diphosphate to form guanosine triphosphate.

In a preferred embodiment, 3-fucosyllactose is produced by the inventive methods described herein (FIGS. 18 and 19). Thus, in one embodiment the inventive method comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
D) producing 3-fucosyllactose from guanosine 5'-diphospho-β-L-fucose and lactose by forming an O-glycosidic bond between guanosine 5'-diphospho-β-L-fucose and an available hydroxyl group of the lactose, in the presence of a fucosyl-transferase.

In preferred embodiment, 3-fucosyllactose is produced by the inventive methods described herein. Thus, in one embodiment the inventive method comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent,
D) producing 3-fucosyllactose from guanosine 5'-diphospho-β-L-fucose and lactose by forming an O-glycosidic bond between guanosine 5'-diphospho-β-L-fucose and an available hydroxyl group of the lactose, in the presence of 3/4-fucosyltransferase.

In preferred embodiment, 3-fucosyllactose is produced by the inventive methods described herein. Thus, in one embodiment the inventive method comprises the following steps:

A) providing a solution comprising
  (i) guanosine and D-mannose
  (ii) polyphosphate, adenosine triphosphate and a co-solvent for solubilizing guanosine; and
  providing a set of enzymes comprising a guanosine kinase, a polyphosphate kinase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent or from guanosine and D-mannose in the presence of the set of enzymes, polyphosphate, adenosine triphosphate and the co-solvent, D) producing 3-fucosyllactose from guanosine 5'-diphospho-β-L-fucose and lactose by forming an O-glycosidic bond between guanosine 5'-diphospho-β-L-fucose and an available hydroxyl group of the lactose, in the presence of 3/4-fucosyltransferase.

In preferred embodiment, the method for producing 3-fucosyllactose comprises the following steps:

A) providing a solution comprising
  (i) guanosine and L-fucose or guanosine and D-mannose
  (ii) polyphosphate, adenosine triphosphate and a co-solvent for solubilizing guanosine; and
  providing a set of enzymes comprising a guanosine kinase, a polyphosphate kinase, and in case of L-fucose a L-fucokinase/L-fucose-1-phosphate guanylyltransferase or in case of D-mannose either (a) a glucokinase, phosphomanno-mutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and L-fucose in the presence of the set of enzymes, polyphosphate, adenosine triphosphate and the co-solvent or from guanosine and D-mannose in the presence of the set of enzymes, polyphosphate, adenosine triphosphate and the co-solvent, D) producing 3-fucosyllactose from guanosine 5'-diphospho-β-L-fucose and lactose by forming an O-glycosidic bond between guanosine 5'-diphospho-β-L-fucose and an available hydroxyl group of the lactose, in the presence of 3/4-fucosyltransferase; and E) recycling the in-situ formed guanosine diphosphate to form guanosine triphosphate.

Due to the recycling of the by-product guanosine diphosphate in the inventive fucosylation methods described herein, lower amounts of guanosine are required in the solution provided in step A). Thus, in one embodiment, the molar ratio of guanosine to L-fucose or guanosine to D-mannose is between 0.01 and 0.5, more preferably between 0.02 and 0.5, more preferably between 0.03 and 0.4, more preferably between 0.03 and 0.3 and most preferably, between 0.05 and 0.2. In one embodiment, the molar ratio of guanosine to L-fucose or guanosine to D-mannose is 0.05. In one embodiment, the molar ratio of guanosine to L-fucose or guanosine to D-mannose is 0.1. In one embodiment, the molar ratio of guanosine to L-fucose or guanosine to D-mannose is 0.2. In one embodiment, the molar ratio of guanosine to L-fucose or guanosine to D-mannose is 0.5.

In a preferred embodiment the inventive method comprises the following steps:

A) providing a solution comprising
  (i) guanosine and D-mannose
  (ii) polyphosphate, adenosine triphosphate, NADPH, L-glutamate and a co-solvent for solubilizing guanosine; and
  providing a set of enzymes comprising a guanosine kinase, a polyphosphate kinase, a glutamate dehydrogenase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate and the co-solvent or from guanosine and D-mannose in the presence of the set of enzymes, polyphosphate, adenosine triphosphate and the co-solvent, D) producing 3-fucosyllactose from guanosine 5'-diphospho-β-L-fucose and lactose by forming an O-glycosidic bond between guanosine 5'-diphospho-β-L-fucose and an available hydroxyl group of the lactose, in the presence of 3/4-fucosyltransferase, E) recycling the in-situ formed guanosine diphosphate to form guanosine triphosphate, F) regenerating NADPH from in situ formed NADP+ being catalyzed by a glutamate dehydrogenase.

In a preferred embodiment the inventive method comprises the following steps:

A) providing a solution comprising
  (i) guanosine and D-mannose
  (ii) polyphosphate, adenosine triphosphate, NADPH, D-glucose and a co-solvent for solubilizing guanosine; and
  providing a set of enzymes comprising a guanosine kinase, a polyphosphate kinase, a glucose-6-phosphate dehydrogenase, and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;

B) producing guanosine 5'-diphospho-β-L-fucose from guanosine and D-mannose in the presence of the set of enzymes, polyphosphate, adenosine triphosphate, NADPH, D-glucose and the co-solvent or from guanosine and D-mannose in the presence of the set of enzymes, polyphosphate, adenosine triphosphate and the co-solvent, D) producing 3-fucosyllactose from guanosine 5'-diphospho-β-L-fucose and lactose by forming an O-glycosidic bond between guanosine 5'-diphospho-β-L-fucose and an available hydroxyl group of the lactose, in the presence of 3/4-fucosyltransferase, E) recycling the in-situ formed guanosine diphosphate to form guanosine triphosphate, F) regenerating NADPH from in situ formed NADP+ being catalyzed by a glutamate dehydrogenase.

Due to the recycling of the by-product NADP+ in the inventive methods for producing GDP-fucose from guanosine and D-mannose described herein, lower amounts of NADPH are required in the solution provided in step A). Thus, in one embodiment, the molar ratio of NADPH to D-mannose is between 0.01 and 0.5, more preferably between 0.02 and 0.5, more preferably between 0.03 and 0.4, more preferably between 0.03 and 0.3 and most preferably, between 0.05 and 0.2. In one embodiment, the molar ratio of NADPH to D-mannose is 0.05. In one embodiment, the molar ratio of NADPH to D-mannose is 0.1. In one embodiment, the molar ratio of NADPH to D-mannose is 0.2. In one embodiment, the molar ratio of NADPH to D-mannose is 0.5.

Production of L-Fucose

Since L-Fucose can be considered as an expensive sugar (in very large scales) the synthesis of L-fucose from D-mannose is further provided with the method of the present invention. First GDP-fucose is produced from D-mannose and guanosine as described herein. Afterwards, by addition of a fucosyltransferase (EC 2.4.1.344 or EC 2.4.1.69) or a fucosidase (EC 3.2.1.51) without addition of any acceptor—GDP-fucose will be hydrolyzed to fucose, since transferase can work reversibly. Reaction scheme is shown in FIG. 9. Thus, L-fucose can be produced from low cost substrates such as D-mannose and guanosine.

Alternatively, L-fucose is produced simply by heating the guanosine 5'-diphospho-β-L-fucose at the temperature in a range of 80 to 100° C. as described in the Example 10. Preferably the guanosine 5'-diphospho-β-L-fucose is heated at this temperature for 0.5 to 3 hours, preferably 0.5 to 2 hours, more preferably 0.5 to 1.5 hours, most preferably for 1 hour.

Thus, in one embodiment, L-Fucose is produced by the inventive method as described herein starting from guanosine and D-mannose. Thus, in one embodiment the inventive method comprises the following steps:
A) providing a solution comprising
   (i) guanosine and D-mannose
   (ii) polyphosphate, adenosine triphosphate and a co-solvent for solubilizing guanosine; and
   providing a set of enzymes comprising a guanosine kinase, a polyphosphate kinase; and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
D) producing L-fucose from guanosine 5'-diphospho-β-L-fucose in the presence of a fucosyltransferase and in the absence of an acceptor; or producing L-fucose by heating guanosine 5'-diphospho-β-L-fucose at a temperature in a range of 80 to 100° C.

Thus, in one embodiment, L-Fucose is produced by the inventive method as described herein starting from guanosine and D-mannose. Thus, in one embodiment the inventive method comprises the following steps:
A) providing a solution comprising
   (i) guanosine and D-mannose
   (ii) polyphosphate, adenosine triphosphate and a co-solvent for solubilizing guanosine; and
   providing a set of enzymes comprising a guanosine kinase, a polyphosphate kinase; and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
D) producing L-fucose from guanosine 5'-diphospho-β-L-fucose in the presence of type 1 galactoside-alpha-(1,2)-fucosyltransferase and in the absence of an acceptor, or
   producing L-fucose by heating guanosine 5'-diphospho-β-L-fucose at a temperature in a range of 80 to 100° C.

Thus, in one embodiment the inventive method comprises the following steps:
A) providing a solution comprising
   (i) guanosine and D-mannose
   (ii) polyphosphate, adenosine triphosphate and a co-solvent for solubilizing guanosine; and
   providing a set of enzymes comprising a guanosine kinase, a polyphosphate kinase; and either (a) a glucokinase, phosphomannomutase, a mannose-1-phosphate guanylyltransferase, a GDP-mannose-4,6-dehydratase and a GDP-L-fucose-synthase or (b) an N-acetylhexosamine-1-kinase, a mannose-1-phosphate guanylyltransferase, a GDP-mannose 4,6-dehydratase and a GDP-L-fucose-synthase;
B) producing guanosine 5'-diphospho-β-L-fucose from guanosine and D-mannose in the presence of the set of enzymes, polyphosphate, adenosine triphosphate and the co-solvent,
D) producing L-fucose from guanosine 5'-diphospho-β-L-fucose in the presence of type 1 galactoside-alpha-(1,2)-fucosyltransferase and in the absence of an acceptor, or
   producing L-fucose by heating guanosine 5'-diphospho-β-L-fucose at a temperature in a range of 80 to 100° C., and
E) recycling the in-situ formed guanosine diphosphate to form guanosine triphosphate.

Due to the recycling of the by-product guanosine diphosphate in the inventive fucosylation methods described herein, lower amounts of guanosine are required in the solution provided in step A). Thus, in one embodiment, the molar ratio of guanosine to L-fucose or guanosine to D-mannose is between 0.01 and 0.5, more preferably between 0.02 and 0.5, more preferably between 0.03 and 0.4, more preferably between 0.03 and 0.3 and most preferably, between 0.05 and 0.2. In one embodiment, the molar ratio of guanosine to L-fucose or guanosine to D-mannose is 0.05. In one embodiment, the molar ratio of guanosine to L-fucose or guanosine to D-mannose is 0.1. In one embodiment, the molar ratio of guanosine to L-fucose or guanosine to D-mannose is 0.2. In one embodiment, the molar ratio of guanosine to L-fucose or guanosine to D-mannose is 0.5.

As used herein, the term "acceptor" refers to any molecule or macromolecule, including a saccharide, peptide or protein that is capable of being fucosylated by a fucosyltransferase, i.e. acting as a substrate in the reaction catalyzed by a fucosyl-transferase as described herein. Thus, the acceptor prevents the hydrolysis of GDP-fucose by fucosyltransferase in aqueous media. Particularly, the acceptor is a glycosyl acceptor which is nucleophilic. Preferably, the glycosyl acceptor has an oxygen-carbon-, nitrogen-, or sulfur-based nucleophilic group which can form a covalent glycosidic bond with the fucosyl moiety of GDP-fucose.

In any of the above-described inventive methods, preferably the glucokinase comprises at least 85% of an amino acid sequence as set forth in SEQ ID NO: 1; the phosphomannomutase comprises at least 85% of an amino acid sequence set forth in SEQ ID NO: 2; the N-acetylhexosamine-1-kinase comprises at least 85% of an amino acid sequence set forth in SEQ ID NO: 3; the mannose-1- phosphate guanyltransferase comprises at least 85% of an amino acid sequence set forth in SEQ ID NO: 4; the GDP-mannose-4,6-dehydratase comprises at least 85% of an amino acid sequence set forth in SEQ ID NO: 5; the GDP-L-fucose-synthase comprises at least 85% of an amino acid sequence set forth in SEQ ID NO: 6; the L-fucokinase comprises at least 85% of an amino acid sequence set forth in SEQ ID NO: 7; the guanosine kinase comprises at least 85% of an amino acid sequence set forth in SEQ ID NO: 8; the polyphosphate kinase comprises any of at least 85% of amino acid sequences set forth in SEQ ID NO: 9 (2D-PPK2), and SEQ ID NO: 14 (PPK3); the pyrophosphatase comprises at least 85% of an amino acid sequence set forth in SEQ ID NO: 10; the guanylate kinase (GMK) comprises at least 85% of an amino acid sequence set forth in SEQ ID NO: 11; the glutamate dehydrogenase comprises at least 85% of an amino acid sequence set forth in SEQ ID NO: 12; the glucose-6-phosphate-dehydrogenase comprises at least 85% of an amino acid sequence set forth in SEQ ID NO: 13; the glucose dehydrogenase comprises at least 85% of an amino acid sequence set forth in SEQ ID NO: 15; the fucosyltransferase comprises at least 85% of an amino acid sequence set forth in SEQ ID NO: 16 (3/4FT).

Also preferably, in any of the above-described inventive methods, the glucokinase comprises at least 90% of an amino acid sequence as set forth in SEQ ID NO: 1; the phosphomannomutase comprises at least 90% of an amino acid sequence set forth in SEQ ID NO: 2; the N-acetylhexosamine-1-kinase comprises at least 90% of an amino acid sequence set forth in SEQ ID NO: 3; the mannose-1-phosphate guanyltransferase comprises at least 90% of an amino acid sequence set forth in SEQ ID NO: 4; the GDP-mannose-4,6-dehydratase comprises at least 90% of an amino acid sequence set forth in SEQ ID NO: 5; the GDP-L-fucose-synthase comprises at least 90% of an amino acid sequence set forth in SEQ ID NO: 6; the L-fucokinase comprises at least 90% of an amino acid sequence set forth in SEQ ID NO: 7; the guanosine kinase comprises at least 90% of an amino acid sequence set forth in SEQ ID NO: 8; the polyphosphate kinase comprises any of at least 90% of amino acid sequences set forth in SEQ ID NO: 9 (2D-PPK2), and SEQ ID NO: 14 (PPK3); the pyrophosphatase comprises at least 90% of an amino acid sequence set forth in SEQ ID NO: 10; the guanylate kinase (GMK) comprises at least 90% of an amino acid sequence set forth in SEQ ID NO: 11; the glutamate dehydrogenase comprises at least 90% of an amino acid sequence set forth in SEQ ID NO: 12; the glucose-6-phosphate-dehydrogenase comprises at least 90% of an amino acid sequence set forth in SEQ ID NO: 13; the glucose dehydrogenase comprises at least 90% of an amino acid sequence set forth in SEQ ID NO: 15; the fucosyltransferase comprises at least 90% of an amino acid sequence set forth in SEQ ID NO: 16 (3/4FT).

More preferably, in any of the above-described inventive methods, the glucokinase comprises at least 95% of an amino acid sequence as set forth in SEQ ID NO: 1; the phosphomannomutase comprises at least 95% of an amino acid sequence set forth in SEQ ID NO: 2; the N-acetylhexosamine-1-kinase comprises at least 95% of an amino acid sequence set forth in SEQ ID NO: 3; the mannose-1-phosphate guanyltransferase comprises at least 95% of an amino acid sequence set forth in SEQ ID NO: 4; the GDP-mannose-4,6-dehydratase comprises at least 95% of an amino acid sequence set forth in SEQ ID NO: 5; the GDP-L-fucose-synthase comprises at least 95% of an amino acid sequence set forth in SEQ ID NO: 6; the L-fucokinase comprises at least 95% of an amino acid sequence set forth in SEQ ID NO: 7; the guanosine kinase comprises at least 95% of an amino acid sequence set forth in SEQ ID NO: 8; the polyphosphate kinase comprises any of at least 95% of amino acid sequences set forth in SEQ ID NO: 9 (2D-PPK2), and SEQ ID NO: 14 (PPK3); the pyrophosphatase comprises at least 95% of an amino acid sequence set forth in SEQ ID NO: 10; the guanylate kinase (GMK) comprises at least 95% of an amino acid sequence set forth in SEQ ID NO: 11; the glutamate dehydrogenase comprises at least 95% of an amino acid sequence set forth in SEQ ID NO: 12; the glucose-6-phosphate-dehydrogenase comprises at least 95% of an amino acid sequence set forth in SEQ ID NO: 13; the glucose dehydrogenase comprises at least 95% of an amino acid sequence set forth in SEQ ID NO: 15; the fucosyltransferase comprises at least 95% of an amino acid sequence set forth in SEQ ID NO: 16 (3/4FT).

Still more preferably, in any of the above-described inventive methods, the glucokinase comprises at least 98% of an amino acid sequence as set forth in SEQ ID NO: 1; the phosphomannomutase comprises at least 98% of an amino acid sequence set forth in SEQ ID NO: 2; the N-acetylhexosamine-1-kinase comprises at least 98% of an amino acid sequence set forth in SEQ ID NO: 3; the mannose-1-phosphate guanyltransferase comprises at least 98% of an amino acid sequence set forth in SEQ ID NO: 4; the GDP-mannose-4,6-dehydratase comprises at least 98% of an amino acid sequence set forth in SEQ ID NO: 5; the GDP-L-fucose-synthase comprises at least 98% of an amino acid sequence set forth in SEQ ID NO: 6; the L-fucokinase comprises at least 98% of an amino acid sequence set forth in SEQ ID NO: 7; the guanosine kinase comprises at least 98% of an amino acid sequence set forth in SEQ ID NO: 8; the polyphosphate kinase comprises any of at least 98% of amino acid sequences set forth in SEQ ID NO: 9 (2D-PPK2), and SEQ ID NO: 14 (PPK3); the pyrophosphatase comprises at least 85% of an amino acid sequence set forth in SEQ ID NO: 10; the guanylate kinase (GMK) comprises at least 98% of an amino acid sequence set forth in SEQ ID NO: 11; the glutamate dehydrogenase comprises at least 98% of an amino acid sequence set forth in SEQ ID NO: 12; the glucose-6-phosphate-dehydrogenase comprises at least 98% of an amino acid sequence set forth in SEQ ID NO: 13; the glucose dehydrogenase comprises at least 98% of an amino acid sequence set forth in SEQ ID NO: 15; the fucosyltransferase comprises at least 98% of an amino acid sequences set forth in SEQ ID NO: 16 (3/4FT).

Most preferably, in any of the above-described inventive methods, the glucokinase comprises an amino acid sequence as set forth in SEQ ID NO: 1; the phosphomannomutase comprises an amino acid sequence set forth in SEQ ID NO: 2; the N-acetylhexosamine-1-kinase comprises an amino acid sequence set forth in SEQ ID NO: 3; the mannose-1-phosphate guanyltransferase comprises an amino acid sequence set forth in SEQ ID NO: 4; the GDP-mannose-4,6-dehydratase comprises an amino acid sequence set forth in SEQ ID NO: 5; the GDP-L-fucose-synthase comprises an amino acid sequence set forth in SEQ ID NO: 6; the L-fucokinase comprises an amino acid sequence set forth in SEQ ID NO: 7; the guanosine kinase comprises an amino acid sequence set forth in SEQ ID NO: 8; the polyphosphate kinase comprises any of amino acid sequences set forth in SEQ ID NO: 9 (2D-PPK2), and SEQ ID NO: 14 (PPK3); the pyrophosphatase comprises an amino acid sequence set forth in SEQ ID NO: 10; the guanylate kinase (GMK) comprises an amino acid sequence set forth in SEQ ID NO: 11; the glutamate dehydrogenase comprises an amino acid sequence set forth in SEQ ID NO: 12; the glucose-6-phosphatedehydrogenase comprises an amino acid sequence set forth in SEQ ID NO: 13; the glucose dehydrogenase comprises an amino acid sequence set forth in SEQ ID NO: 15; the fucosyltransferase comprises an amino acid sequence set forth in SEQ ID NO: 16 (3/4FT).

Figure 1:
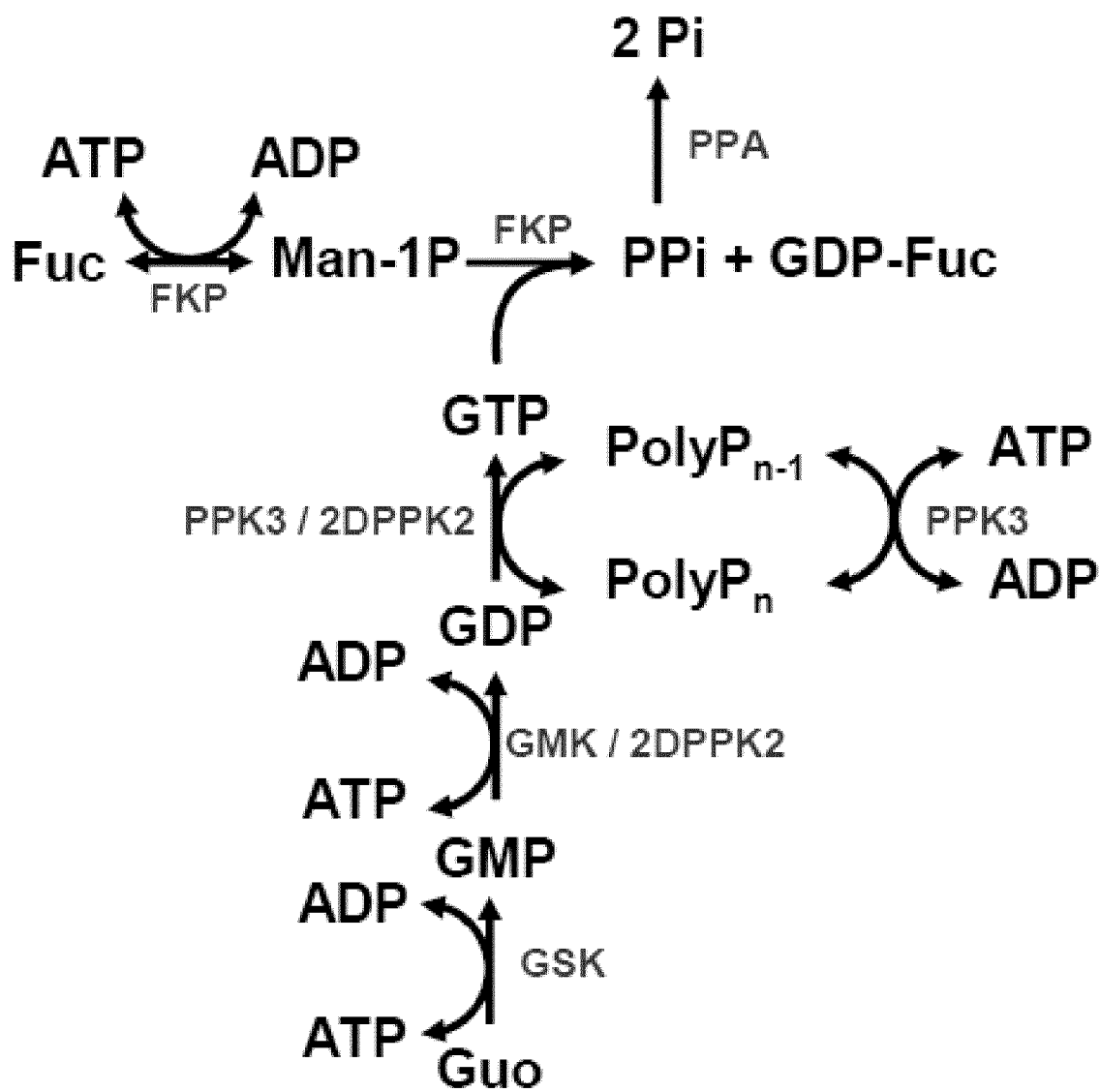
FIG. 1: shows the reaction pathway of the inventive method for producing GDP-fucose, which consists of (a) the formation of fucose-1-phosphate (Fuc-1-P) from L-fucose and ATP, (b) the formation of guanosine triphosphate (GTP) from guanosine and polyphosphate, and (c) the reaction of fucose-1-phosphate with guanosine triphosphate to GDP-fucose.
Figure 2:
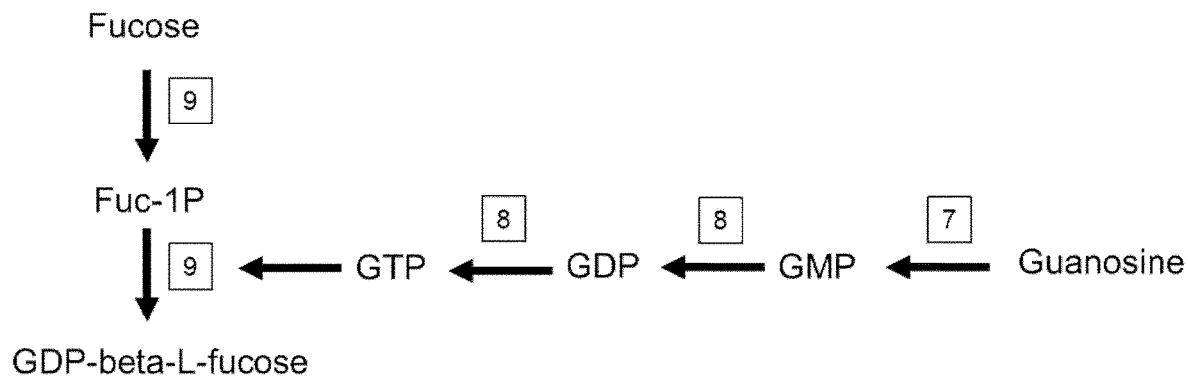
FIG. 2: shows an exemplary reaction scheme of the inventive method for producing GDP-fucose, which consists of (a) the formation of fucose-1-phosphate (Fuc-1-P) from L-fucose and ATP catalyzed by fucokinase (9), (b) the formation of guanosine triphosphate (GTP) from guanosine and polyphosphate catalyzed by guanosine kinase/inosine kinase (7) and polyphosphate kinase (8), and (c) the reaction of fucose-1-phosphate with guanosine triphosphate to GDP-fucose catalyzed by fucose-1-phosphate guanylyltransferase (9)
Figure 3:
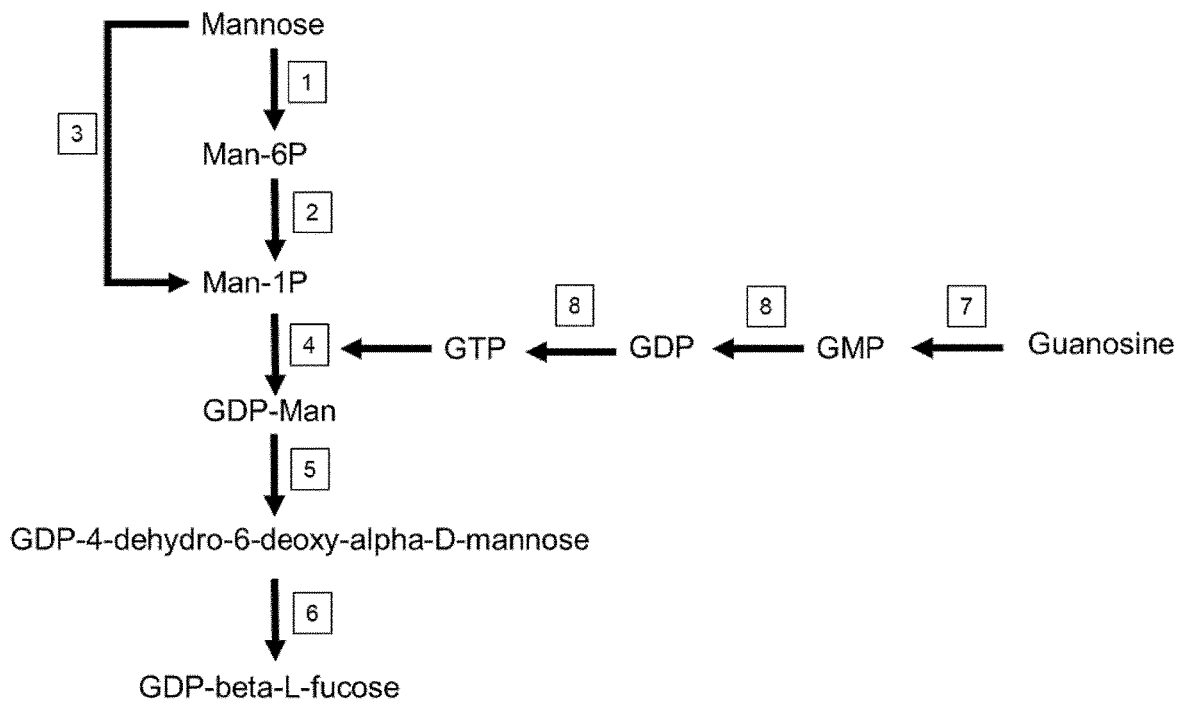
FIG. 3: shows an exemplary reaction scheme of the inventive method for producing GDP-fucose, which consists of (a) the formation of mannose-1-phosphate (Man-1-P) from D-mannose and ATP catalyzed by either glucokinase (1) and phosphomannomutase (2) or N-acetylhexosamine-1-kinase (3), (b) the formation of guanosine triphosphate (GTP) from guanosine and polyphosphate catalyzed by guanosine kinase/inosine kinase (7) and polyphosphate kinase (8), and (c) the reaction of mannose-1-phosphate with guanosine triphosphate to GDP-mannose catalyzed by mannose-1-phosphate guanylyltransferase (4) and (d) formation of GDP-4-dehydro-6-deoxy-alpha-D-mannose from GDP-mannose catalyzed by GDP-mannose-4,6-dehydratase (5) and (e) formation of GDP-fucose from GDP-4-dehydro-6-deoxy-alpha-D-mannose and NADPH catalyzed by GDP-L-fucose synthase (6).

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Abbreviations and Acronyms

ADP adenosine 5'-diphosphate
ATP adenosine 5'-triphosphate
Fuc L-fucose
GSK guanosine kinase
GDP guanosine 5'-diphosphate
GDH glucose dehydrogenase; glucose-1-dehydrogenase
GLDH glutamate dehydrogenase
G6PDH glucose-6-phosphate-dehydrogenase
GMD GDP-D-mannose-4,6-dehydratase
GMK guanylate kinase
GMP guanosine 5'-monophosphate
GLK glucokinase
GTP guanosine 5'-triphosphate
GUO guanosine
Lac D-lactose
Man D-mannose
ManB phosphomannomutase
ManC mannose-1-phosphate guanyltransferase
NADP nicotinamide adenine dinucleotide phosphate
NADPH reduced nicotinamide adenine dinucleotide phosphate
NAHK N-acetylhexosamine-1-kinase
PolyP polyphosphate
PPi pyrophosphate
Pi phosphate
PPK2 polyphosphate kinase 2
PPK3 polyphosphate kinase 3
2D-PPK2 2-domain polyphosphate kinase 2
FKP L-fucokinase/L-fucose-1-phosphate guanylyltransferase
PmPpA *Pasteurella multocida* inorganic pyrophosphatase (PPA)
WCAG GDP-4-keto-6-deoxymannose-3,5-epimerase-4-reductase
3/4FT α-1-3/4-fucosyltransferase Chemicals & Reagents Unless otherwise stated, all chemicals and reagents were acquired from Sigma-Aldrich, and were of the highest purity available. Solid supports were obtained from Resindion, ChiralVision, ROhm GmbH & Co. KG and micromod GmbH.

Example 1

Preparation of Enzymes

The genes encoding for the enzymes GSK, PPK2, FKP and PmPpA were cloned into standard expression vectors as listed in Table 1. The expression vectors were transformed into *E. coli* BL21 Gold (DE3).

TABLE 1

| Enzyme | Source | Plasmid | Inducer | Expression host |
|---|---|---|---|---|
| guanosine kinase (GSK) | *Exiguobacterium acetylicum* | pET-28a(+) | IPTG | *E. coli* BL21 Gold (DE3) |
| polyphosphate kinase (2D-PPK2) | *Pseudomonas aeruginosa* | pET-28a(+) | IPTG | *E. coli* BL21 Gold (DE3) |
| L-fucokinase/L-fucose-1-phosphate-guanylyltransferase (FKP) | *Bacteroides fragilis* | pET-100/D-TOPO | IPTG | *E. coli* BL21 Gold (DE3) |
| inorganic pyrophosphatase (PmPpA) | *Pasteurella multocida* | pET-28a(+) | IPTG | *E. coli* BL21 Gold (DE3) |

Transformants were grown in 1 L shaking flasks with baffles in a volume of 500 ml of LB medium (lysogeny broth) supplemented with 50 µg/ml Kanamycin. The cultures were grown at 37° C. up to $OD_{600}$=0.8. The expression was induced by addition of IPTG with a final concentration of 0.5 mM to the culture. Expression time was terminated after 12-18 hours at 20° C. Biomass was separated from the medium by centrifugation at 6,000×g for 10 min. Successful expression of the respective enzyme was analyzed by SDS-PAGE following standard operating procedures (Laemmli, Nature 1970, 227, 680-685). The wet biomass was stored at −20° C.

For purification, typically 30 ml of equilibration buffer were added to 3 g of frozen biomass. The equilibration buffer contains cOmplete™ protease inhibitor cocktail at pH 7.5: 100 mM HEPES (4-(2-hydroxyethyl)-1-piperazineethanesulfonic acid), 10 mM MgCl$_2$, 5 mM MnSO$_4$, 300 mM NaCl and 5 vol % glycerol. Following thawing at 4° C. under stirring, cells were disrupted by four passages through a high pressure homogenizer (Emulsiflex C5, Avestin Inc., Ottawa, Canada) at 1,000 bar with intermediate cooling on ice. After centrifugation (45 min, 20,000×g), the supernatant was applied to an equilibrated Immobilized Metal Affinity Chromatography (IMAC) column (10 ml CV) containing Ni$^{2+}$ Sepharose™ High Performance chromatography material from Amersham Biosciences (Uppsala, Sweden). Unbound proteins were washed out using equilibration buffer. Immobilized protein was eluted in 1 ml fractions using elution buffer. Finally, the enzyme solutions were concentrated by Centrifugal Filter Units Amicon® Ultra-15 with a 50 kDa cut-off from Merck Millipore (Darmstadt, Germany). No enzyme loss was observed during the ultrafiltration. The enzymes were stored in 50% glycerol at −20° C. The protein concentration was determined by Bradford assay using BSA as standard (Bradford, Analytical Biochemistry 1976, 72(1), 248-254).

Example 2

Homogeneous Preparation of GDP-Fucose

The purified enzymes (Table 1) are mixed together with guanosine, L-fucose, ATP, polyphosphate, and HEPES buffer to the concentrations as listed in Table 2. Experiments conducted in low binding protein vials. Guanosine was solubilized in 6 vol % dimethyl sulfoxide (DMSO) prior addition to the mixture. The reaction was carried out at 30° C. in a thermomixer.

TABLE 2

| Reactants | Concentration [mmol/L] |
| --- | --- |
| guanosine | 2 |
| polyphosphate (n = 14 or 25) | 4 |
| L-fucose | 2 |
| ATP | 2 |
| HEPES Buffer | 50 |
| Mg$^{2+}$ | 2.5 |
| Mn$^{2+}$ | 2.5 |

| Enzyme | Concentration [mg/mL] |
| --- | --- |
| GSK | 0.3 |
| 2D-PPK2 | 0.7 |
| FKP | 0.2 |
| PmPpA | 0.2 |

Figure 4:
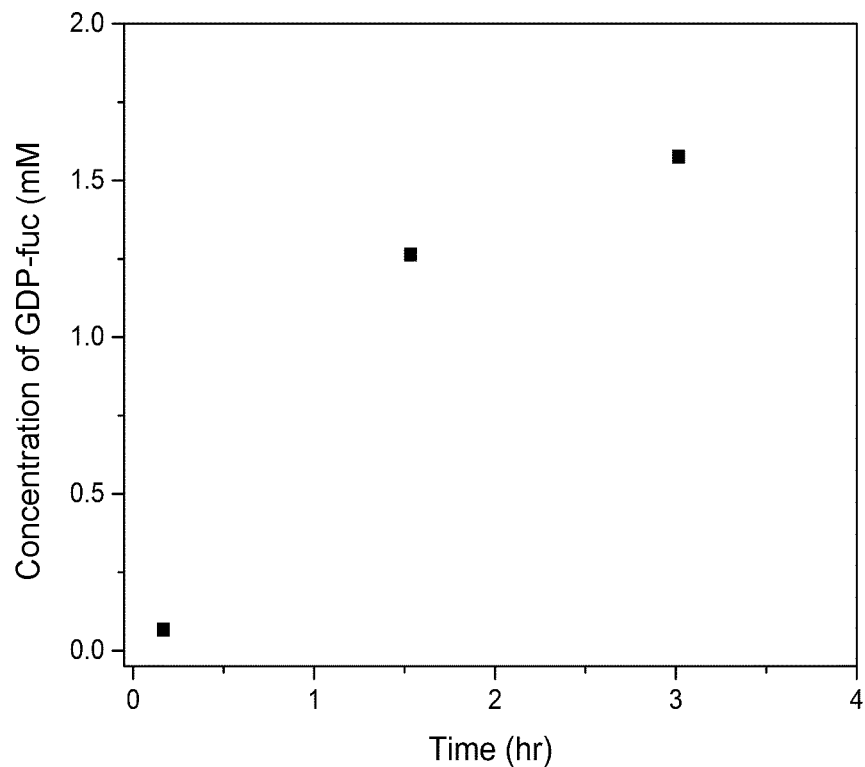
FIG. 4A: shows concentration of GDP-fucose prepared by the inventive method at different time points (see Example 3).
FIG. 4B: shows concentration of GDP-fucose prepared by the inventive method using immobilized enzymes at different time points (see example 5).
Figure 4:
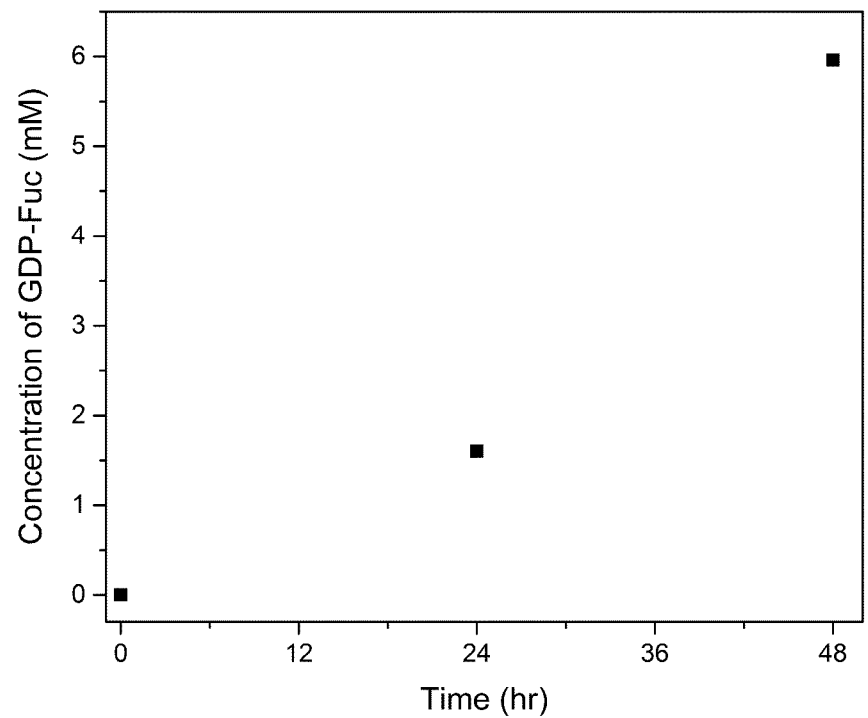
Figure 5:
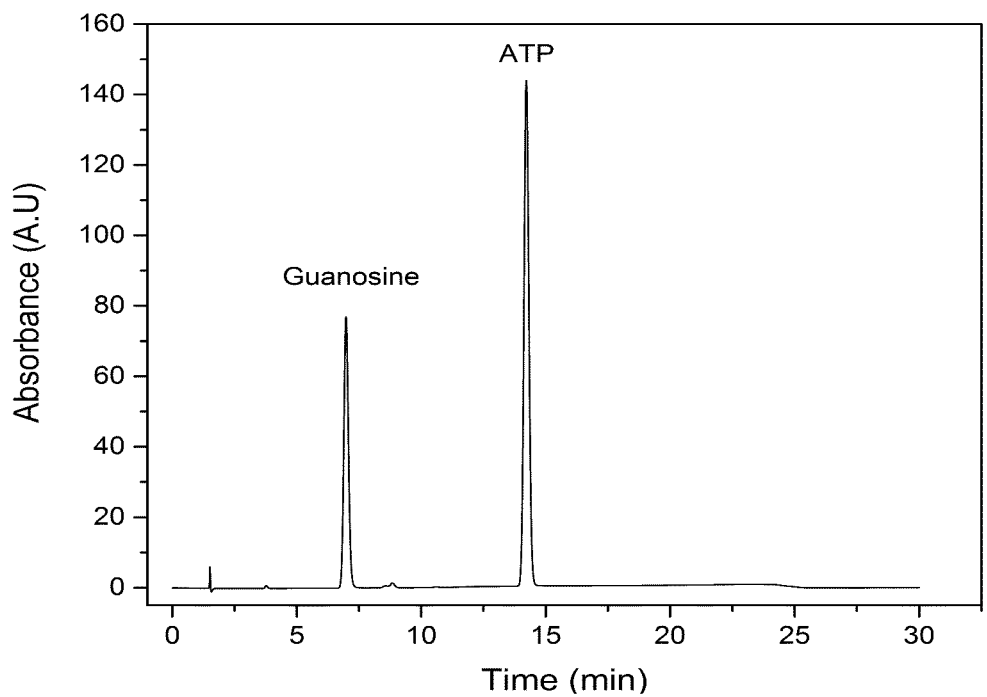
FIG. 5A: shows a chromatogram of the starting material at t=0.
FIG. 5B: shows a chromatogram of the reaction mixture after 48 hours.
Figure 5:
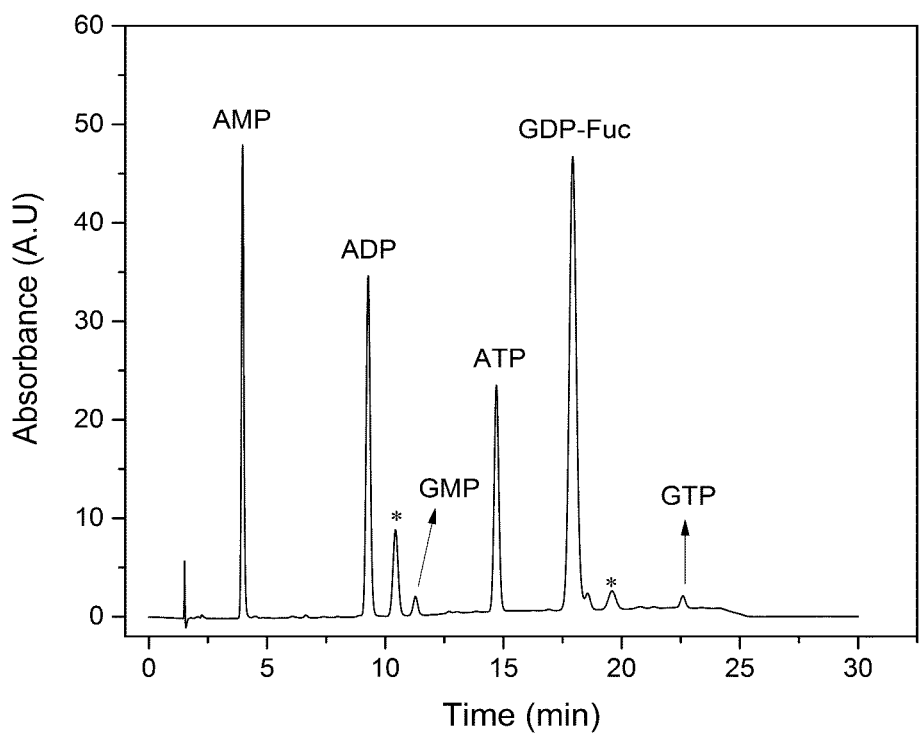
Figure 6:
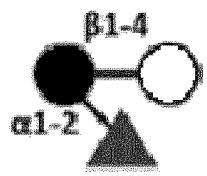
FIG. 6: shows exemplary fucosylated milk saccharides.
Figure 6:
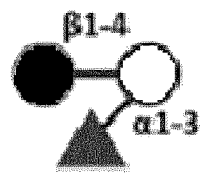
Figure 6:
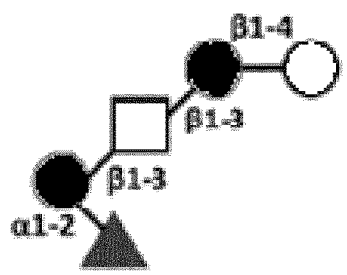
Figure 6:
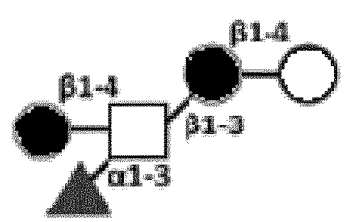
Figure 6:
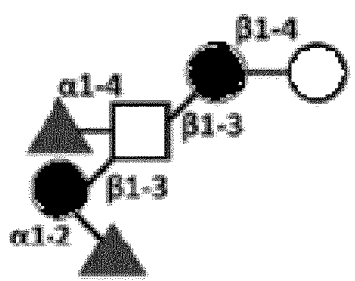
Figure 6:
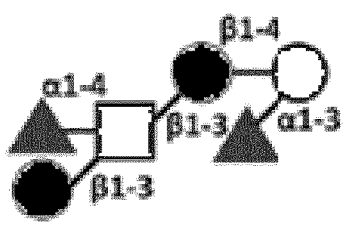

After almost three hours 90% conversion of substrate (guanosine) to GDP-fucose was obtained (See FIG. 4A). No other end-products were detected (See FIG. 5B showing a chromatogram of the reaction mixture after 48 hours).

Example 3

Failed Synthesis of GDP-Fucose

The synthesis of GDP-fucose was carried out as described in Example 2, but without adding DMSO. The reaction was carried out at 30° C. in a thermomixer and the obtained reaction mixture remained turbid. After three hours no conversion of substrate (guanosine) to GDP-fucose was observed.

This Example demonstrates that the mere combination of the two enzymatic pathways does not provide GDP-fucose.

Example 4

Immobilization of Enzymes on Solid Support

Enzymes were immobilized on the solid supports in order to allow the multiple use of the enzymes.

Cell lysates obtained in Example 1 by high pressure homogenization were centrifuged and filtered to remove cell debris. The resins: sepabeads (Resindion): EC-EP, EP403/M, EC-HFA, EC-EA/M and EC-HA; immobeads (Chiral-Vision) IB-COV-1, IB-COV2, IB-COV3, IB-ANI1, IB-ANI2, IB-ANI3, IB-ANI4, IB-CAT1, IB-ADS1, IB-ADS2, IB-ADS3 and IB-ADS4; Eupergit (Rohm GmbH & Co. KG) and magnetic particles (micromod GmbH): Nano-mag, Sicastar-6 and Sicastar-1.5 were incubated together with the enzymes for 24 hours at 4° C.

Figure 7:
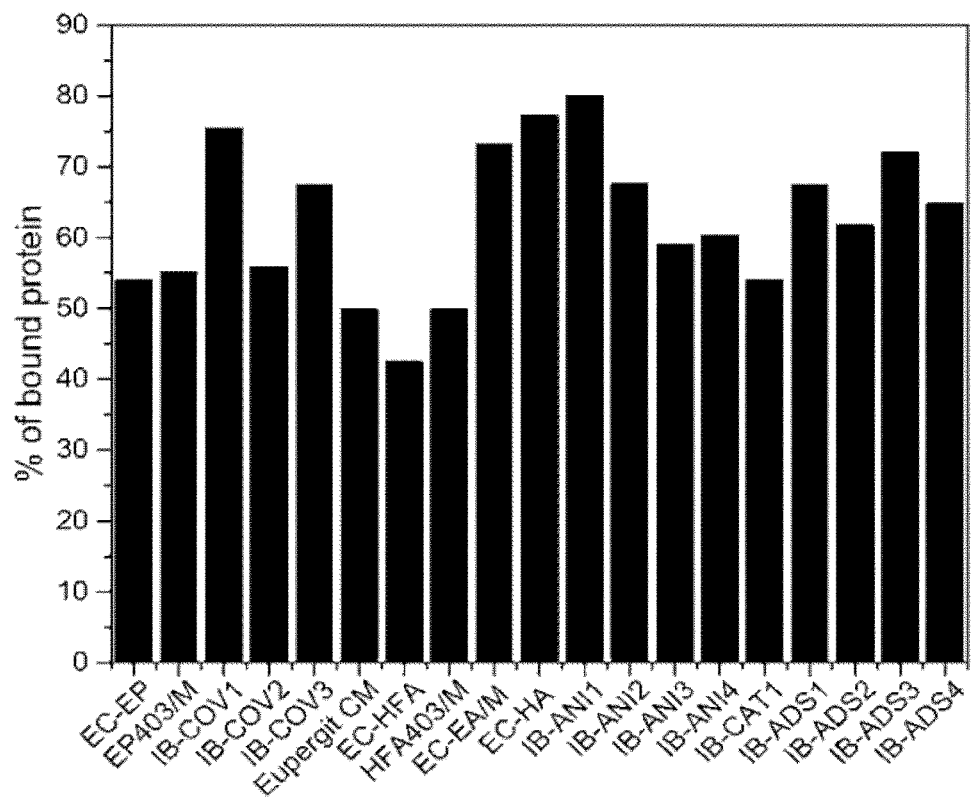
FIG. 7: shows amount of bound enzymes on solid support after incubation at 4° C. for 24 hours (see Example 4).

The protein assay was done by BCA assay. Results of total bound protein are shown in FIG. 7.

After immobilization the enzyme loaded resins were washed with buffer as described in Example 1. The resins were incubated with a solution of reactants as shown in Table 3 at 30° C. for 24 hours.

TABLE 3

| Reactants | Concentration [mmol/L] |
| --- | --- |
| guanosine | 3.9 (4 vol % DMSO) |
| polyphosphate (n = 25) | 12.5 |
| L-fucose | 5.3 |
| ATP | 12 |
| HEPES Buffer | 120 |
| MgCl$_2$ | 8 |
| MnCl$_2$ | 8 |
| NaCl | 200 |

Figure 8:
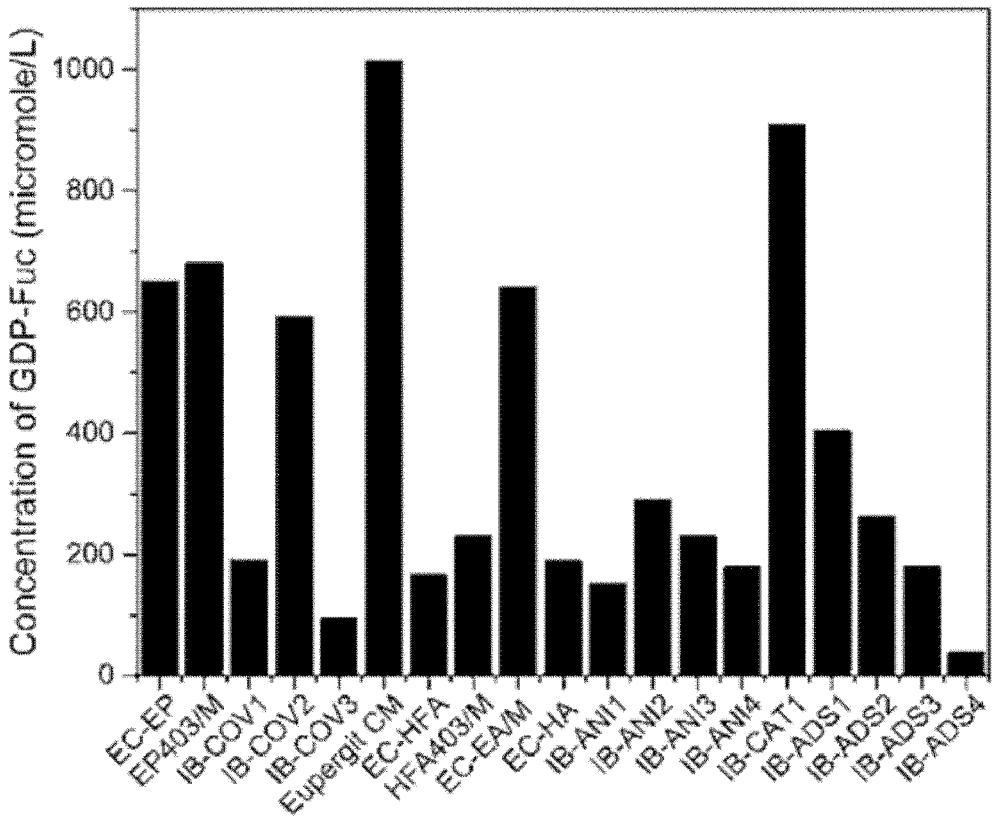
FIG. 8: shows amount of formed GDP-fucose after reaction with the immobilized enzymes for 24 hours at 30° C. (see Example 4).
Figure 9:
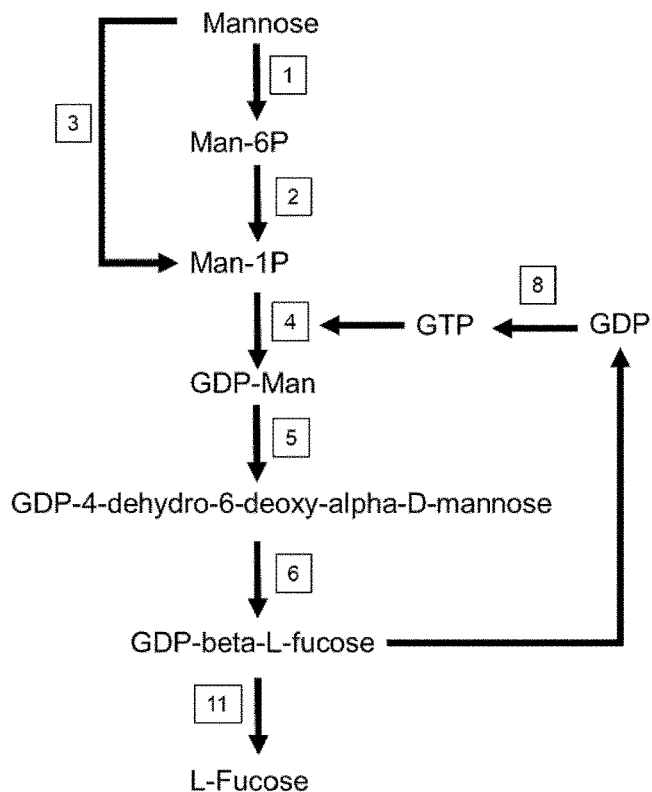
FIG. 9: shows the exemplary reaction scheme of the inventive method for producing L-fucose from guanosine and D-mannose, which consists of (a) the formation of mannose-1-phosphate (Man-1-P) from D-mannose and ATP catalyzed by either glucokinase (1) and phosphomannomutase (2) or N-acetylhexosamine-1-kinase (3), (b) the formation of guanosine triphosphate (GTP) from guanosine and polyphosphate catalyzed by guanosine kinase/inosine kinase (7) and polyphosphate kinase (8), and (c) the reaction of mannose-1-phosphate with guanosine triphosphate to GDP-mannose catalyzed by mannose-1-phosphate guanylyltransferase and (d) formation of GDP-4-dehydro-6-deoxy-alpha-D-mannose from GDP-mannose catalyzed by GDP-mannose-4,6-dehydratase and (e) formation of GDP-fucose from GDP-4-dehydro-6-deoxy-alpha-D-mannose and NADPH catalyzed by GDP-L-fucose synthase and formation of L-fucose from GDP-L-fucose catalyzed by type 1 galactoside alpha-(1,2)-fucosyltransferase in absence of an acceptor molecule.
Figure 10:
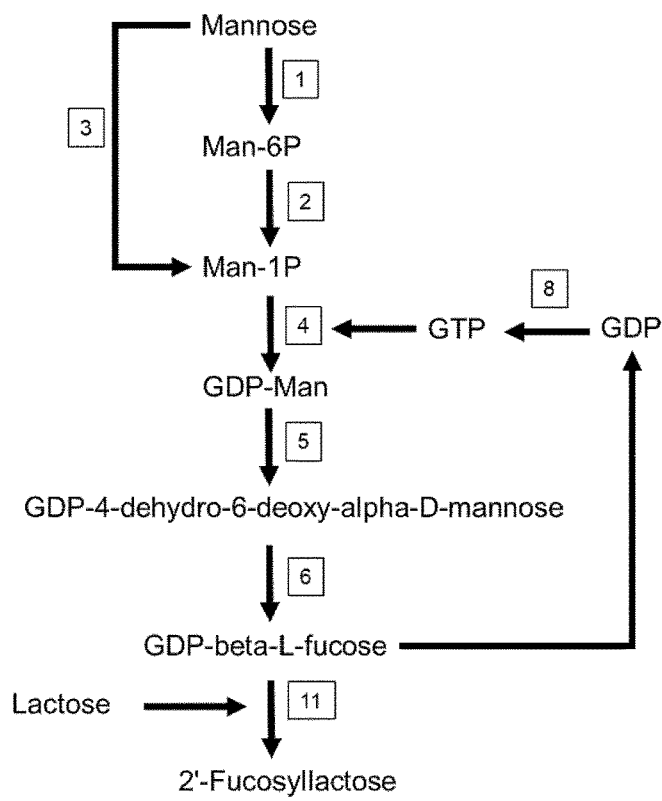
FIG. 10: shows an exemplary reaction scheme of the inventive method for producing 2'-fucosyllactose from guanosine and D-mannose, which consists of (a) the formation of mannose-1-phosphate (Man-1-P) from D-mannose and ATP catalyzed by either glucokinase (1) and phosphomannomutase (2) or N-acetylhexosamine-1-kinase (3), (b) the formation of guanosine triphosphate (GTP) from guanosine and polyphosphate catalyzed by guanosine kinase/inosine kinase (7) and poly-phosphate kinase (8), and (c) the reaction of mannose-1-phosphate with guanosine triphosphate to GDP-mannose catalyzed by mannose-1-phosphate guanylyl-transferase and (d) formation of GDP-4-dehydro-6-deoxy-alpha-D-mannose from GDP-mannose catalyzed by GDP-mannose-4,6-dehydratase and (e) formation of GDP-fucose from GDP-4-dehydro-6-deoxy-alpha-D-mannose and NADPH catalyzed by GDP-L-fucose synthase and formation of 2'-fucosyllactose from GDP-L-fucose and lactose catalyzed by type 1 galactoside alpha-(1,2)-fucosyltransferase.

The formation of GDP-fucose was observed for all loaded resins, as shown in FIG. 8.

Example 5

Heterogeneous Preparation of GDP-Fucose on Magnetic Particles

To this extent, fermentation broths (see Example 1) of 135 mL of FKP, 45 mL of PmPpA, 90 mL GSK and 90 mL of 2D-PPK2 were combined and lysed in 25 mL buffer (as described in Example 1) containing 10 mM imidazole, to obtain 0.5 mL of an enzyme mixture, which was incubated with 12.5 mg of Sicastar-6 magnetic resins. After 1 hour of incubation at 10° C., resins were washed with buffer and combined in a vial with 0.25 mL of a solution of reagents (see Table 4). The mixture was incubated at 30° C. for 48 hours.

TABLE 4

| Reactants | Concentration [mmol/L] |
| --- | --- |
| guanosine | 6 (4 vol % DMSO) |
| polyphosphate (n = 25) | 9.3 |
| L-fucose | 6 |
| ATP | 9.6 |
| HEPES Buffer | 50 |
| MgCl$_2$ | 15 |

TABLE 4-continued

| Reactants | Concentration [mmol/L] |
|---|---|
| MnCl$_2$ | 5 |
| NaCl | 30 |
| KCl | 30 |

After 48 hours nearly quantitative conversion (98%) of substrate (guanosine) to GDP-fucose was obtained (See FIG. 4B).

Example 6

Recycling of NADPH

Figure 11:
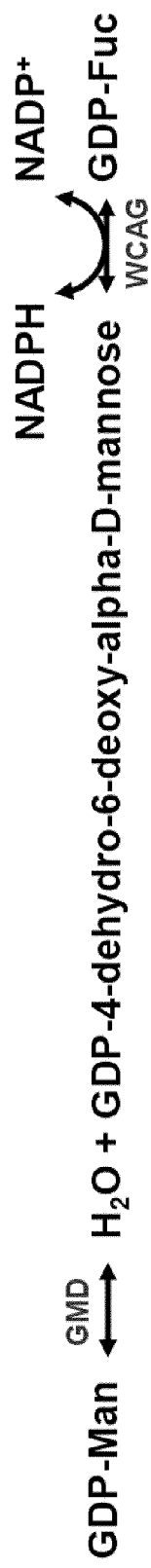
FIG. 11: shows the reaction cascade from (A1) GDP-mannose to GDP-fucose performed in Example 6-A1; (A2) GDP-mannose to GDP-fucose in presence of glucose and G6PDH as performed in Example 6-A2; and (A3) mannose and GTP to GDP-fucose in presence of glutamate and GLDH as performed in Example 6-A3. Reactions were conducted to demonstrate that NADPH recycling can drive the multi-enzyme reaction equilibrium towards the side of GDP-fucose.
Figure 11:
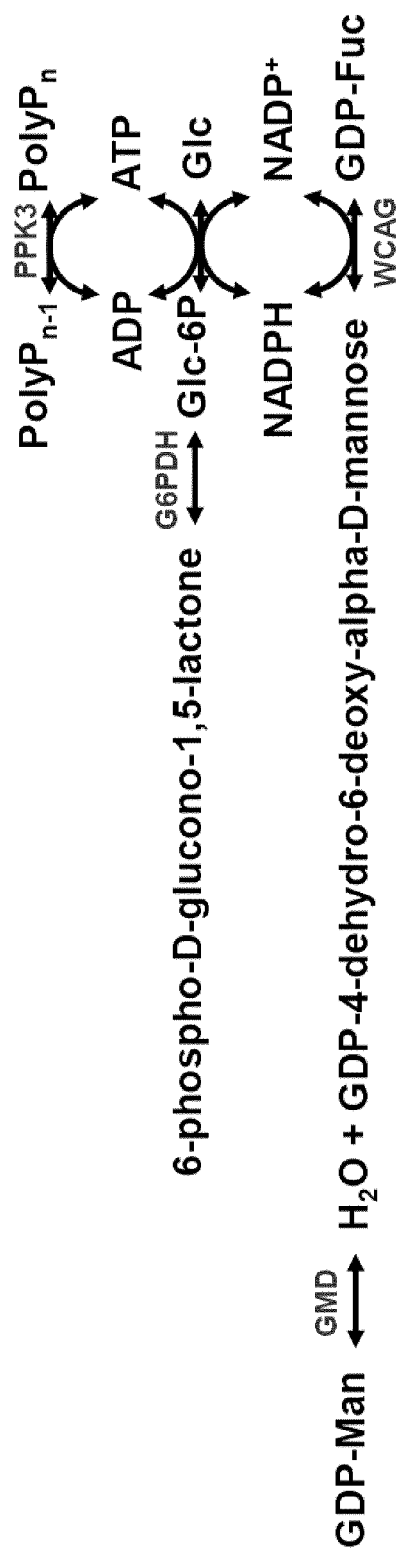
Figure 11:
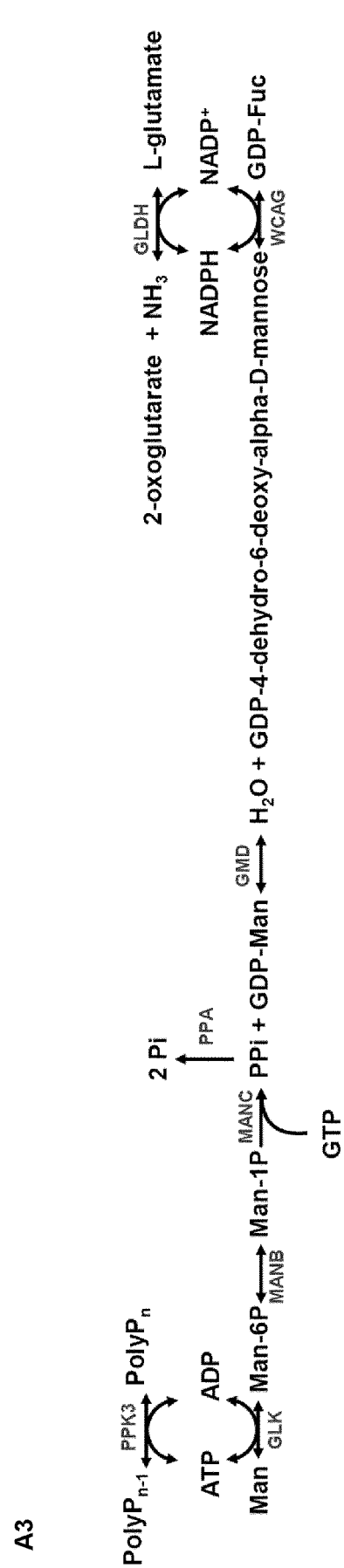
Figure 12:
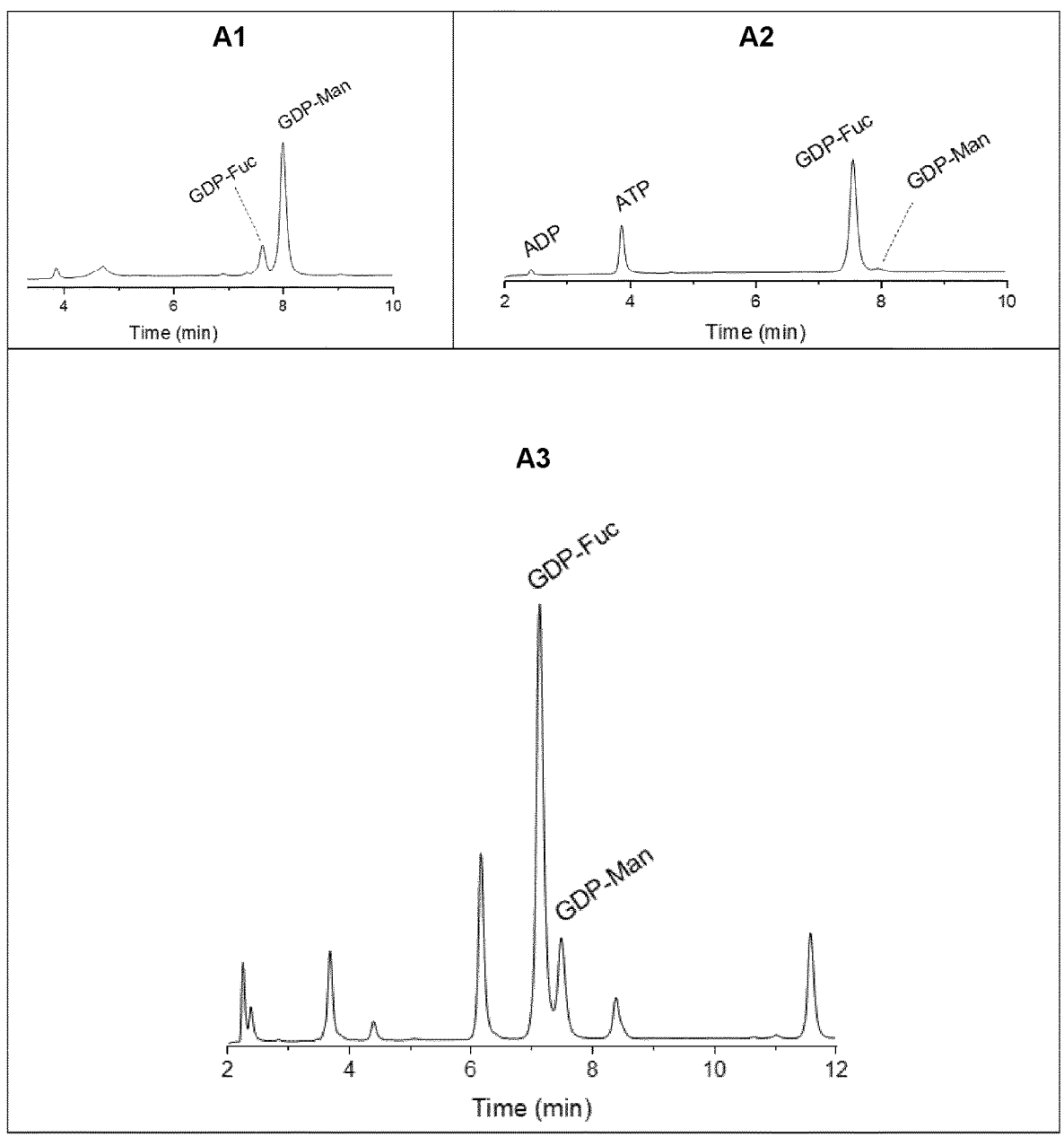
FIG. 12: shows chromatogram of reaction aliquots of reactions A1, A2 and A3 after overnight incubation). The chromatogram (A1) shows that the reaction equilibrium is on the side towards GDP-mannose. When NADPH recycling is implemented the reaction equilibrium can be driven towards GDP-fucose (see A2 and A3).

A one-pot reaction was conducted (see reaction conditions of reaction A1 in Table 5) to show that the equilibrium of the GDP-mannose 4,6-dehydratase (GMD, E.C. 4.2.1.47) and GDP-L-fucose synthase (wcaG, E.C. 1.1.1.271) catalyzed reactions from GDP-mannose to GDP-fucose is on the side of GDP-mannose (see FIGS. 11-A1 and 12-A1). In this experiment, first the enzymes were dispensed onto a vial up to the amounts mentioned in table 5. Buffer, co-factor, GDP-Man, NADPH were added in thus order, up to the mentioned concentration in table 5. The reaction was performed in 1.5 mL Eppendorf vials, at 37° C. and 550 rpm in the Eppendorf thermomixer comfort. Aliquots were taken at different time points and quenched by heating at 90° C. for 3 minutes and measured by ion exchange chromatography. It could be seen that the equilibrium is on the side of GDP-Man (see FIG. 12-A1).

To push the equilibrium of the reaction towards GDP-Fuc, coupling to another reaction (in a way that NADP$^+$ is constantly removed) needs to be engineered. In reaction A2 the enzymes Glk, PPK3 and glucose-6-phosphate-dehydrogensase (purchased from Merck-10165875001) (G6PDH, E.C: 1.1.1.49) were used to recycle NAPDH and increase the GDP-fucose yield. In this experiment, first the enzymes were dispensed into a vial up to the amounts mentioned in the table 6. After addition of enzymes, buffer, co-factor, GDP-Man, NADPH, glucose, ATP and polyphosphate were added in this order, up to the mentioned concentrations in table 6. The reaction was performed in a 1.5 mL Eppendorf vial, at 37° C. and 550 rpm in the Eppendorf thermomixer Comfort. Aliquots were taken at different time points and quenched by heating at 90° C. for 3 minutes and then measured by ion exchange chromatography. For the recycling the inexpensive substrates glucose and polyphosphate are used as substrates (see FIGS. 11-A2 and 12-A2).

Another experiment was performed for the production of GDP-Fuc from Man, ATP, GTP and polyphosphate, and L-glutamate for the regeneration of NADPH and shifting the equilibrium towards GDP-Fuc. In this experiment, first enzymes were dispensed into a vial up to the amounts mentioned in the table 7. After addition of enzymes, buffer, co-factor, Man, GTP, ATP and L-glutamate, and polyphosphate were added in this order, up to the mentioned concentrations in table 7. The reaction was performed in a 1.5 mL Eppendorf vial, at 37° C. and 550 rpm in the Eppendorf thermomixer Comfort. Aliquots were taken at different time points and quenched by heating at 90° C. for 3 minutes and then measured by ion exchange chromatography. In reaction A3 (see reaction conditions of reaction A3 in Table 7) glutamate dehydrogenase (purchased from Merck—10197734001) (GLDH, E.C. 1.4.1.4) was used to recycle NADPH from L-glutamate and water. (see FIGS. 11-A3 and 12-A3).

TABLE 5

Reactions conditions of examples A1.

| Enzymes | Concentration |
|---|---|
| WCAG | 1.03 µg/µL |
| GMD | 1.75 µg/µL |
| Substrates | |
| GDP-Man | 2 mM |
| NADPH | 2 mM |
| Buffer and co-factor | |
| Tris-HCl (pH = 8) | 100 mM |
| MgCl$_2$ | 10 mM |
| Volume | 40 µL |

TABLE 6

Reaction conditions for reaction A2.

| Enzymes | Concentration |
|---|---|
| WCAG | 0.8 µg/µL |
| GMD | 1.4 µg/µL |
| GLK | 0.129 µg/µL |
| PPK3 | 0.07 µg/µL |
| G6PDH | 0.28 µg/µL |
| Substrates | |
| GDP-Man | 4 mM |
| NADPH | 0.5 mM |
| Glucose | 10 mM |
| ATP | 1 mM |
| PolyP$_{25}$ | 2 mM |
| Buffer and co-factor | |
| Tris-HCl (pH = 8) | 100 mM |
| MgCl$_2$ | 10 mM |
| Volume | 50 µL |

TABLE 7

Reaction conditions of reaction A3.

| Enzymes | Concentration |
|---|---|
| WCAG | 0.3 µg/µL |
| GMD | 0.52 µg/µL |
| GLK | 0.09 µg/µL |
| PPK3 | 0.27 µg/µL |
| GLDH | 2.99 µg/µL |
| ManB/C | 0.046 µg/µL |
| PPA | 0.047 µg/µL |
| Substrates | |
| Man | 20 mM |
| GTP | 20 mM |
| ATP | 2 mM |
| PolyP$_{25}$ | 5 mM |
| L-glutamate | 50 mM |
| NADPH | 1 mM |
| Buffer and co-factor | |
| Tris-HCl (pH = 9) | 150 mM |
| MgCl$_2$ | 50 mM |
| Volume | 200 µL |

Example 7

Synthesis of GDP-Fucose from D-Mannose Using Glk

Figure 13:
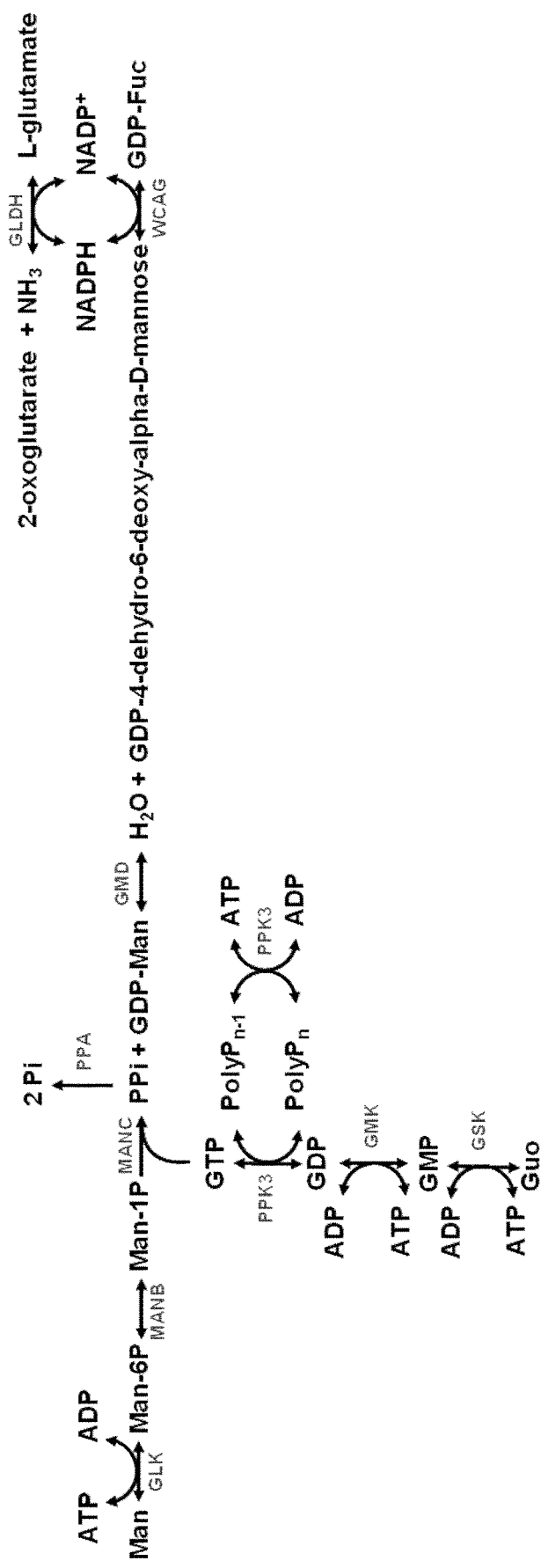
FIG. 13: shows the reaction cascade from the reaction cascade from mannose and guanosine to GDP-fucose as performed in Example 7.
Figure 14:
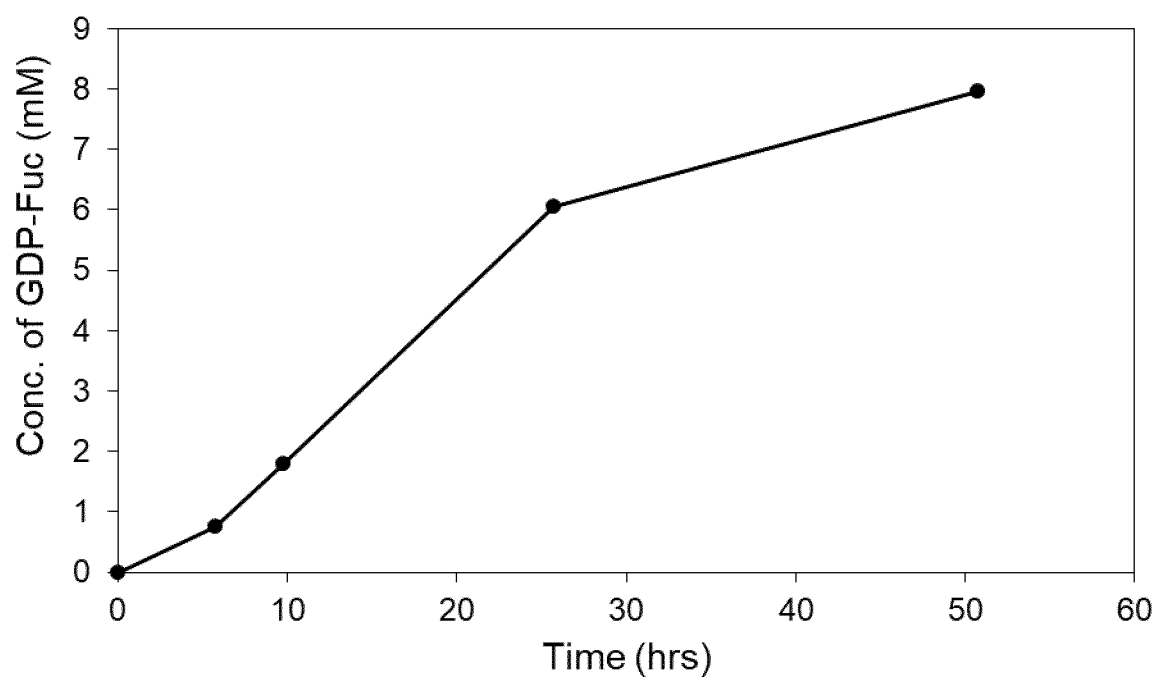
FIG. 14: shows reaction time course of the reaction in example 7 as measured by ion chromatography.

A one-pot enzymatic reaction was conducted to validate GDP-fucose synthesis from mannose through the cascade shown in FIG. 13. In this experiment, first enzymes were dispensed into a vial up to amounts mentioned in the table 8. After addition of enzymes, buffer, co-factor, mannose, ATP, L-glutamate, NADPH, guanosine (from a stock containing DMSO) and polyphosphate were added in this order, up to the mentioned concentrations in table 8. The reaction was performed in a 1.5 mL Eppendorf vial, at 37° C. and 550 rpm in a Eppendorf thermomixer Comfort. Aliquots were taken at different time points and quenched by heating at 90° C. for 3 minutes and then measured by ion exchange chromatography. Reaction time course of the reaction in example 7 is measured by ion chromatography as shown in FIG. 14.

TABLE 8

Reaction conditions as used in example 7.

| Enzymes | Concentrations |
| --- | --- |
| GSK | 0.128 µg/µL |
| GMK | 0.034 µg/µL |
| PPK3 | 0.2 µg/µL |
| GLK | 0.11 µg/µL |
| MANB/C | 0.071 µg/µL |
| WCAG | 0.24 µg/µL |
| GMD | 0.4 µg/µL |
| GLDH | 3.45 µg/µL |
| PPA | 0.04 µg/µL |
| Substrates | |
| Man | 11.5 mM |
| Guanosine (in DMSO) | 11.5 mM |
| ATP | 2.9 mM |
| PolyP$_{25}$ | 5.17 mM |
| L-glutamate | 86 mM |
| NADPH | 2.8 mM |
| Buffer and co-factor | |
| Tris-HCl (pH = 8) | 115 mM |
| MgCl$_2$ | 29 mM |
| Volume | 175 µL |

Example 8

Synthesis of GDP-Fucose from D-Mannose Using NahK

Figure 15:
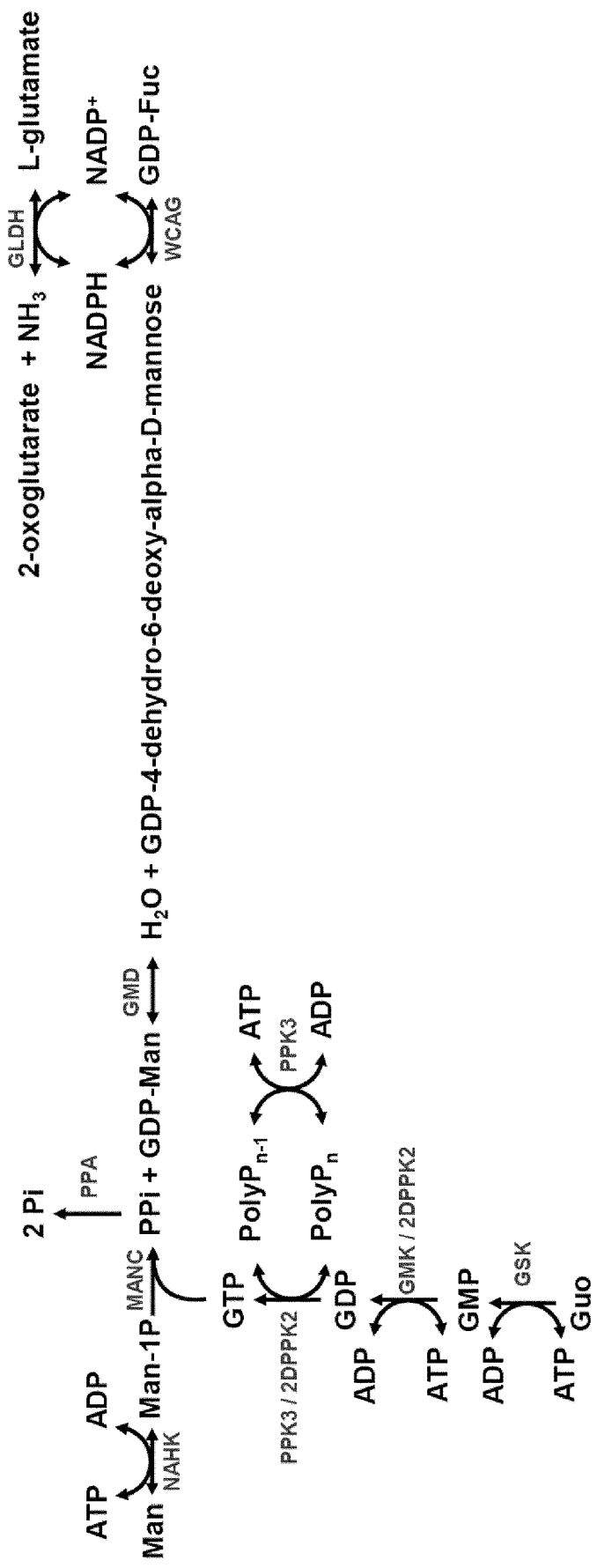
FIG. 15: shows the reaction cascade from mannose and guanosine to GDP-fucose as performed in Example 8.
Figure 16:
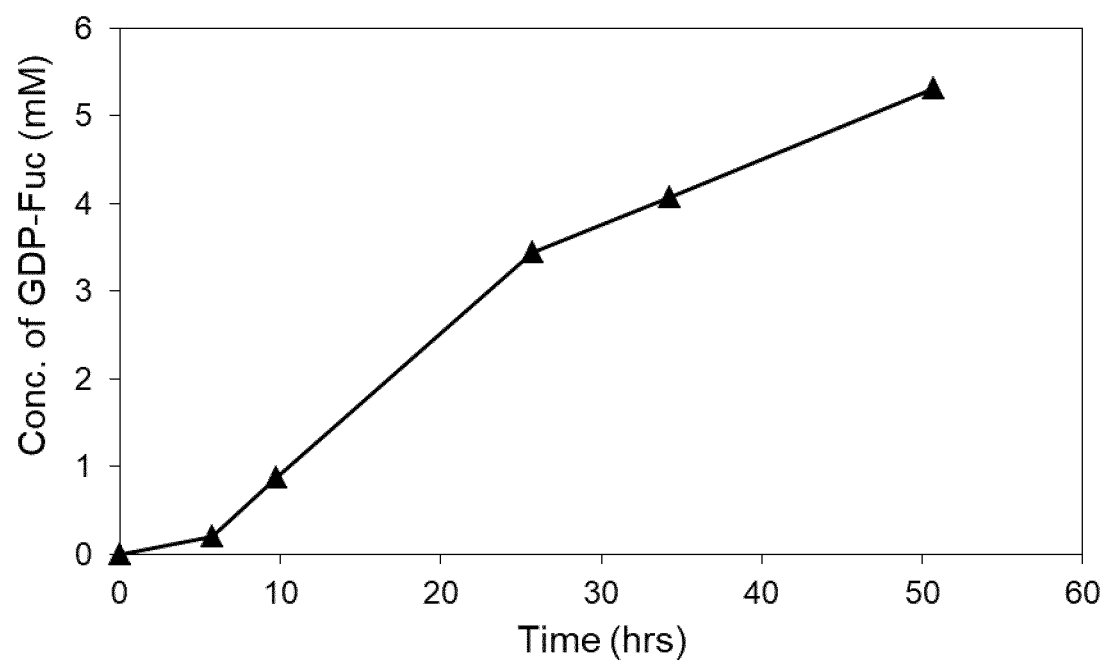
FIG. 16: shows reaction time course of the reaction in example 8 as measured by ion chromatography.

A one-pot enzymatic reaction was conducted to validate GDP-fucose synthesis from mannose through the cascade shown in FIG. 15. In this experiment, first enzymes were dispensed into a vial up to amounts mentioned in the table 9. After addition of enzymes, buffer, co-factor, mannose, ATP, L-glutamate, NADPH, guanosine (stock was prepared in DMSO) and polyphosphate were added in the order, up to the mentioned concentrations in table 9. The reaction was performed in 1.5 mL Eppendorf vials, at 37° C. and 550 rpm in a Eppendorf thermomixer comfort. Aliquots were taken at different time points and quenched by heating at 90° C. for 3 minutes and then measured by ion exchange chromatography. Reaction time course of the reaction in example 8 is measured by ion chromatography as shown in FIG. 16.

TABLE 9

Reaction conditions for example 8.

| Enzymes | Concentration |
| --- | --- |
| GSK | 0.12 µg/µL |
| GMK | 0.03 µg/µL |
| PPK3 | 0.19 µg/µL |
| NAHK | 0.14 µg/µL |
| MANB/C | 0.06 µg/µL |
| WCAG | 0.22 µg/µL |
| GMD | 0.38 µg/µL |
| GLDH | 3.26 µg/µL |
| PPA | 0.03 µg/µL |
| Substrates | |
| Man | 10.9 mM |
| Guanosine (in DMSO) | 10.9 mM |
| ATP | 2.75 mM |
| PolyP$_{25}$ | 4.9 mM |
| L-glutamate | 81 mM |
| NADPH | 2.6 mM |
| Buffer and co-factor | |
| Tris-HCl (pH = 8) | 108 mM |
| MgCl$_2$ | 27 mM |
| Volume | 185 µL |

Example 9

Synthesis of 3-Fucosyllactose

Figure 17:
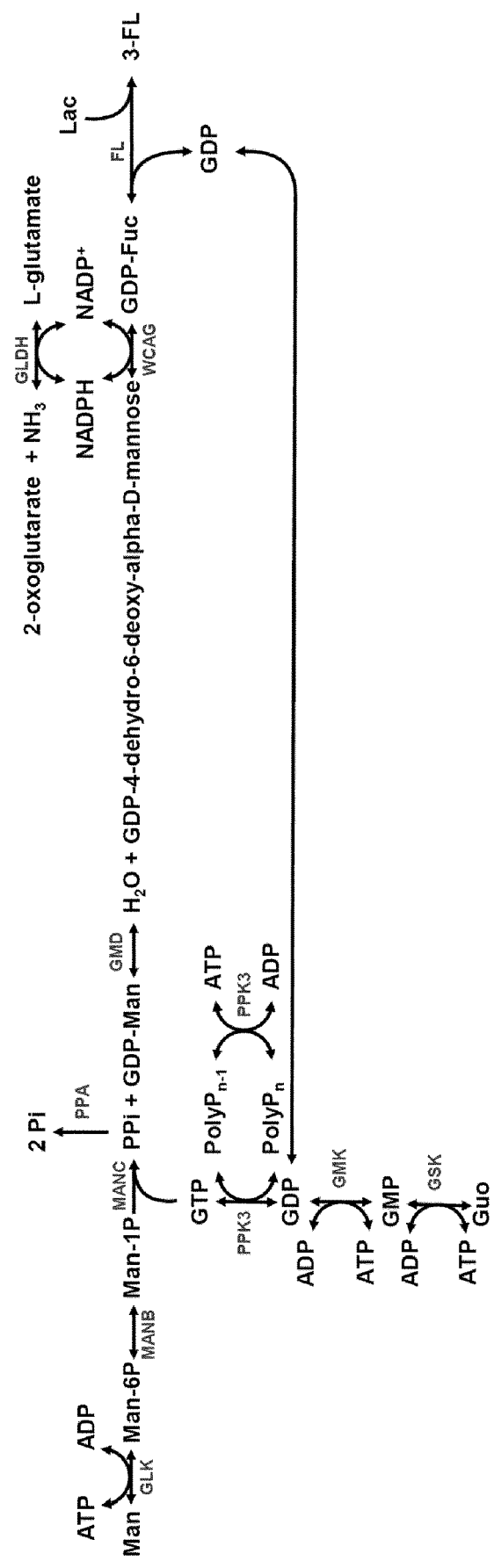
FIG. 17: shows the reaction cascade from mannose and guanosine to 3-fucosyl-lactose as performed in Example 9.
Figure 18:
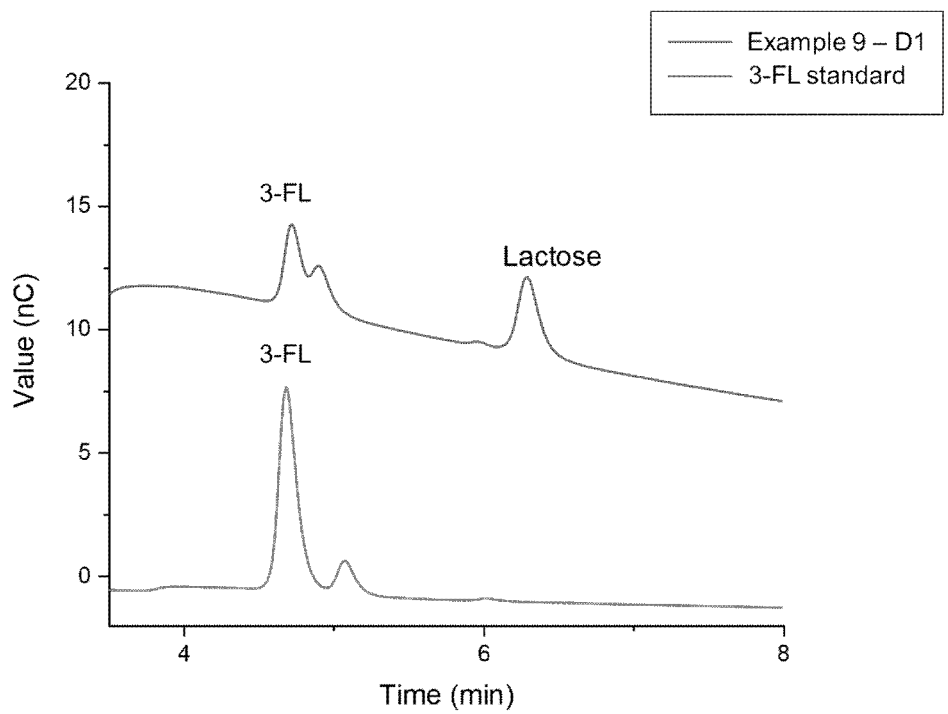
FIG. 18: shows synthesis of 3-fucosyllactose from mannose and guanosine. Reaction chromatogram of a reaction aliquot taken after a reaction time of 48 hours (black) and of 3-fucosyllactose standard samples. The peaks were detected by amperometric detection.
Figure 19:
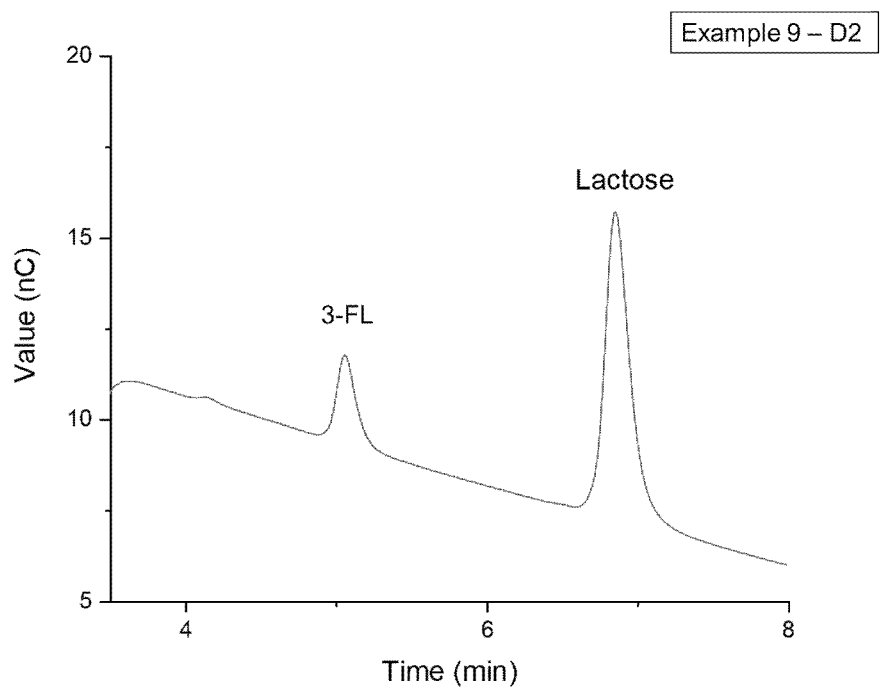
FIG. 19: shows synthesis of 3-fucosyllactose from guanosine and fucose (reaction D2 of example 9). Chromatogram of a reaction aliquot taken after a reaction time of 48 hours. The peaks were detected by amperometric detection.

The cascades for GDP-fucose production can be coupled to fucosyltransferases to fucosylate molecules or biomolecules, e.g. human milk oligosaccharides and therapeutic proteins. The coupling is performed in one-pot reactions (see FIG. 17). Reactions were conducted where the GDP-fucose cascade was coupled to 3/4-fucosyltransferase to produce 3-fucosyllactose starting from D-mannose (reaction D1; see FIG. 18). In this experiment, first enzymes were dispensed into a vial up to amounts mentioned in the table 10. After addition of enzymes, buffer, co-factor, mannose, ATP, L-glutamate, NADPH, lactose, guanosine (stock was prepared in DMSO) and polyphosphate were added in this order, up to the mentioned concentrations in table 10. The reaction was performed in 1.5 mL Eppendorf vials, at 37° C. and 550 rpm in a Eppendorf thermomixer comfort. Aliquot was taken and quenched by heating at 90° C. for 3 minutes and then measured by ion exchange chromatography. Another experiment was performed to produce 3-fucosyllactose in which GDP-Fuc was produced from guanosine, L-fucose (reaction D2; see FIG. 19). In this experiment, first enzymes added up to amounts mentioned in the table 11. After addition of enzymes, buffer, co-factor, L-fucose, ATP, lactose, guanosine (stock was prepared in DMSO) and polyphosphate were added in the order, up to the mentioned concentration in table 11. The reaction was performed in 1.5 mL Eppendorf vials, at 37° C. and 550 rpm in a Eppendorf thermomixer comfort. Aliquot was taken and quenched by heating at 90° C. for 3 minutes and then measured by ion exchange chromatography.

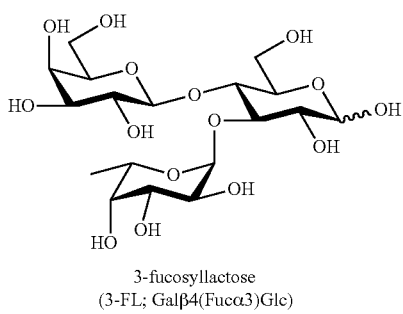

3-fucosyllactose
(3-FL; Galβ4(Fucα3)Glc)

TABLE 10

Reaction conditions for reaction D1.

| Enzymes | Concentration |
| --- | --- |
| GSK | 0.128 μg/μL |
| GMK | 0.034 μg/μL |
| PPK3 | 0.2 μg/μL |
| GLK | 0.11 μg/μL |
| MANB/C | 0.071 μg/μL |
| WCAG | 0.24 μg/μL |
| GMD | 0.4 μg/μL |
| GLDH | 3.45 μg/μL |
| PPA | 0.04 μg/μL |
| 3/4FT | 0.07 μg/μL |
| Substrates | |
| Man | 8.7 mM |
| Guanosine (in DMSO) | 2.9 mM |
| ATP | 2.9 mM |
| PolyP$_{25}$ | 5.2 mM |
| L-glutamate | 29 mM |
| NADPH | 1.45 mM |
| Lactose | 11.6 mM |
| Buffer and co-factor | |
| Tris-HCl (pH = 8) | 116 mM |
| MgCl$_2$ | 43 mM |
| Volume | 172 μL |

TABLE 11

Reaction conditions for reaction D2.

| Enzymes | Concentration |
| --- | --- |
| GSK | 0.16 μg/μL |
| GMK | 0.042 μg/μL |
| PPK3 | 0.25 μg/μL |
| FKP | 0.42 μg/μL |
| PPA | 0.05 μg/μL |
| 3/4FT | 0.07 μg/μL |
| Substrates | |
| Fucose | 14.1 mM |
| Guanosine (in DMSO) | 3.5 mM |
| ATP | 3.6 mM |
| PolyP$_{25}$ | 6.3 mM |
| Lactose | 14.1 mM |
| Buffer and co-factor | |
| Tris-HCl (pH = 8) | 141 mM |
| MgCl$_2$ | 35 mM |
| Volume | 141 μL |

Example 10

Production of L-Fucose from D-Mannose

Figure 20:
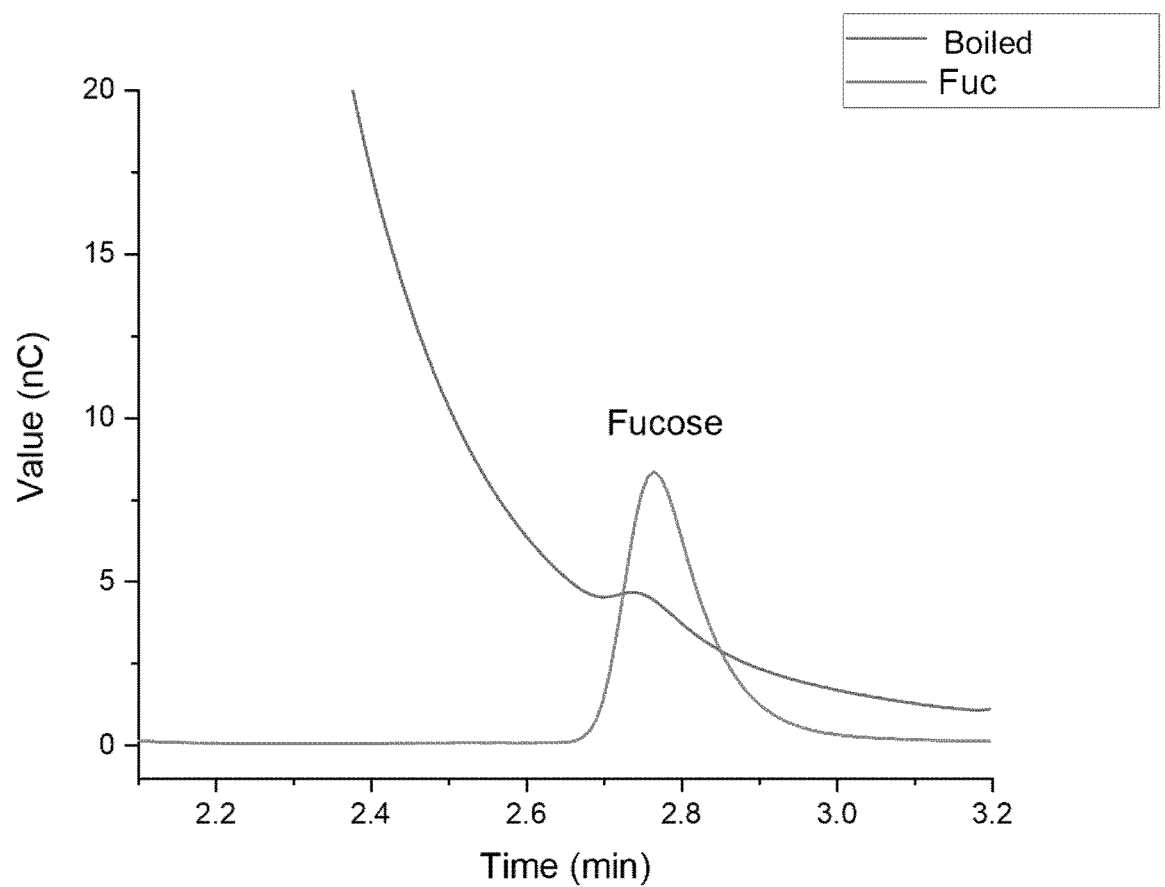
FIG. 20: shows the production of L-fucose from D-mannose. The reaction of sample in example 8 was heated for 1 hour at 95° C. (see, example 10). An aliquot of the heated sample was taken and measured by ion chromatography with amperometric detection (black) and compared against a fucose standard (Fuc).

The cascade described in examples 7 and 8 can be used to produce L-fucose from D-mannose and guanosine. The reaction in example 8 was heated at 95° C. for 1 hour. An aliquot taken after heating was measured by ion chromatography (see FIG. 20).

A sequence listing is attached to this application comprising the sequences of the following table:

| SEQ ID | description |
| --- | --- |
| 1 | Glucokinase |
| 2 | Phosphomannomutase |
| 3 | N-acetylhexosamine-1-kinase |
| 4 | Mannose-1-phosphate guanylyltransferase |
| 5 | GDP-mannose 4,6-dehydratase |
| 6 | GDP-L-fucose synthase |
| 7 | L-fucokinase |
| 8 | Guanosine kinase |
| 9 | 2-domain polyphosphate kinase 2 |
| 10 | inorganic pyrophosphatase |
| 11 | Guanylate kinase |
| 12 | Glutamate dehydrogenase 1 (GLDH) |
| 13 | Glucose-6-phosphate 1-dehydrogenase (G6PDH) |
| 14 | phosphotransferase 3 (PPK3) |
| 15 | Glucose/galactose 1-dehydrogenase (GDH) |
| 16 | alpha-1,3/4-fucosyltransferase (3/4FT) |

The invention claimed is:

1. A method for producing guanosine 5'-diphospho-β-L-fucose from guanosine and L-fucose comprising the following steps:

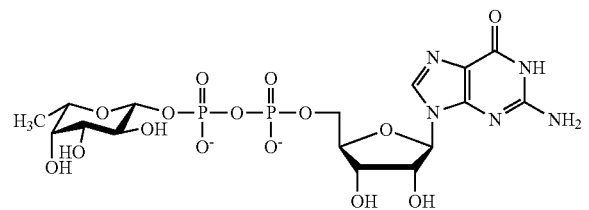

A) providing a solution comprising
   (i) guanosine and L-fucose represented by the following formulae

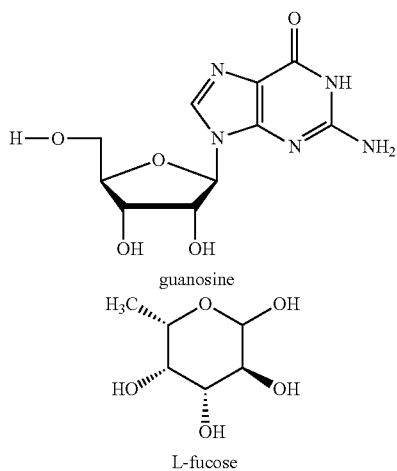

guanosine

L-fucose (ii) polyphosphate, adenosine triphosphate and a co-solvent for solubilizing guanosine; and
   providing a set of enzymes comprising a guanosine kinase of the EC class 2.7.1.73, a polyphosphate kinase of the EC class 2.7.4.1, and a L-fucokinase/L-fucose-1-phosphate guanylyltransferase of the EC class selected from the group consisting of 2.7.1.52 and 2.7.7.30;

B) producing guanosine 5'-diphospho-β-L-fucose from guanosine and L-fucose in the presence of the set of enzymes, polyphosphate, adenosine triphosphate and the co-solvent.

2. The method according to claim 1, wherein the guanosine kinase comprises an amino acid sequence having at least 85% sequence identity to SEQ ID NO:8.

3. The method according to claim 1, wherein the polyphosphate kinase comprises an amino acid sequence having at least 85% sequence identity to SEQ ID NO: 9 or SEQ ID NO. 14.

4. The method according to claim 1, wherein the set of enzymes further comprises a pyrophosphatase.

5. The method according to claim 1, wherein the set of enzymes is co-immobilized on a solid support.

6. The method according to claim 5, wherein the at least one enzyme is immobilized on a solid support from cell lysate or the set of enzymes is co-immobilized on a solid support from cell lysate.

7. The method according to claim 1, wherein the concentration of guanosine and L-fucose or guanosine and D-mannose in the solution provided in step A) is in the range of 0.2 mM to 5,000 mM.

8. The method according to claim 1, wherein the guanosine 5'-diphospho-β-L-fucose is produced in a single reaction mixture.

9. The method according to claim 1, wherein the amount of co-solvent is from 0.01 vol % to 30 vol % based on total volume of the solution provided in step A).

10. The method according to claim 1, wherein the co-solvent is dimethyl sulfoxide.

11. The method according to claim 1, wherein the method further comprises the step
   producing L-fucose from guanosine 5'-diphospho-β-L-fucose in the presence of a fucosyltransferase and in the absence of an acceptor; or
   producing L-fucose by heating the guanosine 5'-diphospho-β-L-fucose at the temperature in a range of 80 to 100° C.

12. The method according to claim 1, further comprising the step of
   C) isolating the guanosine 5'-diphospho-β-L-fucose.

13. The method according to claim 1, wherein the L-fucokinase comprises an amino acid sequence having at least 85% sequence identity to SEQ ID NO: 7, and the L-fucose-1-phosphate guanylyltransferase comprises an amino acid sequence having at least 85% sequence identity to SEQ ID NO: 16.

14. The method according to claim 1, wherein the guanosine kinase comprises an amino acid sequence having at least 95% sequence identity to SEQ ID NO: 8; the polyphosphate kinase comprises an amino acid sequence having at least 95% sequence identity to SEQ ID NO: 9 or SEQ ID NO. 14; the L-fucokinase comprises an amino acid sequence having at least 95% sequence identity to SEQ ID NO: 7, and the L-fucose-1-phosphate guanylyltransferase comprises an amino acid sequence having at least 95% sequence identity to SEQ ID NO:16.

15. The method according to claim 14, wherein the guanosine kinase comprises the amino acid sequence of SEQ ID NO: 8; the polyphosphate kinase comprises the amino acid sequence of SEQ ID NO: 9 or SEQ ID NO. 14; the L-fucokinase comprises the amino acid sequence of SEQ ID NO: 7, and the L-fucose-1-phosphate guanylyltransferase comprises the amino acid sequence of SEQ ID NO:16.

* * * * *

SEQUENCE LISTING

<160> NUMBER OF SEQ ID NOS: 16

<210> SEQ ID NO 1
<211> LENGTH: 321
<212> TYPE: PRT
<213> ORGANISM: Escherichia coli
<220> FEATURE:
<221> NAME/KEY: PEPTIDE
<222> LOCATION: (1)..(321)
<223> OTHER INFORMATION: Glucokinase

<400> SEQUENCE: 1

Met Thr Lys Tyr Ala Leu Val Gly Asp Val Gly Gly Thr Asn Ala Arg
1               5                   10                  15

```
Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
    50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
    130                 135                 140

Val His Val Asp Lys Arg Trp Val Ser Leu Pro Gly Glu Gly Gly His
145                 150                 155                 160

Val Asp Phe Ala Pro Asn Ser Glu Glu Glu Ala Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
    210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
            260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
    290                 295                 300

Gly Leu Leu Gly Ser Gly Ala His Leu Arg Gln Thr Leu Gly His Ile
305                 310                 315                 320

Leu

<210> SEQ ID NO 2
<211> LENGTH: 456
<212> TYPE: PRT
<213> ORGANISM: Escherichia coli
<220> FEATURE:
<221> NAME/KEY: PEPTIDE
<222> LOCATION: (1)..(456)
<223> OTHER INFORMATION: Phosphomannomutase

<400> SEQUENCE: 2

Met Lys Lys Leu Thr Cys Phe Lys Ala Tyr Asp Ile Arg Gly Lys Leu
1               5                   10                  15

Gly Glu Glu Leu Asn Glu Asp Ile Ala Trp Arg Ile Gly Arg Ala Tyr
            20                  25                  30

Gly Glu Phe Leu Lys Pro Lys Thr Ile Val Leu Gly Gly Asp Val Arg
```

```
                35                  40                  45
Leu Thr Ser Glu Thr Leu Lys Leu Ala Leu Ala Lys Gly Leu Gln Asp
 50                  55                  60

Ala Gly Val Asp Val Leu Asp Ile Gly Met Ser Gly Thr Glu Glu Ile
 65                  70                  75                  80

Tyr Phe Ala Thr Phe His Leu Gly Val Asp Gly Gly Ile Glu Val Thr
                 85                  90                  95

Ala Ser His Asn Pro Met Asp Tyr Asn Gly Met Lys Leu Val Arg Glu
                100                 105                 110

Gly Ala Arg Pro Ile Ser Gly Asp Thr Gly Leu Arg Asp Val Gln Arg
                115                 120                 125

Leu Ala Glu Ala Asn Asp Phe Pro Pro Val Asp Glu Thr Lys Arg Gly
130                 135                 140

Arg Tyr Gln Gln Ile Asn Leu Arg Asp Ala Tyr Val Asp His Leu Phe
145                 150                 155                 160

Gly Tyr Ile Asn Val Lys Asn Leu Thr Pro Leu Lys Leu Val Ile Asn
                165                 170                 175

Ser Gly Asn Gly Ala Ala Gly Pro Val Val Asp Ala Ile Glu Ala Arg
                180                 185                 190

Phe Lys Ala Leu Gly Ala Pro Val Glu Leu Ile Lys Val His Asn Thr
                195                 200                 205

Pro Asp Gly Asn Phe Pro Asn Gly Ile Pro Asn Pro Leu Leu Pro Glu
210                 215                 220

Cys Arg Asp Asp Thr Arg Asn Ala Val Ile Lys His Gly Ala Asp Met
225                 230                 235                 240

Gly Ile Ala Phe Asp Gly Asp Phe Asp Arg Cys Phe Leu Phe Asp Glu
                245                 250                 255

Lys Gly Gln Phe Ile Glu Gly Tyr Tyr Ile Val Gly Leu Leu Ala Glu
                260                 265                 270

Ala Phe Leu Glu Lys Asn Pro Gly Ala Lys Ile Ile His Asp Pro Arg
                275                 280                 285

Leu Ser Trp Asn Thr Val Asp Val Val Thr Ala Ala Gly Gly Thr Pro
290                 295                 300

Val Met Ser Lys Thr Gly His Ala Phe Ile Lys Glu Arg Met Arg Lys
305                 310                 315                 320

Glu Asp Ala Ile Tyr Gly Gly Glu Met Ser Ala His His Tyr Phe Arg
                325                 330                 335

Asp Phe Ala Tyr Cys Asp Ser Gly Met Ile Pro Trp Leu Leu Val Ala
                340                 345                 350

Glu Leu Val Cys Leu Lys Asp Lys Thr Leu Gly Glu Leu Val Arg Asp
                355                 360                 365

Arg Met Ala Ala Phe Pro Ala Ser Gly Glu Ile Asn Ser Lys Leu Ala
                370                 375                 380

Gln Pro Val Glu Ala Ile Asn Arg Val Glu Gln His Phe Ser Arg Glu
385                 390                 395                 400

Ala Leu Ala Val Asp Arg Thr Asp Gly Ile Ser Met Thr Phe Ala Asp
                405                 410                 415

Trp Arg Phe Asn Leu Arg Thr Ser Asn Thr Glu Pro Val Val Arg Leu
                420                 425                 430

Asn Val Glu Ser Arg Gly Asp Val Pro Leu Met Glu Ala Arg Thr Arg
                435                 440                 445

Thr Leu Leu Thr Leu Leu Asn Glu
                450                 455
```

<210> SEQ ID NO 3
<211> LENGTH: 359
<212> TYPE: PRT
<213> ORGANISM: Bifidobacterium longum
<220> FEATURE:
<221> NAME/KEY: PEPTIDE
<222> LOCATION: (1)..(359)
<223> OTHER INFORMATION: N-acetylhexosamine-1-kinase

<400> SEQUENCE: 3

```
Met Thr Glu Ser Asn Glu Asp Leu Phe Gly Ile Ala Ser His Phe Ala
1               5                   10                  15

Leu Glu Gly Ala Val Thr Gly Ile Glu Pro Tyr Gly Asp Gly His Ile
            20                  25                  30

Asn Thr Thr Tyr Leu Val Thr Thr Asp Gly Pro Arg Tyr Ile Leu Gln
        35                  40                  45

Gln Met Asn Thr Ser Ile Phe Pro Asp Thr Val Asn Leu Met Arg Asn
    50                  55                  60

Val Glu Leu Val Thr Ser Thr Leu Lys Ala Gln Gly Lys Glu Thr Leu
65                  70                  75                  80

Asp Ile Val Pro Thr Thr Ser Gly Ala Thr Trp Ala Glu Ile Asp Gly
                85                  90                  95

Gly Ala Trp Arg Val Tyr Lys Phe Ile Glu His Thr Val Ser Tyr Asn
            100                 105                 110

Leu Val Pro Asn Pro Asp Val Phe Arg Glu Ala Gly Ser Ala Phe Gly
        115                 120                 125

Asp Phe Gln Asn Phe Leu Ser Glu Phe Asp Ala Ser Gln Leu Thr Glu
    130                 135                 140

Thr Ile Ala His Phe His Asp Thr Pro His Arg Phe Glu Asp Phe Lys
145                 150                 155                 160

Ala Ala Leu Ala Ala Asp Lys Leu Gly Arg Ala Ala Ala Cys Gln Pro
                165                 170                 175

Glu Ile Asp Phe Tyr Leu Ser His Ala Asp Gln Tyr Ala Val Val Met
            180                 185                 190

Asp Gly Leu Arg Asp Gly Ser Ile Pro Leu Arg Val Thr His Asn Asp
        195                 200                 205

Thr Lys Leu Asn Asn Ile Leu Met Asp Ala Thr Thr Gly Lys Ala Arg
    210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
                245                 250                 255

Lys Asp Leu Ser Lys Val His Phe Ser Thr Glu Leu Phe Arg Ala Tyr
            260                 265                 270

Thr Glu Gly Phe Val Gly Glu Leu Arg Gly Ser Ile Thr Ala Arg Glu
        275                 280                 285

Ala Glu Leu Leu Pro Phe Ser Gly Asn Leu Leu Thr Met Glu Cys Gly
    290                 295                 300

Met Arg Phe Leu Ala Asp Tyr Leu Glu Gly Asp Ile Tyr Phe Ala Thr
305                 310                 315                 320

Lys Tyr Pro Glu His Asn Leu Val Arg Thr Arg Thr Gln Ile Lys Leu
                325                 330                 335

Val Gln Glu Met Glu Gln Lys Ala Ser Glu Thr Arg Ala Ile Val Ala
            340                 345                 350
```

Asp Ile Met Glu Ala Ala Arg
        355

<210> SEQ ID NO 4
<211> LENGTH: 478
<212> TYPE: PRT
<213> ORGANISM: Escherichia coli
<220> FEATURE:
<221> NAME/KEY: PEPTIDE
<222> LOCATION: (1)..(478)
<223> OTHER INFORMATION: Mannose-1-phosphate guanylyltransferase

<400> SEQUENCE: 4

Met Ala Gln Ser Lys Leu Tyr Pro Val Met Ala Gly Gly Ser Gly
1               5                   10                  15

Ser Arg Leu Trp Pro Leu Ser Arg Val Leu Tyr Pro Lys Gln Phe Leu
            20                  25                  30

Cys Leu Lys Gly Asp Leu Thr Met Leu Gln Thr Thr Ile Cys Arg Leu
        35                  40                  45

Asn Gly Val Glu Cys Glu Ser Pro Val Val Ile Cys Asn Glu Gln His
    50                  55                  60

Arg Phe Ile Val Ala Glu Gln Leu Arg Gln Leu Asn Lys Leu Thr Glu
65                  70                  75                  80

Asn Ile Ile Leu Glu Pro Ala Gly Arg Asn Thr Ala Pro Ala Ile Ala
                85                  90                  95

Leu Ala Ala Leu Ala Ala Lys Arg His Ser Pro Glu Ser Asp Pro Leu
            100                 105                 110

Met Leu Val Leu Ala Ala Asp His Val Ile Ala Asp Glu Asp Ala Phe
        115                 120                 125

Arg Ala Ala Val Arg Asn Ala Met Pro Tyr Ala Glu Ala Gly Lys Leu
    130                 135                 140

Val Thr Phe Gly Ile Val Pro Asp Leu Pro Glu Thr Gly Tyr Gly Tyr
145                 150                 155                 160

Ile Arg Arg Gly Glu Val Ser Ala Gly Glu Gln Asp Met Val Ala Phe
                165                 170                 175

Glu Val Ala Gln Phe Val Glu Lys Pro Asn Leu Glu Thr Ala Gln Ala
            180                 185                 190

Tyr Val Ala Ser Gly Glu Tyr Tyr Trp Asn Ser Gly Met Phe Leu Phe
        195                 200                 205

Arg Ala Gly Arg Tyr Leu Glu Glu Leu Lys Lys Tyr Arg Pro Asp Ile
    210                 215                 220

Leu Asp Ala Cys Glu Lys Ala Met Ser Ala Val Asp Pro Asp Leu Asn
225                 230                 235                 240

Phe Ile Arg Val Asp Glu Glu Ala Phe Leu Ala Cys Pro Glu Glu Ser
                245                 250                 255

Val Asp Tyr Ala Val Met Glu Arg Thr Ala Asp Ala Val Val Val Pro
            260                 265                 270

Met Asp Ala Gly Trp Ser Asp Val Gly Ser Trp Ser Ser Leu Trp Glu
        275                 280                 285

Ile Ser Ala His Thr Ala Glu Gly Asn Val Cys His Gly Asp Val Ile
    290                 295                 300

Asn His Lys Thr Glu Asn Ser Tyr Val Tyr Ala Glu Ser Gly Leu Val
305                 310                 315                 320

Thr Thr Val Gly Val Lys Asp Leu Val Val Gln Thr Lys Asp Ala
                325                 330                 335

Val Leu Ile Ala Asp Arg Asn Ala Val Gln Asp Val Lys Lys Val Val

```
                    340                 345                 350
Glu Gln Ile Lys Ala Asp Gly Arg His Glu His Arg Val His Arg Glu
            355                 360                 365

Val Tyr Arg Pro Trp Gly Lys Tyr Asp Ser Ile Asp Ala Gly Asp Arg
370                 375                 380

Tyr Gln Val Lys Arg Ile Thr Val Lys Pro Gly Glu Gly Leu Ser Val
385                 390                 395                 400

Gln Met His His His Arg Ala Glu His Trp Val Val Ala Gly Thr
            405                 410                 415

Ala Lys Val Thr Ile Asp Gly Asp Ile Lys Leu Leu Gly Glu Asn Glu
            420                 425                 430

Ser Ile Tyr Ile Pro Leu Gly Ala Thr His Cys Leu Glu Asn Pro Gly
            435                 440                 445

Lys Ile Pro Leu Asp Leu Ile Glu Val Arg Ser Gly Ser Tyr Leu Glu
            450                 455                 460

Glu Asp Asp Val Val Arg Phe Ala Asp Arg Tyr Gly Arg Val
465                 470                 475

<210> SEQ ID NO 5
<211> LENGTH: 373
<212> TYPE: PRT
<213> ORGANISM: Escherichia coli
<220> FEATURE:
<221> NAME/KEY: PEPTIDE
<222> LOCATION: (1)..(373)
<223> OTHER INFORMATION: GDP-mannose 4,6-dehydratase

<400> SEQUENCE: 5

Met Ser Lys Val Ala Leu Ile Thr Gly Val Thr Gly Gln Asp Gly Ser
1               5                   10                  15

Tyr Leu Ala Glu Phe Leu Leu Glu Lys Gly Tyr Glu Val His Gly Ile
                20                  25                  30

Lys Arg Arg Ala Ser Ser Phe Asn Thr Glu Arg Val Asp His Ile Tyr
            35                  40                  45

Gln Asp Pro His Thr Cys Asn Pro Lys Phe His Leu His Tyr Gly Asp
        50                  55                  60

Leu Ser Asp Thr Ser Asn Leu Thr Arg Ile Leu Arg Glu Val Gln Pro
65                  70                  75                  80

Asp Glu Val Tyr Asn Leu Gly Ala Met Ser His Val Ala Val Ser Phe
                85                  90                  95

Glu Ser Pro Glu Tyr Thr Ala Asp Val Asp Ala Met Gly Thr Leu Arg
            100                 105                 110

Leu Leu Glu Ala Ile Arg Phe Leu Gly Leu Glu Lys Lys Thr Arg Phe
        115                 120                 125

Tyr Gln Ala Ser Thr Ser Glu Leu Tyr Gly Leu Val Gln Glu Ile Pro
    130                 135                 140

Gln Lys Glu Thr Thr Pro Phe Tyr Pro Arg Ser Pro Tyr Ala Val Ala
145                 150                 155                 160

Lys Leu Tyr Ala Tyr Trp Ile Thr Val Asn Tyr Arg Glu Ser Tyr Gly
                165                 170                 175

Met Tyr Ala Cys Asn Gly Ile Leu Phe Asn His Glu Ser Pro Arg Arg
            180                 185                 190

Gly Glu Thr Phe Val Thr Arg Lys Ile Thr Arg Ala Ile Ala Asn Ile
        195                 200                 205

Ala Gln Gly Leu Glu Ser Cys Leu Tyr Leu Gly Asn Met Asp Ser Leu
    210                 215                 220
```

```
Arg Asp Trp Gly His Ala Lys Asp Tyr Val Lys Met Gln Trp Met Met
225                 230                 235                 240

Leu Gln Gln Glu Gln Pro Glu Asp Phe Val Ile Ala Thr Gly Val Gln
            245                 250                 255

Tyr Ser Val Arg Gln Phe Val Glu Met Ala Ala Ala Gln Leu Gly Ile
        260                 265                 270

Lys Leu Arg Phe Glu Gly Thr Gly Val Glu Lys Gly Ile Val Val
            275                 280                 285

Ser Val Thr Gly His Asp Ala Pro Gly Val Lys Pro Gly Asp Val Ile
        290                 295                 300

Ile Ala Val Asp Pro Arg Tyr Phe Arg Pro Ala Glu Val Glu Thr Leu
305                 310                 315                 320

Leu Gly Asp Pro Thr Lys Ala His Glu Lys Leu Gly Trp Lys Pro Glu
            325                 330                 335

Ile Thr Leu Arg Glu Met Val Ser Glu Met Val Ala Asn Asp Leu Glu
            340                 345                 350

Ala Ala Lys Lys His Ser Leu Leu Lys Ser His Gly Tyr Asp Val Ala
            355                 360                 365

Ile Ala Leu Glu Ser
            370

<210> SEQ ID NO 6
<211> LENGTH: 321
<212> TYPE: PRT
<213> ORGANISM: Escherichia coli
<220> FEATURE:
<221> NAME/KEY: PEPTIDE
<222> LOCATION: (1)..(321)
<223> OTHER INFORMATION: GDP-L-fucose synthase

<400> SEQUENCE: 6

Met Ser Lys Gln Arg Val Phe Ile Ala Gly His Arg Gly Met Val Gly
1               5                   10                  15

Ser Ala Ile Lys Arg Gln Leu Glu Gln Arg Gly Asp Val Glu Leu Val
            20                  25                  30

Leu Arg Thr Arg Asp Glu Leu Asn Leu Leu Asp Ser Arg Ala Val His
        35                  40                  45

Asp Phe Phe Ala Ser Glu Ser Ile Asp Gln Val Tyr Leu Ala Ala Ala
    50                  55                  60

Lys Val Gly Gly Ile Val Ala Asn Asn Thr Tyr Pro Ala Asp Phe Ile
65                  70                  75                  80

Tyr Gln Asn Met Met Ile Glu Ser Asn Ile Ile His Ala Ala His Gln
                85                  90                  95

Asn Asp Val Asn Lys Leu Leu Phe Leu Gly Ser Ser Cys Ile Tyr Pro
            100                 105                 110

Lys Leu Ala Lys Gln Pro Met Ala Glu Ser Glu Leu Leu Gln Gly Thr
        115                 120                 125

Leu Glu Pro Thr Asn Glu Pro Tyr Ala Ile Ala Lys Ile Ala Gly Ile
    130                 135                 140

Lys Leu Cys Glu Ser Tyr Asn Arg Gln Tyr Gly Arg Asp Tyr Arg Ser
145                 150                 155                 160

Val Met Pro Thr Asn Leu Tyr Gly Pro His Asp Asn Phe His Pro Ser
                165                 170                 175

Asn Ser His Val Ile Pro Ala Leu Leu Arg Arg Phe His Glu Ala Thr
            180                 185                 190
```

```
Ala Gln Asn Ala Pro Asp Val Val Trp Gly Ser Gly Thr Pro Met
        195                 200                 205

Arg Glu Phe Leu His Val Asp Asp Met Ala Ala Ser Ile His Val
        210                 215                 220

Met Glu Leu Ala His Glu Val Trp Leu Glu Asn Thr Gln Pro Met Leu
225                 230                 235                 240

Ser His Ile Asn Val Gly Thr Gly Val Asp Cys Thr Ile Arg Glu Leu
                245                 250                 255

Ala Gln Thr Ile Ala Lys Val Val Asp Tyr Lys Gly Arg Val Phe
            260                 265                 270

Asp Ala Ser Lys Pro Asp Gly Thr Pro Arg Lys Leu Leu Asp Val Thr
        275                 280                 285

Arg Leu His Gln Leu Gly Trp Tyr His Glu Ile Ser Leu Glu Ala Gly
        290                 295                 300

Leu Ala Ser Thr Tyr Gln Trp Phe Leu Glu Asn Arg Asp Arg Phe Arg
305                 310                 315                 320

Gly

<210> SEQ ID NO 7
<211> LENGTH: 949
<212> TYPE: PRT
<213> ORGANISM: Bacteroides fragilis
<220> FEATURE:
<221> NAME/KEY: PEPTIDE
<222> LOCATION: (1)..(949)
<223> OTHER INFORMATION: L-fucokinase

<400> SEQUENCE: 7

Met Gln Lys Leu Leu Ser Leu Pro Ser Asn Leu Val Gln Ser Phe His
1               5                   10                  15

Glu Leu Glu Arg Val Asn Arg Thr Asp Trp Phe Cys Thr Ser Asp Pro
            20                  25                  30

Val Gly Lys Lys Leu Gly Ser Gly Gly Thr Ser Trp Leu Leu Glu
        35                  40                  45

Glu Cys Tyr Asn Glu Tyr Ser Asp Gly Ala Thr Phe Gly Glu Trp Leu
50                  55                  60

Glu Lys Glu Lys Arg Ile Leu Leu His Ala Gly Gly Gln Ser Arg Arg
65                  70                  75                  80

Leu Pro Gly Tyr Ala Pro Ser Gly Lys Ile Leu Thr Pro Val Pro Val
                85                  90                  95

Phe Arg Trp Glu Arg Gly Gln His Leu Gly Gln Asn Leu Leu Ser Leu
            100                 105                 110

Gln Leu Pro Leu Tyr Glu Lys Ile Met Ser Leu Ala Pro Asp Lys Leu
        115                 120                 125

His Thr Leu Ile Ala Ser Gly Asp Val Tyr Ile Arg Ser Glu Lys Pro
        130                 135                 140

Leu Gln Ser Ile Pro Glu Ala Asp Val Val Cys Tyr Gly Leu Trp Val
145                 150                 155                 160

Asp Pro Ser Leu Ala Thr His His Gly Val Phe Ala Ser Asp Arg Lys
                165                 170                 175

His Pro Glu Gln Leu Asp Phe Met Leu Gln Lys Pro Ser Leu Ala Glu
            180                 185                 190

Leu Glu Ser Leu Ser Lys Thr His Leu Phe Leu Met Asp Ile Gly Ile
        195                 200                 205

Trp Leu Leu Ser Asp Arg Ala Val Glu Ile Leu Met Lys Arg Ser His
210                 215                 220
```

-continued

Lys Glu Ser Ser Glu Glu Leu Lys Tyr Tyr Asp Leu Tyr Ser Asp Phe
225                 230                 235                 240

Gly Leu Ala Leu Gly Thr His Pro Arg Ile Glu Asp Glu Glu Val Asn
            245                 250                 255

Thr Leu Ser Val Ala Ile Leu Pro Leu Pro Gly Gly Glu Phe Tyr His
        260                 265                 270

Tyr Gly Thr Ser Lys Glu Leu Ile Ser Ser Thr Leu Ser Val Gln Asn
    275                 280                 285

Lys Val Tyr Asp Gln Arg Arg Ile Met His Arg Lys Val Lys Pro Asn
290                 295                 300

Pro Ala Met Phe Val Gln Asn Ala Val Val Arg Ile Pro Leu Cys Ala
305                 310                 315                 320

Glu Asn Ala Asp Leu Trp Ile Glu Asn Ser His Ile Gly Pro Lys Trp
                325                 330                 335

Lys Ile Ala Ser Arg His Ile Ile Thr Gly Val Pro Glu Asn Asp Trp
            340                 345                 350

Ser Leu Ala Val Pro Ala Gly Val Cys Val Asp Val Val Pro Met Gly
        355                 360                 365

Asp Lys Gly Phe Val Ala Arg Pro Tyr Gly Leu Asp Asp Val Phe Lys
    370                 375                 380

Gly Asp Leu Arg Asp Ser Lys Thr Thr Leu Thr Gly Ile Pro Phe Gly
385                 390                 395                 400

Glu Trp Met Ser Lys Arg Gly Leu Ser Tyr Thr Asp Leu Lys Gly Arg
                405                 410                 415

Thr Asp Asp Leu Gln Ala Val Ser Val Phe Pro Met Val Asn Ser Val
            420                 425                 430

Glu Glu Leu Gly Leu Val Leu Arg Trp Met Leu Ser Glu Pro Glu Leu
        435                 440                 445

Glu Glu Gly Lys Asn Ile Trp Leu Arg Ser Glu His Phe Ser Ala Asp
    450                 455                 460

Glu Ile Ser Ala Gly Ala Asn Leu Lys Arg Leu Tyr Ala Gln Arg Glu
465                 470                 475                 480

Glu Phe Arg Lys Gly Asn Trp Lys Ala Leu Ala Val Asn His Glu Lys
                485                 490                 495

Ser Val Phe Tyr Gln Leu Asp Leu Ala Asp Ala Ala Glu Asp Phe Val
            500                 505                 510

Arg Leu Gly Leu Asp Met Pro Glu Leu Leu Pro Glu Asp Ala Leu Gln
        515                 520                 525

Met Ser Arg Ile His Asn Arg Met Leu Arg Ala Arg Ile Leu Lys Leu
    530                 535                 540

Asp Gly Lys Asp Tyr Arg Pro Glu Glu Gln Ala Ala Phe Asp Leu Leu
545                 550                 555                 560

Arg Asp Gly Leu Leu Asp Gly Ile Ser Asn Arg Lys Ser Thr Pro Lys
                565                 570                 575

Leu Asp Val Tyr Ser Asp Gln Ile Val Trp Gly Arg Ser Pro Val Arg
            580                 585                 590

Ile Asp Met Ala Gly Gly Trp Thr Asp Thr Pro Pro Tyr Ser Leu Tyr
        595                 600                 605

Ser Gly Gly Asn Val Val Asn Leu Ala Ile Glu Leu Asn Gly Gln Pro
    610                 615                 620

Pro Leu Gln Val Tyr Val Lys Pro Cys Lys Asp Phe His Ile Val Leu
625                 630                 635                 640

```
Arg Ser Ile Asp Met Gly Ala Met Glu Ile Val Ser Thr Phe Asp Glu
                645                 650                 655

Leu Gln Asp Tyr Lys Lys Ile Gly Ser Pro Phe Ser Ile Pro Lys Ala
                660                 665                 670

Ala Leu Ser Leu Ala Gly Phe Ala Pro Ala Phe Ser Ala Val Ser Tyr
                675                 680                 685

Ala Ser Leu Glu Glu Gln Leu Lys Asp Phe Gly Ala Gly Ile Glu Val
                690                 695                 700

Thr Leu Leu Ala Ala Ile Pro Ala Gly Ser Gly Leu Gly Thr Ser Ser
705                 710                 715                 720

Ile Leu Ala Ser Thr Val Leu Gly Ala Ile Asn Asp Phe Cys Gly Leu
                725                 730                 735

Ala Trp Asp Lys Asn Glu Ile Cys Gln Arg Thr Leu Val Leu Glu Gln
                740                 745                 750

Leu Leu Thr Thr Gly Gly Gly Trp Gln Asp Gln Tyr Gly Gly Val Leu
                755                 760                 765

Gln Gly Val Lys Leu Leu Gln Thr Glu Ala Gly Phe Ala Gln Ser Pro
                770                 775                 780

Leu Val Arg Trp Leu Pro Asp His Leu Phe Thr His Pro Glu Tyr Lys
785                 790                 795                 800

Asp Cys His Leu Leu Tyr Tyr Thr Gly Ile Thr Arg Thr Ala Lys Gly
                805                 810                 815

Ile Leu Ala Glu Ile Val Ser Ser Met Phe Leu Asn Ser Ser Leu His
                820                 825                 830

Leu Asn Leu Leu Ser Glu Met Lys Ala His Ala Leu Asp Met Asn Glu
                835                 840                 845

Ala Ile Gln Arg Gly Ser Phe Val Glu Phe Gly Arg Leu Val Gly Lys
                850                 855                 860

Thr Trp Glu Gln Asn Lys Ala Leu Asp Ser Gly Thr Asn Pro Pro Ala
865                 870                 875                 880

Val Glu Ala Ile Ile Asp Leu Ile Lys Asp Tyr Thr Leu Gly Tyr Lys
                885                 890                 895

Leu Pro Gly Ala Gly Gly Gly Tyr Leu Tyr Met Val Ala Lys Asp
                900                 905                 910

Pro Gln Ala Ala Val Arg Ile Arg Lys Ile Leu Thr Glu Asn Ala Pro
                915                 920                 925

Asn Pro Arg Ala Arg Phe Val Glu Met Thr Leu Ser Asp Lys Gly Phe
                930                 935                 940

Gln Val Ser Arg Ser
945

<210> SEQ ID NO 8
<211> LENGTH: 303
<212> TYPE: PRT
<213> ORGANISM: Exiguobacterium acetylicum
<220> FEATURE:
<221> NAME/KEY: PEPTIDE
<222> LOCATION: (1)..(303)
<223> OTHER INFORMATION: Guanosine kinase

<400> SEQUENCE: 8

Met Asn Lys Ile Ala Val Ile Gly Lys Val Phe Val Asp Ile Lys Gly
1               5                   10                  15

Thr Ser Phe Ala Pro Leu His Lys Asp Ala Lys Asn Val Gly Asp Ile
                20                  25                  30

Thr Phe Ser Asn Gly Gly Thr Gly Arg Asn Val Ala Gln Asn Leu Ala
```

```
            35                  40                  45
Val Leu Gly Asn Glu Val Arg Phe Ile Ser Thr Val Thr Asn Asp Gln
 50                  55                  60

Ile Gly Val Gly Val Leu Asp Glu Leu Lys Ser Tyr Gly Ala Asn Val
 65                  70                  75                  80

Asp His Val Glu Met Leu Glu Asp His Gly Met Gly Met Trp Leu Ala
                 85                  90                  95

Val Met Asp Asn Glu Gly Asp Leu Gln Thr Ser Ile Ser Lys Gln Pro
            100                 105                 110

Asp Ala Lys Leu Leu Glu Glu Ala Ile Leu Arg Gln Ser Ile Tyr Ala
        115                 120                 125

Leu Asp Gly Val Asp Ala Val Ala Ile Asp Leu Asp Leu Ser Val Thr
    130                 135                 140

Val Leu Glu Arg Leu Ile His Leu Cys Arg Lys Met Glu Leu Pro Leu
145                 150                 155                 160

Phe Gly Val Cys Gly His Leu Ser Val Ile Glu Arg Asn Arg His Leu
                165                 170                 175

Leu Gln Gly Phe Thr Gly Phe Ile Cys Ser Arg Glu Ala Glu Ile
            180                 185                 190

Leu Ser Asp Leu Ser Ile Val Thr Val Glu Asp Ala Ile His Val Ala
        195                 200                 205

Asn Glu Leu Ala Lys Lys Gly Ala Pro Phe Thr Val Val Thr Met Ser
    210                 215                 220

Glu Leu Gly Ala Val Tyr Val Asp Arg Arg Thr Ala Thr Ser Gly His
225                 230                 235                 240

Val Gly Thr Lys Lys Val Lys Val Val Asp Ser Thr Gly Ala Gly Asp
                245                 250                 255

Ser Phe Phe Ser Ala Val Leu Ser Glu Leu Thr Gln Glu Lys Ser Ala
            260                 265                 270

Glu Glu Ala Leu Lys Leu Gly Met Lys Val Ala Ala Glu Val Ile Ala
        275                 280                 285

Ser Thr Glu Asn Gly Leu Val Pro Glu Met Leu Asp Ala Leu Gln
    290                 295                 300

<210> SEQ ID NO 9
<211> LENGTH: 496
<212> TYPE: PRT
<213> ORGANISM: Pseudomonas aeruginosa
<220> FEATURE:
<221> NAME/KEY: PEPTIDE
<222> LOCATION: (1)..(496)
<223> OTHER INFORMATION: 2-domain polyphosphate kinase 2

<400> SEQUENCE: 9

Met Phe Glu Ser Ala Glu Val Gly His Ser Ile Asp Lys Asp Thr Tyr
  1               5                  10                  15

Glu Lys Ala Val Ile Glu Leu Arg Glu Ala Leu Leu Glu Ala Gln Phe
             20                  25                  30

Glu Leu Lys Gln Gln Ala Arg Phe Pro Val Ile Ile Leu Ile Asn Gly
         35                  40                  45

Ile Glu Gly Ala Gly Lys Gly Glu Thr Val Lys Leu Leu Asn Glu Trp
     50                  55                  60

Met Asp Pro Arg Leu Ile Glu Val Gln Ser Phe Leu Arg Pro Ser Asp
 65                  70                  75                  80

Glu Glu Leu Glu Arg Pro Pro Gln Trp Arg Phe Trp Arg Arg Leu Pro
                 85                  90                  95
```

```
Pro Lys Gly Arg Thr Gly Ile Phe Phe Gly Asn Trp Tyr Ser Gln Met
            100                 105                 110

Leu Tyr Ala Arg Val Glu Gly His Ile Lys Glu Ala Lys Leu Asp Gln
            115                 120                 125

Ala Ile Asp Ala Ala Glu Arg Phe Glu Arg Met Leu Cys Asp Glu Gly
            130                 135                 140

Ala Leu Leu Phe Lys Phe Trp Phe His Leu Ser Lys Lys Gln Leu Lys
145                 150                 155                 160

Glu Arg Leu Lys Ala Leu Glu Lys Asp Pro Gln His Ser Trp Lys Leu
                165                 170                 175

Ser Pro Leu Asp Trp Lys Gln Ser Glu Val Tyr Asp Arg Phe Val His
            180                 185                 190

Tyr Gly Glu Arg Val Leu Arg Arg Thr Ser Arg Asp Tyr Ala Pro Trp
            195                 200                 205

Tyr Val Val Glu Gly Ala Asp Glu Arg Tyr Arg Ala Leu Thr Val Gly
            210                 215                 220

Arg Ile Leu Leu Glu Gly Leu Gln Ala Ala Leu Ala Thr Lys Glu Arg
225                 230                 235                 240

Ala Lys Arg Gln Pro His Ala Ala Pro Leu Val Ser Ser Leu Asp Asn
                245                 250                 255

Arg Gly Leu Leu Asp Ser Leu Asp Leu Gly Gln Tyr Leu Asp Lys Asp
            260                 265                 270

Ala Tyr Lys Glu Gln Leu Ala Ala Glu Gln Ala Arg Leu Ala Gly Leu
            275                 280                 285

Ile Arg Asp Lys Arg Phe Arg Gln His Ser Leu Val Ala Val Phe Glu
            290                 295                 300

Gly Asn Asp Ala Ala Gly Lys Gly Gly Ala Ile Arg Arg Val Thr Asp
305                 310                 315                 320

Ala Leu Asp Pro Arg Gln Tyr His Ile Val Pro Ile Ala Ala Pro Thr
            325                 330                 335

Glu Glu Glu Arg Ala Gln Pro Tyr Leu Trp Arg Phe Trp Arg His Ile
            340                 345                 350

Pro Ala Arg Arg Gln Phe Thr Ile Phe Asp Arg Ser Trp Tyr Gly Arg
            355                 360                 365

Val Leu Val Glu Arg Ile Glu Gly Phe Cys Ala Pro Ala Asp Trp Leu
            370                 375                 380

Arg Ala Tyr Gly Glu Ile Asn Asp Phe Glu Glu Gln Leu Ser Glu Tyr
385                 390                 395                 400

Gly Ile Ile Val Val Lys Phe Trp Leu Ala Ile Asp Lys Gln Thr Gln
                405                 410                 415

Met Glu Arg Phe Lys Glu Arg Glu Lys Thr Pro Tyr Lys Arg Tyr Lys
            420                 425                 430

Ile Thr Glu Glu Asp Trp Arg Asn Arg Asp Lys Trp Asp Gln Tyr Val
            435                 440                 445

Asp Ala Val Gly Asp Met Val Asp Arg Thr Ser Thr Glu Ile Ala Pro
            450                 455                 460

Trp Thr Leu Val Glu Ala Asn Asp Lys Arg Phe Ala Arg Val Lys Val
465                 470                 475                 480

Leu Arg Thr Ile Asn Asp Ala Ile Glu Ala Ala Tyr Lys Lys Asp Lys
                485                 490                 495

<210> SEQ ID NO 10
<211> LENGTH: 177
```

<212> TYPE: PRT
<213> ORGANISM: Pasteurella multocida
<220> FEATURE:
<221> NAME/KEY: PEPTIDE
<222> LOCATION: (1)..(177)
<223> OTHER INFORMATION: inorganic pyrophosphatase

<400> SEQUENCE: 10

Met Gly Leu Glu Thr Val Pro Ala Gly Lys Ala Leu Pro Asp Asp Ile
1               5                   10                  15

Tyr Val Val Ile Glu Ile Pro Ala Asn Ser Asp Pro Ile Lys Tyr Glu
            20                  25                  30

Val Asp Lys Glu Ser Gly Ala Leu Phe Val Asp Arg Phe Met Ala Thr
        35                  40                  45

Ala Met Phe Tyr Pro Ala Asn Tyr Gly Tyr Val Asn Asn Thr Leu Ser
    50                  55                  60

Leu Asp Gly Asp Pro Val Asp Val Leu Val Pro Thr Pro Tyr Pro Leu
65                  70                  75                  80

Gln Pro Gly Ser Val Ile Arg Cys Arg Pro Val Gly Val Leu Lys Met
                85                  90                  95

Thr Asp Glu Ala Gly Ser Asp Ala Lys Val Val Ala Val Pro His Ser
            100                 105                 110

Lys Leu Thr Lys Glu Tyr Asp His Ile Lys Asp Val Asn Asp Leu Pro
        115                 120                 125

Ala Leu Leu Lys Ala Gln Ile Gln His Phe Phe Glu Ser Tyr Lys Ala
    130                 135                 140

Leu Glu Ala Gly Lys Trp Val Lys Val Asp Gly Trp Glu Gly Val Asp
145                 150                 155                 160

Ala Ala Arg Gln Glu Ile Leu Asp Ser Phe Glu Arg Ala Lys Lys Leu
                165                 170                 175

Glu

<210> SEQ ID NO 11
<211> LENGTH: 198
<212> TYPE: PRT
<213> ORGANISM: Sus scrofa
<220> FEATURE:
<221> NAME/KEY: PEPTIDE
<222> LOCATION: (1)..(198)
<223> OTHER INFORMATION: Guanylate kinase

<400> SEQUENCE: 11

Met Gly Ser Pro Arg Pro Val Val Leu Ser Gly Pro Ser Gly Ala Gly
1               5                   10                  15

Lys Ser Thr Leu Leu Lys Lys Leu Leu Gln Glu His Ser Ser Ile Phe
            20                  25                  30

Gly Phe Ser Val Ser His Thr Thr Arg Asp Pro Arg Pro Gly Glu Glu
        35                  40                  45

Asn Gly Lys Asp Tyr Tyr Phe Val Thr Arg Glu Val Met Gln Arg Asp
    50                  55                  60

Ile Ala Ala Gly Asp Phe Ile Glu His Ala Glu Phe Ser Gly Asn Leu
65                  70                  75                  80

Tyr Gly Thr Ser Lys Ala Ala Val Arg Ala Val Gln Ala Met Asn Arg
                85                  90                  95

Ile Cys Val Leu Asp Val Asp Leu Gln Gly Val Arg Asn Ile Lys Lys
            100                 105                 110

Thr Asp Leu Gln Pro Ile Tyr Ile Phe Val Gln Pro Pro Ser Leu Asp
        115                 120                 125

```
Val Leu Glu Gln Arg Leu Arg Gln Arg Asn Thr Glu Thr Glu Glu Ser
            130                 135                 140

Leu Ala Lys Arg Leu Ala Ala Lys Ala Asp Met Glu Ser Ser Lys
145                 150                 155                 160

Glu Pro Gly Leu Phe Asp Leu Ile Ile Ile Asn Asp Ser Leu Asp Lys
                    165                 170                 175

Ala Tyr Trp Ala Leu Lys Glu Ala Leu Ser Glu Glu Ile Lys Lys Ala
            180                 185                 190

Gln Ala Thr Gly His Ser
            195

<210> SEQ ID NO 12
<211> LENGTH: 558
<212> TYPE: PRT
<213> ORGANISM: Bos taurus
<220> FEATURE:
<221> NAME/KEY: PEPTIDE
<222> LOCATION: (1)..(558)
<223> OTHER INFORMATION: Glutamate dehydrogenase 1 (GLDH)

<400> SEQUENCE: 12

Met Tyr Arg Tyr Leu Gly Glu Ala Leu Leu Ser Arg Ala Gly Pro
1               5                   10                  15

Ala Ala Leu Gly Ser Ala Ser Ala Asp Ser Ala Ala Leu Leu Gly Trp
            20                  25                  30

Ala Arg Gly Gln Pro Ala Ala Ala Pro Gln Pro Gly Leu Val Pro Pro
        35                  40                  45

Ala Arg Arg His Tyr Ser Glu Ala Ala Asp Arg Glu Asp Asp Pro
    50                  55                  60

Asn Phe Phe Lys Met Val Glu Gly Phe Phe Asp Arg Gly Ala Ser Ile
65                  70                  75                  80

Val Glu Asp Lys Leu Val Glu Asp Leu Lys Thr Arg Glu Thr Glu Glu
                85                  90                  95

Gln Lys Arg Asn Arg Val Arg Ser Ile Leu Arg Ile Ile Lys Pro Cys
            100                 105                 110

Asn His Val Leu Ser Leu Ser Phe Pro Ile Arg Arg Asp Asp Gly Ser
            115                 120                 125

Trp Glu Val Ile Glu Gly Tyr Arg Ala Gln His Ser Gln His Arg Thr
130                 135                 140

Pro Cys Lys Gly Gly Ile Arg Tyr Ser Thr Asp Val Ser Val Asp Glu
145                 150                 155                 160

Val Lys Ala Leu Ala Ser Leu Met Thr Tyr Lys Cys Ala Val Val Asp
                165                 170                 175

Val Pro Phe Gly Gly Ala Lys Ala Gly Val Lys Ile Asn Pro Lys Asn
            180                 185                 190

Tyr Thr Asp Asn Glu Leu Glu Lys Ile Thr Arg Arg Phe Thr Met Glu
            195                 200                 205

Leu Ala Lys Lys Gly Phe Ile Gly Pro Gly Val Asp Val Pro Ala Pro
        210                 215                 220

Asp Met Ser Thr Gly Glu Arg Glu Met Ser Trp Ile Ala Asp Thr Tyr
225                 230                 235                 240

Ala Ser Thr Ile Gly His Tyr Asp Ile Asn Ala His Ala Cys Val Thr
                245                 250                 255

Gly Lys Pro Ile Ser Gln Gly Gly Ile His Gly Arg Ile Ser Ala Thr
            260                 265                 270
```

Gly Arg Gly Val Phe His Gly Ile Glu Asn Phe Ile Asn Glu Ala Ser
           275                 280                 285

Tyr Met Ser Ile Leu Gly Met Thr Pro Gly Phe Gly Asp Lys Thr Phe
290                 295                 300

Val Val Gln Gly Phe Gly Asn Val Gly Leu His Ser Met Arg Tyr Leu
305                 310                 315                 320

His Arg Phe Gly Ala Lys Cys Ile Thr Val Gly Glu Ser Asp Gly Ser
                325                 330                 335

Ile Trp Asn Pro Asp Gly Ile Asp Pro Lys Glu Leu Glu Asp Phe Lys
                340                 345                 350

Leu Gln His Gly Thr Ile Leu Gly Phe Pro Lys Ala Lys Ile Tyr Glu
            355                 360                 365

Gly Ser Ile Leu Glu Val Asp Cys Asp Ile Leu Ile Pro Ala Ala Ser
370                 375                 380

Glu Lys Gln Leu Thr Lys Ser Asn Ala Pro Arg Val Lys Ala Lys Ile
385                 390                 395                 400

Ile Ala Glu Gly Ala Asn Gly Pro Thr Thr Pro Glu Ala Asp Lys Ile
                405                 410                 415

Phe Leu Glu Arg Asn Ile Met Val Ile Pro Asp Leu Tyr Leu Asn Ala
                420                 425                 430

Gly Gly Val Thr Val Ser Tyr Phe Glu Trp Leu Asn Asn Leu Asn His
            435                 440                 445

Val Ser Tyr Gly Arg Leu Thr Phe Lys Tyr Glu Arg Asp Ser Asn Tyr
            450                 455                 460

His Leu Leu Met Ser Val Gln Glu Ser Leu Glu Arg Lys Phe Gly Lys
465                 470                 475                 480

His Gly Gly Thr Ile Pro Ile Val Pro Thr Ala Glu Phe Gln Asp Arg
                485                 490                 495

Ile Ser Gly Ala Ser Glu Lys Asp Ile Val His Ser Gly Leu Ala Tyr
                500                 505                 510

Thr Met Glu Arg Ser Ala Arg Gln Ile Met Arg Thr Ala Met Lys Tyr
            515                 520                 525

Asn Leu Gly Leu Asp Leu Arg Thr Ala Ala Tyr Val Asn Ala Ile Glu
530                 535                 540

Lys Val Phe Arg Val Tyr Asn Glu Ala Gly Val Thr Phe Thr
545                 550                 555

<210> SEQ ID NO 13
<211> LENGTH: 486
<212> TYPE: PRT
<213> ORGANISM: Leuconostoc mesenteroides
<220> FEATURE:
<221> NAME/KEY: PEPTIDE
<222> LOCATION: (1)..(486)
<223> OTHER INFORMATION: Glucose-6-phosphate 1-dehydrogenase (G6PDH)

<400> SEQUENCE: 13

Met Val Ser Glu Ile Lys Thr Leu Val Thr Phe Phe Gly Gly Thr Gly
1               5                   10                  15

Asp Leu Ala Lys Arg Lys Leu Tyr Pro Ser Val Phe Asn Leu Tyr Lys
                20                  25                  30

Lys Gly Tyr Leu Gln Glu His Phe Ala Ile Val Gly Thr Ala Arg Gln
            35                  40                  45

Gln Leu Ser Asp Glu Glu Phe Lys Gln Leu Val Arg Asp Ser Ile Lys
        50                  55                  60

Asp Phe Thr Glu Asp Gln Ala Gln Ala Glu Ala Phe Ile Ala His Phe

```
              65                  70                  75                  80
        Ser Tyr Arg Ala His Asp Val Thr Asp Ala Ser Tyr Gly Ile Leu
                            85                  90                  95

Lys Ser Ala Ile Glu Glu Ala Ala Thr Lys Phe Asp Ile Asp Gly Asn
                        100                 105                 110

Arg Ile Phe Tyr Met Ser Val Ala Pro Arg Phe Phe Gly Thr Ile Ala
                        115                 120                 125

Lys Tyr Leu Lys Ser Glu Gly Leu Leu Ala Asp Thr Gly Tyr Asn Arg
                        130                 135                 140

Leu Met Ile Glu Lys Pro Phe Gly Thr Ser Tyr Ala Thr Ala Glu Glu
        145                 150                 155                 160

Leu Gln Ser Asp Leu Glu Asn Ala Phe Asp Asp Gln Leu Phe Arg
                        165                 170                 175

Ile Asp His Tyr Leu Gly Lys Glu Met Val Gln Asn Ile Ala Ala Leu
                        180                 185                 190

Arg Phe Gly Asn Pro Ile Phe Asp Ala Ala Trp Asn Lys Asp Tyr Ile
                        195                 200                 205

Lys Asn Val Gln Val Thr Leu Ser Glu Val Leu Gly Val Glu Glu Arg
        210                 215                 220

Ala Gly Tyr Tyr Asp Thr Thr Gly Ala Leu Leu Asp Met Ile Gln Asn
        225                 230                 235                 240

His Thr Met Gln Ile Val Gly Trp Leu Ala Met Glu Lys Pro Glu Ser
                        245                 250                 255

Phe Asn Asp Lys Asp Ile Arg Ala Ala Lys Asn Ala Ala Phe Asn Ala
                        260                 265                 270

Leu Lys Ile Tyr Asn Glu Glu Val Asn Lys Tyr Phe Val Arg Ala
                        275                 280                 285

Gln Tyr Gly Ala Gly Asp Thr Ala Asp Tyr Lys Pro Tyr Leu Glu Glu
                        290                 295                 300

Ala Asp Val Pro Ala Asp Ser Lys Asn Asn Thr Phe Ile Ala Gly Glu
        305                 310                 315                 320

Leu Gln Phe Asp Leu Pro Arg Trp Glu Gly Val Pro Phe Tyr Val Arg
                        325                 330                 335

Ser Gly Lys Arg Leu Ala Ala Lys Gln Thr Arg Val Asp Ile Val Phe
                        340                 345                 350

Lys Ala Gly Thr Phe Asn Phe Gly Ser Glu Gln Glu Ala Gln Glu Ser
                        355                 360                 365

Val Leu Ser Ile Ile Ile Asp Pro Lys Gly Ala Ile Glu Leu Lys Leu
        370                 375                 380

Asn Ala Lys Ser Val Glu Asp Ala Phe Asn Thr Arg Thr Ile Asn Leu
        385                 390                 395                 400

Asp Trp Ala Val Ser Asp Glu Asp Lys Lys Asn Thr Pro Glu Pro Tyr
                        405                 410                 415

Glu Arg Met Ile His Asp Thr Met Asn Gly Asp Gly Ser Asn Phe Ala
                        420                 425                 430

Asp Trp Asn Gly Val Ser Ile Ala Trp Lys Phe Val Asp Ala Ile Thr
                        435                 440                 445

Ala Val Tyr Asp Ala Asp Lys Ala Pro Leu Glu Thr Tyr Lys Ser Gly
                        450                 455                 460

Ser Met Gly Pro Glu Ala Ser Asp Lys Leu Leu Ala Glu Asn Gly Asp
        465                 470                 475                 480

Ala Trp Val Phe Lys Gly
                        485
```

<210> SEQ ID NO 14
<211> LENGTH: 301
<212> TYPE: PRT
<213> ORGANISM: Ruegeria pomerovi
<220> FEATURE:
<221> NAME/KEY: PEPTIDE
<222> LOCATION: (1)..(301)
<223> OTHER INFORMATION: phosphotransferase 3 (PPK3)

<400> SEQUENCE: 14

Met Asn Arg Asn Gly Ser Thr Lys Asp Pro Arg Arg Met Thr Gly Ala
1               5                   10                  15

Ala Thr Gly Glu Ile Ser Arg Tyr Phe Asn Asp Lys Ala Pro Lys Asp
            20                  25                  30

Ile Arg Arg Ala Ile Glu Lys Ala Asp Lys Asp Ile Leu Ser Thr
        35                  40                  45

Thr Tyr Pro Tyr Asp Ala Glu Met Thr Ala Lys Asp Tyr Arg Ala Gln
    50                  55                  60

Met Glu Ala Leu Gln Ile Glu Leu Val Lys Leu Gln Ala Trp Ile Lys
65                  70                  75                  80

Gln Ser Gly Ala Arg Val Ala Leu Leu Phe Glu Gly Arg Asp Ala Ala
                85                  90                  95

Gly Lys Gly Gly Thr Ile Lys Arg Phe Arg Glu Asn Leu Asn Pro Arg
            100                 105                 110

Gly Ala Arg Val Val Ala Leu Ser Lys Pro Thr Glu Ala Glu Arg Ser
        115                 120                 125

Gln Trp Tyr Phe Gln Arg Tyr Ile Gln His Leu Pro Ser Ala Gly Glu
    130                 135                 140

Leu Val Phe Tyr Asp Arg Ser Trp Tyr Asn Arg Gly Val Val Glu His
145                 150                 155                 160

Val Phe Gly Trp Cys Asp Glu Glu Gln Arg Glu Arg Phe Phe Arg Gln
                165                 170                 175

Val Met Pro Phe Glu His Asp Leu Val Asp Asp Gly Ile His Leu Phe
            180                 185                 190

Lys Phe Trp Leu Asn Val Gly Arg Ala Glu Gln Leu Arg Arg Phe His
        195                 200                 205

Asp Arg Glu Arg Asp Pro Leu Lys Gln Trp Lys Leu Ser Pro Val Asp
    210                 215                 220

Ile Ala Gly Leu Asp Lys Trp Glu Ala Tyr Thr Thr Ala Ile Ser Gln
225                 230                 235                 240

Thr Leu Thr Arg Ser His Ser Asp Arg Ala Pro Trp Thr Val Ile Arg
                245                 250                 255

Ser Asp Asp Lys Lys Arg Ala Arg Leu Ala Ala Ile Arg Thr Val Leu
            260                 265                 270

Ser Gly Ile Asp Tyr Asp Asn Lys Asp Arg Ala Ala Val Gly Gln Pro
        275                 280                 285

Asp Ala Ala Ile Cys Gly Gly Pro Asp Ile Trp Asp Ala
    290                 295                 300

<210> SEQ ID NO 15
<211> LENGTH: 359
<212> TYPE: PRT
<213> ORGANISM: Picrophilus torridus
<220> FEATURE:
<221> NAME/KEY: PEPTIDE
<222> LOCATION: (1)..(359)
<223> OTHER INFORMATION: Glucose/galactose 1-dehydrogenase (GDH)

<400> SEQUENCE: 15

| | | | | | | | | | | | | | | |
|---|---|---|---|---|---|---|---|---|---|---|---|---|---|---|
|Met|Val|Arg|Ala|Ile|Ile|Thr|Asn|Ala|Pro|Asn|Gly|Gly|Val|Lys|Ile
1| | | | 5| | | | | 10| | | | | 15

Glu Asn Val Asn Ile Asn Glu Pro Glu His Tyr Glu Val Lys Leu Arg
              20                      25                      30

Pro Val Tyr Thr Gly Leu Cys Gly Thr Asp Arg Gly Glu Val Leu Gly
              35                      40                      45

Asn Leu Ser Phe Ala Tyr Asn Glu Pro Gly Tyr Asn Tyr Leu Val Leu
      50                      55                      60

Gly His Glu Ala Ile Cys Gln Val Ile Glu Ala Ser Glu Asn Pro Tyr
65                      70                      75                  80

Lys Ile Lys Pro Gly Asp Tyr Val Val Pro Val Arg Arg Pro Gly
              85                      90                      95

Lys Cys Val Asn Cys Arg Ile Gly Arg Glu Asp Asp Cys Ser Asp Gly
            100                    105                  110

Asp Lys His Glu Ala Gly Ile Thr Gly Leu His Gly Phe Met Arg Asp
            115                    120                  125

Tyr Phe Tyr Asp Glu Ala Lys Asn Leu Val Lys Ile Asn Asp Lys Asn
      130                      135                      140

Met Val Lys Val Ala Val Leu Thr Glu Pro Thr Lys Asn Val Met Lys
145                      150                      155                  160

Ala Phe Glu Val Phe Asp Thr Val Ser Lys Arg Ser Ile Phe Gln Gly
              165                    170                  175

Asp Asp Ser Thr Asn Leu Thr Lys Asn Cys Leu Ile Ile Gly Thr Gly
            180                    185                  190

Ser Glu Ala Phe Leu Tyr Ala Phe Met Ala Arg Glu Tyr Arg Phe Asn
            195                    200                  205

Val Phe Met Thr Asn Arg His Pro Val Gly Glu Glu Lys Leu Ser Ile
      210                      215                      220

Ile Ser Arg Ile Asn Ala Asp Phe Tyr Asp Tyr Thr Arg Glu Asp Pro
225                      230                      235                  240

Leu Lys Gly Ile Asp Leu Leu Ile Asp Thr Ser Gly Asp Pro Gly Thr
              245                    250                  255

Ile Phe Arg Phe Val Arg Lys Met Asn Tyr Asn Gly Val Val Ile Leu
            260                    265                  270

Phe Gly Thr Asn Gly Arg Ala Pro Ala Thr Ser Ile Asp Gly Glu Asp
            275                    280                  285

Ile Asp Tyr Ile Ile Glu Arg Asn Ile Ser Leu Val Gly Ser Val Asp
      290                      295                      300

Gly Ala Lys Arg His Tyr Leu Arg Ala Val Glu Tyr Leu Glu Lys Trp
305                      310                      315                  320

Asn Tyr Ser Glu Gly Ser Val Ile Asn Arg Leu Ile Thr Gly Val Phe
              325                    330                  335

Glu Pro Glu Asp Val Ser Ile Phe Thr Lys Lys Pro Gly Asn Glu Ile
            340                    345                  350

Lys Ser Val Ile Lys Trp Ser
            355

<210> SEQ ID NO 16
<211> LENGTH: 462
<212> TYPE: PRT
<213> ORGANISM: Helicobacter pylori
<220> FEATURE:
<221> NAME/KEY: PEPTIDE
<222> LOCATION: (1)..(462)
<223> OTHER INFORMATION: alpha-1,3/4-fucosyltransferase (3/4FT)

<400> SEQUENCE: 16

```
Met Phe Gln Pro Leu Leu Asp Ala Phe Ile Asp Ser Thr His Leu Asp
1               5                   10                  15

Glu Thr Thr His Lys Pro Pro Leu Asn Val Ala Leu Ala Asn Trp Trp
            20                  25                  30

Pro Leu Lys Asn Ser Glu Lys Lys Gly Phe Arg Asp Phe Ile Leu His
        35                  40                  45

Phe Ile Leu Lys Gln Arg Tyr Lys Ile Ile Leu His Ser Asn Pro Asn
    50                  55                  60

Glu Pro Ser Asp Leu Val Phe Gly Asn Pro Leu Glu Gln Ala Arg Lys
65                  70                  75                  80

Ile Leu Ser Tyr Gln Asn Thr Lys Arg Val Phe Tyr Thr Gly Glu Asn
                85                  90                  95

Glu Val Pro Asn Phe Asn Leu Phe Asp Tyr Ala Ile Gly Phe Asp Glu
            100                 105                 110

Leu Asp Phe Asn Asp Arg Tyr Leu Arg Met Pro Leu Tyr Tyr Ala Tyr
        115                 120                 125

Leu His Tyr Lys Ala Met Leu Val Asn Asp Thr Thr Ser Pro Tyr Lys
    130                 135                 140

Leu Lys Ala Leu Tyr Thr Leu Lys Lys Pro Ser His Lys Phe Lys Glu
145                 150                 155                 160

Asn His Pro Asn Leu Cys Ala Leu Ile His Asn Glu Ser Asp Pro Trp
                165                 170                 175

Lys Arg Gly Phe Ala Ser Phe Val Ala Ser Asn Pro Asn Ala Pro Ile
            180                 185                 190

Arg Asn Ala Phe Tyr Asp Ala Leu Asn Ala Ile Glu Pro Val Ala Ser
        195                 200                 205

Gly Gly Ser Val Lys Asn Thr Leu Gly Tyr Lys Val Lys Asn Lys Asn
    210                 215                 220

Glu Phe Leu Ser Gln Tyr Lys Phe Asn Leu Cys Phe Glu Asn Ser Gln
225                 230                 235                 240

Gly Tyr Gly Tyr Val Thr Glu Lys Ile Leu Asp Ala Tyr Phe Ser His
                245                 250                 255

Thr Ile Pro Ile Tyr Trp Gly Ser Pro Ser Val Ala Lys Asp Phe Asn
            260                 265                 270

Pro Lys Ser Phe Val Asn Val His Asp Phe Asn Asn Phe Asp Glu Ala
        275                 280                 285

Ile Asp Tyr Ile Arg Tyr Leu His Ala His Gln Asn Ala Tyr Leu Asp
    290                 295                 300

Met Leu Tyr Glu Asn Pro Leu Asn Thr Ile Asp Gly Lys Ala Gly Phe
305                 310                 315                 320

Tyr Gln Asp Leu Ser Phe Glu Lys Ile Leu Asp Phe Phe Lys Asn Ile
                325                 330                 335

Leu Glu Asn Asp Thr Ile Tyr His Cys Asn Asp Ala His Tyr Ser Ala
            340                 345                 350

Leu His Arg Asp Leu Asn Glu Pro Leu Val Ser Val Asp Asp Leu Arg
        355                 360                 365

Arg Asp His Asp Asp Leu Arg Val Asn Tyr Asp Asp Leu Arg Val Asn
    370                 375                 380

Tyr Asp Asp Leu Arg Val Asn Tyr Asp Asp Leu Arg Val Asn Tyr Asp
385                 390                 395                 400
```

```
Asp Leu Arg Val Asn Tyr Asp Leu Arg Arg Asp His Asp Asp Leu
                405             410             415

Arg Arg Asp His Glu Arg Leu Leu Ser Lys Ala Thr Pro Leu Leu Glu
            420                 425             430

Leu Ser Gln Asn Thr Ser Phe Lys Ile Tyr Arg Lys Ala Tyr Gln Lys
        435                 440             445

Ser Leu Pro Leu Leu Arg Ala Ile Arg Arg Trp Val Arg Lys
    450             455             460
```